United States Patent [19]
Rothemund

[11] Patent Number: 5,843,661
[45] Date of Patent: Dec. 1, 1998

[54] METHOD FOR CONSTRUCTION UNIVERSAL DNA BASED MOLECULAR TURING MACHINE

[75] Inventor: Paul W. K. Rothemund, Pasadena, Calif.

[73] Assignee: California Institute of Technology, Pasadena, Calif.

[21] Appl. No.: 639,080

[22] Filed: Apr. 24, 1996

[51] Int. Cl.[6] .............................. C12Q 1/68; C07H 21/04
[52] U.S. Cl. ................................................ 435/6; 536/23.1
[58] Field of Search ................................. 536/23.1; 435/6

[56] References Cited

PUBLICATIONS

Rozen et al. Molecular computing: Does DNA compute? Current Biology vol. 6 254–257, 1996.

*Primary Examiner*—George C. Elliott
*Assistant Examiner*—John S. Brusca
*Attorney, Agent, or Firm*—Fish & Richardson P.C.

[57] ABSTRACT

This invention discloses a novel method for constructing a Universal DNA based molecular Turing machine. Included in the invention is a method of operating the DNA based Turing machine of this invention.

29 Claims, 71 Drawing Sheets

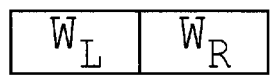
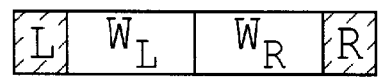
FIG. 14A  FIG. 14B
FIG. 14C
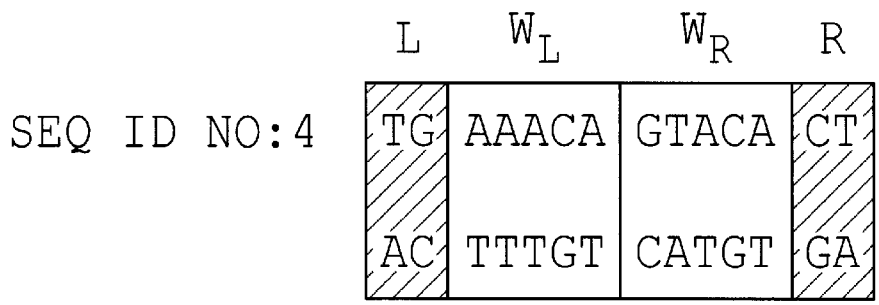
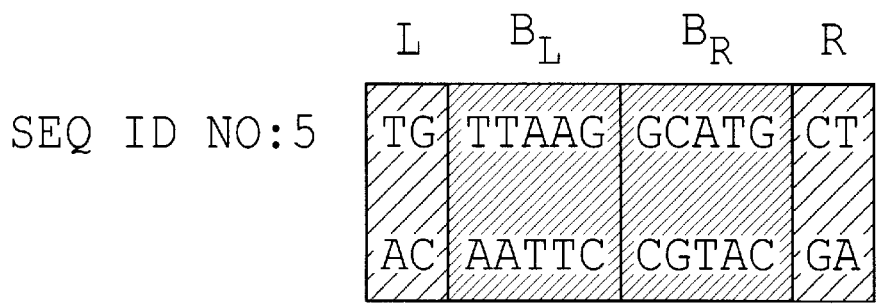
FIG. 14D

| | | | |
|---|---|---|---|
| SEQ ID NO:18 | Em: Bbv I | GCAGCNNNNNNNN<br>CGTCGNNNNNNNNNNNN | NNNNNN<br>NN |
| SEQ ID NO:19 | Sta: Fok I | GGATGNNNNNNNNN<br>CCTACNNNNNNNNNNNNN | NNNNNN<br>NN |
| SEQ ID NO:20 | Inv: BseR I | GAGGAGNNNNNNNNN<br>CTCCTCNNNNNNN | NN<br>NNNN |
| SEQ ID NO:21 | Cap: BsrD I | GCAATGNN      NN<br>CGTTAC      NNNN | |
| SEQ ID NO:22 | X: Bpm I | CTGGAGNNNNNNNNNNNNNNNN<br>GACCTCNNNNNNNNNNNNNN | NN<br>NNN |
| SEQ ID NO:23 | Sta': Hga I | GACGCNNNNN<br>CTGCGNNNNNNNNNN | NNNNNNN<br>NN |

FIG. 19

| FIG. 21 - 1 | FIG. 21 - 2 |
|---|---|
| FIG. 21 - 3 | FIG. 21 - 4 |

FIG. 21

| FIG. 22A - 1 | FIG. 22A - 2 |
| FIG. 22A - 3 | FIG. 22A - 4 |

FIG. 22A

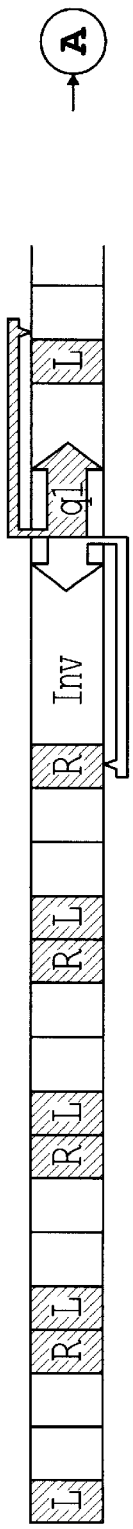
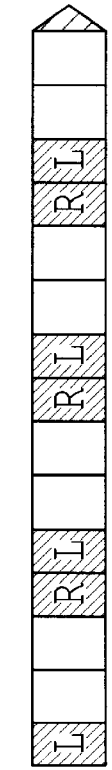
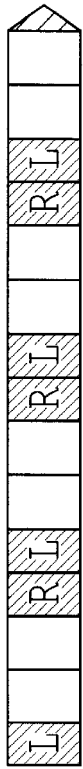
To simulate the 3x2 Busy beaver Machine
1. Cut with the state and invariant restriction enzymes. The state enzyme cuts current tape symbol W according to the current state q1.
2. Ligate in the 'Next Move' oligonucleotide: Wq1->BRq2
3. Cut cap from 'invariant' sequence
4. Ligate 'invariant' ends.
FIG. 22A - 1

| FIG. 22B - 1 | FIG. 22B - 2 |
|---|---|
| FIG. 22B - 3 | FIG. 22B - 4 |

FIG. 22B

|  |  |
|---|---|
| FIG. 22C - 1 | FIG. 22C - 2 |
| FIG. 22C - 3 | FIG. 22C - 4 |

FIG. 22C

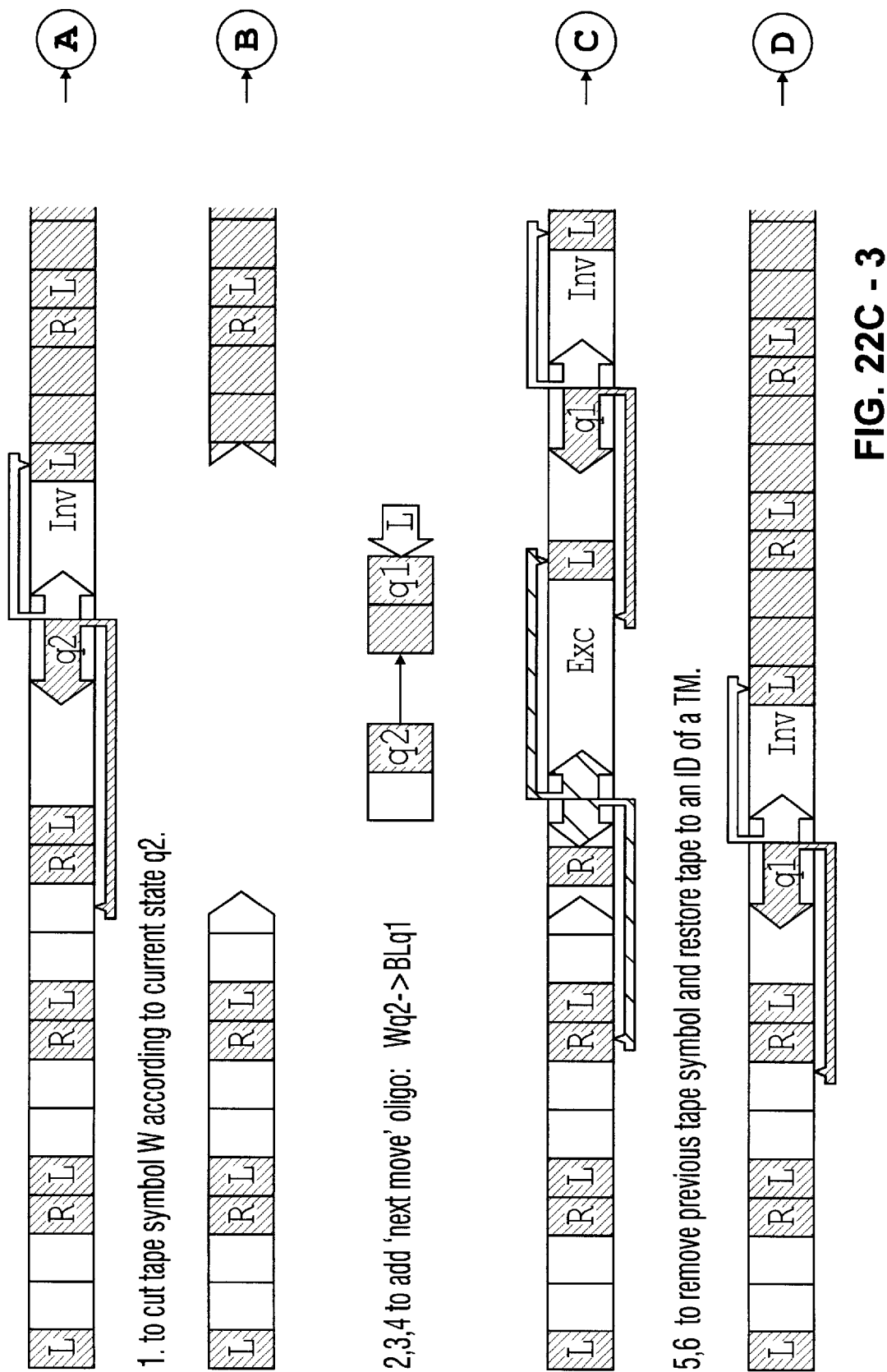

|  |  |
|---|---|
| FIG. 22D - 1 | FIG. 22D - 2 |
| FIG. 22D - 3 | FIG. 22D - 4 |

FIG. 22D

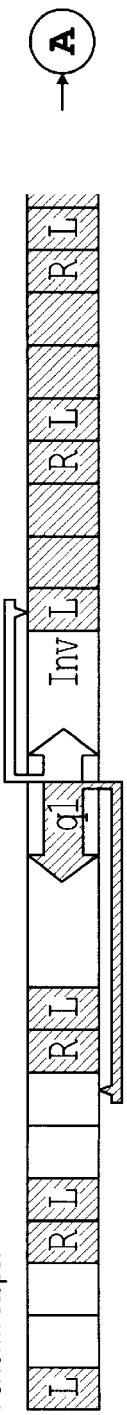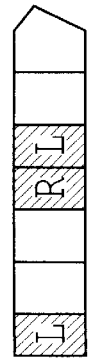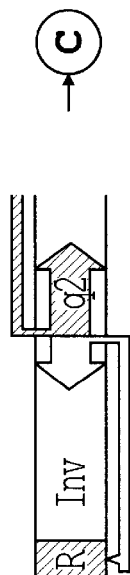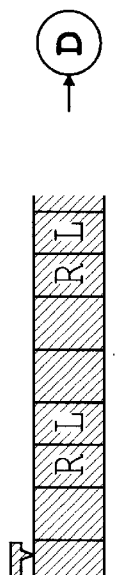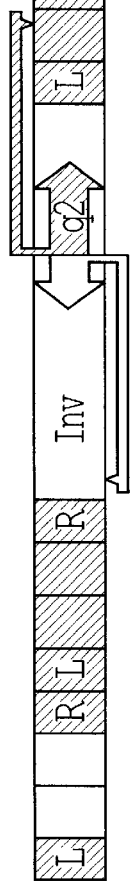
The Rest of the Computation
Perform steps:
1. to cut tape symbol W according to current state q1.
2,3,4 to add 'next move' oligo: Wq1->BRq2
5,6 to remove previous tape symbol and restore tape to an ID of a TM.
FIG. 22D - 1

| FIG. 22E - 1 | FIG. 22E - 2 |
| --- | --- |
| FIG. 22E - 3 | FIG. 22E - 4 |

FIG. 22E

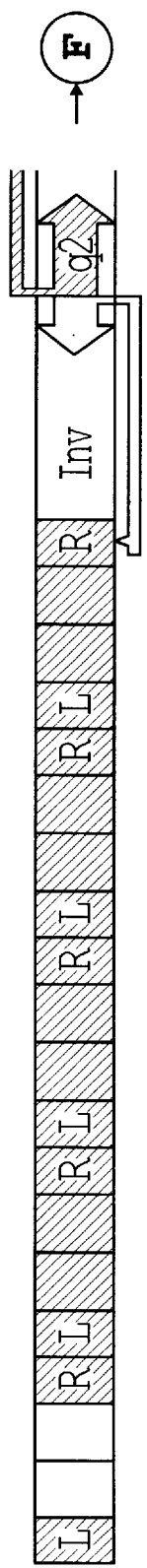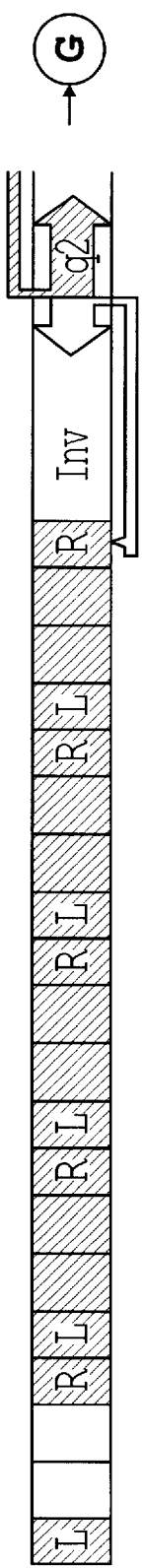
1. to cut tape symbol B according to current state q2.
2,3,4 to add 'next move' oligo: Bq2->BRq2
5,6 to remove previous tape symbol and restore tape to an ID of a TM.
FIG. 22E - 3

| FIG. 22F - 1 | FIG. 22F - 2 |
|---|---|
| FIG. 22F - 3 | FIG. 22F - 4 |

FIG. 22F

| FIG. 22G - 1 | FIG. 22G - 2 |
|---|---|
| FIG. 22G - 3 | FIG. 22G - 4 |

FIG. 22G

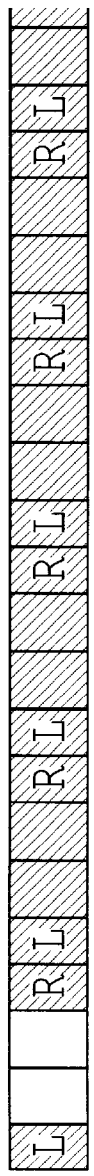
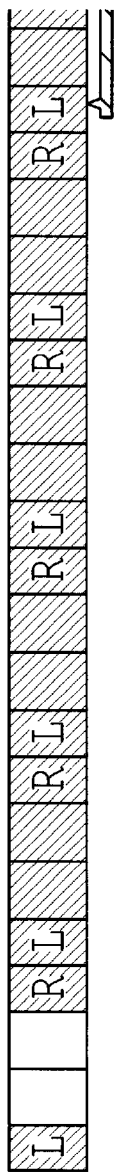
The Rest of the Computation
Perform steps:
1. to cut tape symbol B according to current state q1.
2,3,4 to add 'next move' oligo: Bq1-->BLq3
FIG. 22G - 1

FIG. 23

SEQ ID NO: 28 (Y)

| TG | AAACAG | GGTACA | CT |
|---|---|---|---|
| AC | TTTGTC | CCATGT | GA |

SEQ ID NO: 29 (O)

| TG | TTAAGG | AGCATG | CT |
|---|---|---|---|
| AC | AATTCC | TCGTAC | GA |

SEQ ID NO: 30 (I)

| TG | CCAATT | AACGAC | CT |
|---|---|---|---|
| AC | GGTTAA | TTGCTG | GA |

SEQ ID NO: 31 (A)

| TG | GGAGCC | CAGAGT | CT |
|---|---|---|---|
| AC | CCTCGG | GTCTCA | GA |

|   | $q_1$ | $q_2$ | $q_3$ | $q_4$ | $q_5$ | $q_6$ | $q_7$ |
|---|---|---|---|---|---|---|---|
| Y | $OLq_1$ | $OLq_1$ | $YLq_3$ | $YLq_4$ | $YRq_5$ | $YRq_6$ | $ORq_7$ |
| O | $OLq_1$ | $YRq_2$ | Halt | $YRq_5$ | $YLq_3$ | $ALq_3$ | $YRq_6$ |
| I | $ILq_2$ | $ARq_2$ | $ALq_3$ | $ILq_7$ | $ARq_5$ | $ARq_6$ | $IRq_7$ |
| A | $ILq_1$ | $YLq_3$ | $ILq_4$ | $ILq_4$ | $IRq_5$ | $IRq_6$ | $ORq_2$ |

FIG. 24

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: oligonucleotide ( i x ) FEATURE:
        ( B ) LOCATION: 6-14
        ( D ) OTHER INFORMATION: where N at positions 6-14 can be
            adenine, guanine, cytosine, thymine or uracil ( x i ) SEQUENCE DESCRIPTION: SEQ ID NO:1:

C G A T G N N N N N   N N N N G A A A C A      2 0

( 2 ) INFORMATION FOR SEQ ID NO:2:

( i ) SEQUENCE CHARACTERISTICS:
        ( A ) LENGTH: 19
        ( B ) TYPE: nucleic acid
        ( C ) STRANDEDNESS:double
        ( D ) TOPOLOGY: linear ( i i ) MOLECULE TYPE: other nucleic acid
        ( A ) DESCRIPTION: oligonucleotide ( i x ) FEATURE:
        ( B ) LOCATION: 6-13
        ( D ) OTHER INFORMATION: where N at positions 6-13 can be
            adenine, guanine, cytosine, thymine or uracil ( x i ) SEQUENCE DESCRIPTION: SEQ ID NO:2:

CGATGNNNNN NNNGAAACA         19

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS:double
        ( D ) TOPOLOGY: linear ( i i ) MOLECULE TYPE: other nucleic acid
        ( A ) DESCRIPTION: oligonucleotide ( i x ) FEATURE:
        ( B ) LOCATION: 6-12
        ( D ) OTHER INFORMATION: where N at positions 6-12 can be
            adenine, guanine, cytosine, thymine or uracil ( x i ) SEQUENCE DESCRIPTION: SEQ ID NO:3:

CGATGNNNNN NNGAAACA         18

( 2 ) INFORMATION FOR SEQ ID NO:4:

( i ) SEQUENCE CHARACTERISTICS:
        ( A ) LENGTH: 14 base pairs
        ( B ) TYPE: nucleic acid
        ( C ) STRANDEDNESS:double
        ( D ) TOPOLOGY: linear ( i i ) MOLECULE TYPE: other nucleic acid
        ( A ) DESCRIPTION: oligonucleotide ( x i ) SEQUENCE DESCRIPTION: SEQ ID NO:4:

TGAAACAGTA CACT         14

( 2 ) INFORMATION FOR SEQ ID NO:5:

( i ) SEQUENCE CHARACTERISTICS:
        ( A ) LENGTH: 14 base pairs
        ( B ) TYPE: nucleic acid
        ( C ) STRANDEDNESS:double
        ( D ) TOPOLOGY: linear ( i i ) MOLECULE TYPE: other nucleic acid
        ( A ) DESCRIPTION: oligonucleotide ( x i ) SEQUENCE DESCRIPTION: SEQ ID NO:5:

TGTTAAGGCA TGCT         14

( 2 ) INFORMATION FOR SEQ ID NO:6:

( i ) SEQUENCE CHARACTERISTICS:
        ( A ) LENGTH: 27 base pairs (B) TYPE: nucleic acid
(C) STRANDEDNESS: double
(D) TOPOLOGY: linear (ii) MOLECULE TYPE: other nucleic acid
(A) DESCRIPTION: oligonucleotide (ix) FEATURE:
(B) LOCATION: 6-13
(D) OTHER INFORMATION: where N at positions 6-13 can be adenine, guanine, cytosine, thymine or uracil (xi) SEQUENCE DESCRIPTION: SEQ ID NO:6:

GGATGNNNNN NNNTGAAACA GTACACT                27

(2) INFORMATION FOR SEQ ID NO:7:

(i) SEQUENCE CHARACTERISTICS:
(A) LENGTH: 26 base pairs
(B) TYPE: nucleic acid
(C) STRANDEDNESS: double
(D) TOPOLOGY: linear (ii) MOLECULE TYPE: genomic (ix) FEATURE:
(B) LOCATION:
(D) OTHER INFORMATION:

(xi) SEQUENCE DESCRIPTION: SEQ ID NO:7:

GGATGNNNNN NNTGAAACAG TACACT                 26

(2) INFORMATION FOR SEQ ID NO:8:

(i) SEQUENCE CHARACTERISTICS:
(A) LENGTH: 25 base pairs
(B) TYPE: nucleic acid
(C) STRANDEDNESS: double
(D) TOPOLOGY: linear (ii) MOLECULE TYPE: genomic (ix) FEATURE:
(B) LOCATION:
(D) OTHER INFORMATION:

(xi) SEQUENCE DESCRIPTION: SEQ ID NO:8:

GGATGNNNNN NTGAAACAGT ACACT                  25

(2) INFORMATION FOR SEQ ID NO:9:

(i) SEQUENCE CHARACTERISTICS:
(A) LENGTH: 27 base pairs
(B) TYPE: nucleic acid
(C) STRANDEDNESS: double
(D) TOPOLOGY: linear (ii) MOLECULE TYPE: other nucleic acid
(A) DESCRIPTION: oligonucleotide (ix) FEATURE:
(B) LOCATION: 6-13
(D) OTHER INFORMATION: where N at positions 6-13 can be adenine, guanine, cytosine, thymine or uracil (xi) SEQUENCE DESCRIPTION: SEQ ID NO:9:

GGATGNNNNN NNNTGTTAAG GCATGCT                27

(2) INFORMATION FOR SEQ ID NO:10:

(i) SEQUENCE CHARACTERISTICS:
(A) LENGTH: 26 base pairs (B) TYPE: nucleic acid
(C) STRANDEDNESS: double
(D) TOPOLOGY: linear (ii) MOLECULE TYPE: other nucleic acid
   (A) DESCRIPTION: oligonucleotide (ix) FEATURE:
   (B) LOCATION: 6-12
   (D) OTHER INFORMATION: where N at positions 6-12 can be adenine, guanine, cytosine, thymine or uracil (xi) SEQUENCE DESCRIPTION: SEQ ID NO:10:

GGATGNNNNN NNTGTTAAGG CATGCT     26

(2) INFORMATION FOR SEQ ID NO:11:

(i) SEQUENCE CHARACTERISTICS:
   (A) LENGTH: 25 base pairs
   (B) TYPE: nucleic acid
   (C) STRANDEDNESS: double
   (D) TOPOLOGY: linear (ii) MOLECULE TYPE: other nucleic acid
   (A) DESCRIPTION: oligonucleotide (ix) FEATURE:
   (B) LOCATION: 6-11
   (D) OTHER INFORMATION: where N at positions 6-11 can be adenine, guanine, cytosine, thymine or uracil (xi) SEQUENCE DESCRIPTION: SEQ ID NO:11:

GGATGNNNNN NTGTTAAGGC ATGCT     25

(2) INFORMATION FOR SEQ ID NO:12:

(i) SEQUENCE CHARACTERISTICS:
   (A) LENGTH: 27 base pairs
   (B) TYPE: nucleic acid
   (C) STRANDEDNESS: double
   (D) TOPOLOGY: linear (ii) MOLECULE TYPE: other nucleic acid
   (A) DESCRIPTION: oligonucleotide (ix) FEATURE:
   (B) LOCATION: 15-22
   (D) OTHER INFORMATION: where N at positions 15-22 can be adenine, guanine, cytosine, thymine or uracil (xi) SEQUENCE DESCRIPTION: SEQ ID NO:12:

TGAAACAGTA CACTNNNNNN NNCATCC     27

(2) INFORMATION FOR SEQ ID NO:13:

(i) SEQUENCE CHARACTERISTICS:
   (A) LENGTH: 26 base pairs
   (B) TYPE: nucleic acid
   (C) STRANDEDNESS: double
   (D) TOPOLOGY: linear (ii) MOLECULE TYPE: other nucleic acid
   (A) DESCRIPTION: oligonucleotide (ix) FEATURE:
   (B) LOCATION: 15-21
   (D) OTHER INFORMATION: where N at positions 15-21 can be adenine, guanine, cytosine, thymine or uracil (xi) SEQUENCE DESCRIPTION: SEQ ID NO:13:

TGAAACAGTA CACTNNNNNN NCATCC     26

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS:double
        ( D ) TOPOLOGY: linear ( i i ) MOLECULE TYPE: other nucleic acid
        ( A ) DESCRIPTION: oligonucleotide ( i x ) FEATURE:
        ( B ) LOCATION: 15-20
        ( D ) OTHER INFORMATION: where N at positions 15-20 can be
            adenine, guanine, cytosine, thymine or uracil ( x i ) SEQUENCE DESCRIPTION: SEQ ID NO:14:

TGAAACAGTA CACTNNNNNN CATCC 25

( 2 ) INFORMATION FOR SEQ ID NO:15:

( i ) SEQUENCE CHARACTERISTICS:
        ( A ) LENGTH: 27 base pairs
        ( B ) TYPE: nucleic acid
        ( C ) STRANDEDNESS:double
        ( D ) TOPOLOGY: linear ( i i ) MOLECULE TYPE: other nucleic acid
        ( A ) DESCRIPTION: oligonucleotide ( i x ) FEATURE:
        ( B ) LOCATION: 15-22
        ( D ) OTHER INFORMATION: where N at positions 15-22 can be
            adenine, guanine, cytosine, thymine or uracil ( x i ) SEQUENCE DESCRIPTION: SEQ ID NO:15:

TGTTAAGGCA TGCTNNNNNN NNCATCC 27

( 2 ) INFORMATION FOR SEQ ID NO:16:

( i ) SEQUENCE CHARACTERISTICS:
        ( A ) LENGTH: 26 base pairs
        ( B ) TYPE: nucleic acid
        ( C ) STRANDEDNESS:double
        ( D ) TOPOLOGY: linear ( i i ) MOLECULE TYPE: other nucleic acid
        ( A ) DESCRIPTION: oligonucleotide ( i x ) FEATURE:
        ( B ) LOCATION: 15-21
        ( D ) OTHER INFORMATION: where N at positions 15-21 can be
            adenine, guanine, cytosine, thymine or uracil ( x i ) SEQUENCE DESCRIPTION: SEQ ID NO:16:

TGTTAAGGCA TGCTNNNNNN NCATCC 26

( 2 ) INFORMATION FOR SEQ ID NO:17:

( i ) SEQUENCE CHARACTERISTICS:
        ( A ) LENGTH: 25 base pairs
        ( B ) TYPE: nucleic acid
        ( C ) STRANDEDNESS:double
        ( D ) TOPOLOGY: linear ( i i ) MOLECULE TYPE: other nucleic acid
        ( A ) DESCRIPTION: oligonucleotide ( i x ) FEATURE:
        ( B ) LOCATION: 15-20
        ( D ) OTHER INFORMATION: where N at positions 15-20 can be
            adenine, guanine, cytosine, thymine or uracil ( x i ) SEQUENCE DESCRIPTION: SEQ ID NO:17:

```
TGTTAAGGCA TGCTNNNNNN CATCC                                                                         25
```

( 2 ) INFORMATION FOR SEQ ID NO:18:

( i ) SEQUENCE CHARACTERISTICS:
        ( A ) LENGTH: 19 base pairs
        ( B ) TYPE: nucleic acid
        ( C ) STRANDEDNESS:double
        ( D ) TOPOLOGY: linear ( i i ) MOLECULE TYPE: other nucleic acid
        ( A ) DESCRIPTION: oligonucleotide ( i x ) FEATURE:
        ( B ) LOCATION: 6-19
        ( D ) OTHER INFORMATION: where N at positions 6-19 can be
            adenine, guanine, cytosine, thymine or uracil ( x i ) SEQUENCE DESCRIPTION: SEQ ID NO:18:

```
GCAGCNNNNN NNNNNNNNN                                                                                19
```

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS:double
        ( D ) TOPOLOGY: linear ( i i ) MOLECULE TYPE: other nucleic acid
        ( A ) DESCRIPTION: oligonucleotide ( i x ) FEATURE:
        ( B ) LOCATION: 6-20
        ( D ) OTHER INFORMATION: where N at positions 6-20 can be
            adenine, guanine, cytosine, thymine or uracil ( x i ) SEQUENCE DESCRIPTION: SEQ ID NO:19:

```
GGATGNNNNN NNNNNNNNNN                                                                               20
```

( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS:double
        ( D ) TOPOLOGY: linear ( i i ) MOLECULE TYPE: other nucleic acid
        ( A ) DESCRIPTION: oligonucleotide ( i x ) FEATURE:
        ( B ) LOCATION: 6-18
        ( D ) OTHER INFORMATION: where N at positions 6-18 can be
            adenine, guanine, cytosine, thymine or uracil ( x i ) SEQUENCE DESCRIPTION: SEQ ID NO:20:

```
GAGGAGNNNN NNNNNNNN                                                                                 18
```

( 2 ) INFORMATION FOR SEQ ID NO:21:

( i ) SEQUENCE CHARACTERISTICS:
        ( A ) LENGTH: 10 base pairs
        ( B ) TYPE: nucleic acid
        ( C ) STRANDEDNESS:double
        ( D ) TOPOLOGY: linear ( i i ) MOLECULE TYPE: other nucleic acid
        ( A ) DESCRIPTION: oligonucleotide ( i x ) FEATURE:
        ( B ) LOCATION: 7-10

(D) OTHER INFORMATION: where N at positions 7-10 can be
    adenine, guanine, cytosine, thymine or uracil (x i) SEQUENCE DESCRIPTION: SEQ ID NO:21:

GCAATGNNNN                                                                                          10

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS:double
        (D) TOPOLOGY: linear (i i) MOLECULE TYPE: other nucleic acid
        (A) DESCRIPTION: oligonucleotide (i x) FEATURE:
        (B) LOCATION: 7-24
        (D) OTHER INFORMATION: where N at positions 6-13 can be
            adenine, guanine, cytosine, thymine or uracil (x i) SEQUENCE DESCRIPTION: SEQ ID NO:22:

CTGGAGNNNN NNNNNNNNNN NNNN                                                                          24

(2) INFORMATION FOR SEQ ID NO:23:

(i) SEQUENCE CHARACTERISTICS:
        (A) LENGTH: 17 base pairs
        (B) TYPE: nucleic acid
        (C) STRANDEDNESS:double
        (D) TOPOLOGY: linear (i i) MOLECULE TYPE: other nucleic acid
        (A) DESCRIPTION: oligonucleotide (i x) FEATURE:
        (B) LOCATION: 6-17
        (D) OTHER INFORMATION: where N at positions 6-17 can be
            adenine, guanine, cytosine, thymine or uracil (x i) SEQUENCE DESCRIPTION: SEQ ID NO:23:

GACGCNNNNN NNNNNNN                                                                                  17

(2) INFORMATION FOR SEQ ID NO:24:

(i) SEQUENCE CHARACTERISTICS:
        (A) LENGTH: 69 base pairs
        (B) TYPE: nucleic acid
        (C) STRANDEDNESS:double
        (D) TOPOLOGY: linear (i i) MOLECULE TYPE: other nucleic acid
        (A) DESCRIPTION: oligonucleotide (i x) FEATURE:
        (B) LOCATION: 6-12
        (D) OTHER INFORMATION: where N at positions 6-12 can be
            adenine, guanine, cytosine, thymine or uracil (x i) SEQUENCE DESCRIPTION: SEQ ID NO:24:

TGAAACAGTA CACTNNNNN NNCTCCTCGG ATGNNNNNN NTGAAACAGT ACACTTGAAA                                      60

CAGTACACT                                                                                           69

(2) INFORMATION FOR SEQ ID NO:25:

(i) SEQUENCE CHARACTERISTICS:
        (A) LENGTH: 103 base pairs
        (B) TYPE: nucleic acid
        (C) STRANDEDNESS:double
        (D) TOPOLOGY: linear ( i i ) MOLECULE TYPE: other nucleic acid
(A) DESCRIPTION: oligonucleotide ( i x ) FEATURE:
(B) LOCATION: 37-44, 56-60, 63- 77
(D) OTHER INFORMATION: where N at positions 37-44, 56-60 or 63-77 can be adenine, guanine, cytosine, thymine or uracil ( x i ) SEQUENCE DESCRIPTION: SEQ ID NO:25:

TGAAACAGTA CACTGCAATG CTTGTTAAGG CATGCTNNNN NNNNCTCCTC GGATGNNNNN 60

CTNNNNNNNN NNNNNNNGAA ACAGTCACTT GAAACAGTAC ACT 103

(2) INFORMATION FOR SEQ ID NO:26:

( i ) SEQUENCE CHARACTERISTICS:
(A) LENGTH: 23 base pairs
(B) TYPE: nucleic acid
(C) STRANDEDNESS:double
(D) TOPOLOGY: linear ( i i ) MOLECULE TYPE: other nucleic acid
(A) DESCRIPTION: oligonucleotide ( x i ) SEQUENCE DESCRIPTION: SEQ ID NO:26:

GTGTACAAGA AGAACATCGT GCC 23

(2) INFORMATION FOR SEQ ID NO:27:

( i ) SEQUENCE CHARACTERISTICS:
(A) LENGTH: 32 base pairs
(B) TYPE: nucleic acid
(C) STRANDEDNESS:double
(D) TOPOLOGY: linear ( i i ) MOLECULE TYPE: other nucleic acid
(A) DESCRIPTION: oligonucleotide ( i x ) FEATURE:
(B) LOCATION: 15-20
(D) OTHER INFORMATION: where N at positions 6-13 can be adenine, guanine, cytosine, thymine or uracil ( x i ) SEQUENCE DESCRIPTION: SEQ ID NO:27:

AACATGTCTA CAATCTCACA RTTNACNGTN GT 32

(2) INFORMATION FOR SEQ ID NO:28:

( i ) SEQUENCE CHARACTERISTICS:
(A) LENGTH: 20 base pairs
(B) TYPE: nucleic acid
(C) STRANDEDNESS:double
(D) TOPOLOGY: linear ( i i ) MOLECULE TYPE: other nucleic acid
(A) DESCRIPTION: oligonucleotide ( x i ) SEQUENCE DESCRIPTION: SEQ ID NO:28:

AACATGTCTA CAATCTCACA 20

(2) INFORMATION FOR SEQ ID NO:29:

( i ) SEQUENCE CHARACTERISTICS:
(A) LENGTH: 38 base pairs
(B) TYPE: nucleic acid
(C) STRANDEDNESS:double
(D) TOPOLOGY: linear ( x i ) SEQUENCE DESCRIPTION: SEQ ID NO:29:

-continued

AATAACCTCT TTACGGCCCA AATTCARTWY GCNTAYGA                                     38

( 2 ) INFORMATION FOR SEQ ID NO:30:

( i ) SEQUENCE CHARACTERISTICS:
        ( A ) LENGTH: 38 base pairs
        ( B ) TYPE: nucleic acid
        ( C ) STRANDEDNESS:double
        ( D ) TOPOLOGY: linear ( i i ) MOLECULE TYPE: other nucleic acid
        ( A ) DESCRIPTION: oligonucleotide ( x i ) SEQUENCE DESCRIPTION: SEQ ID NO:30:

CCAACGAGTG TGATGTCAGC CATTTAYGGN AARCCNGT                                    38

( 2 ) INFORMATION FOR SEQ ID NO:31:

( i ) SEQUENCE CHARACTERISTICS:
        ( A ) LENGTH: 21 base pairs
        ( B ) TYPE: nucleic acid
        ( C ) STRANDEDNESS:double
        ( D ) TOPOLOGY: linear ( i i ) MOLECULE TYPE: other nucleic acid
        ( A ) DESCRIPTION: oligonucleotide ( x i ) SEQUENCE DESCRIPTION: SEQ ID NO:31:

CCAACGAGTG TGATGTCAGC C                                                       21

METHOD FOR CONSTRUCTION UNIVERSAL DNA BASED MOLECULAR TURING MACHINE

FIELD OF THE INVENTION

This invention relates to the fields of computer science and molecular biology. Specifically, this invention relates to the field of computing machines and computing programs. More specifically, this invention describes a novel method of constructing a Universal molecular Turing machine that is capable of simulating any Turing machine and hence any algorithm. The Turing machine of the present invention is comprised of a single circular unit of DNA, restriction enzymes, transition oligonucleotides and DNA ligases. The transition table of a Turing machine is encoded with oligonucleotides, representing the Turing tape, head position and state, as a single molecule of DNA. Transitions are effected using restriction enzyme chemistry. A total of 6 distinct chemical steps are repeated to simulate one time step in a given Turing machine.

BACKGROUND OF THE INVENTION

A Turing machine is a model of computation, or a way of representing and performing a given computation. (Turing (1936) Proc. Math. Soc. Series 2). Turing machines are mathematically equivalent to many other models of computation, such as cellular automata (Lindgren and Nordahl (1990) Complex Systems 4:299–318), neural networks (Siegelmann (1995) Journal of Molecular Biology 50:132–150), and digital computers (Hopcroft and Ullman (1979) in *Introduction to Automata Theory Languages and Computation* sec. 7.6 Addison-Wesley Pub. Co.). Because no model of computation is more powerful than a Turing machine, it is considered to embody what is meant when a problem is referred to as being computable (Church's Thesis). In other words, anything for which a procedure or algorithm can be written, can be computed by a Turing machine. Turing machines have facilitated the proof of many important theories regarding the nature and limits of computation, such as the undecidability of the halting problem and the existence of uncomputable functions.

Specifically, a Turing machine is a finite-state machine attached to a storage tape that is infinitely long in both directions. A finite-state machine is a device that can exist in only a limited number of different states. There is an alphabet or set of symbols associated with the device and any string of symbols from this alphabet may be given to the machine as input. A finite-state machine operates in discrete units of time. The device reads one symbol of the input during each unit of time. On the basis of its state and this symbol, it changes to a new state. This constitutes a single move. It is then ready to perform another move with the next input symbol and this new state. This process continues until the entire input string is read or, in other words, until the end of the computation. After reading all of the input, the machine either accepts or rejects the input depending upon the outcome of the computation.

A schematic representation of a Turing machine 10 operating on its tape 12 is depicted in FIG. 1. The tape 12 can be thought of as a sequence of memory cells 14 extending indefinitely in both directions. By indefinitely it is meant that if the Turing machine runs out of tape more cells are appended. Each cell 14 stores a single symbol from the set $S=\{S_0, S_1, \ldots S_N\}$. A Turing machine has two components: a head 16 and a finite control 18. The head points to one cell of the tape and reads a symbol from that cell, writes a symbol to that cell, or moves right or left to an adjacent cell. At each time step in the operation of the Turing machine 10, the head 16 performs a compound operation composed of a single read, write and move. The finite control 18—the "brain" of the Turing machine—directs the head. A special cell 20 in the finite control contains the state of the machine, a member of the set $Q=\{q_0, \ldots q_p\}$. The rest of the finite control houses the transition table 22 which defines how the finite control will instruct the head 16 when the head points to a given symbol $s_y$ and the finite control 18 is in a given state $q_x$.

For every possible pair $(s_y, q_x)$ the transition table 22 provides a triple representation $(s_w, q_y, m)$ where $s_w$ is the symbol written by the head, $q_y$ is the new state for the machine, and m is the movement made by the head, L, R or H, for left, right or halt, respectively. If m=H the machine enters a special state $q_0$, known as the halting state and the computation is complete. Typically, the halting state $q_0$ is left out of the specification of a Turing machine and only the non-halting states are considered. The size of a Turing machine with j symbols and k non-halting states is represented as j×k.

A Turing machine can be divided into constant and variable elements. The variable elements of the model are the head position, the state of the finite control, and the contents of the tape, which taken together, are referred to as the instantaneous description or ID of the Turing machine. The constant element of the model is the transition table, which is also referred to as the machine portion of the model. The Turing machine model, divided in this way, can be envisioned as an operator that acts on an ID at time T and produces a new ID at time T+1. (Abu-Mostafa (1992) *Notes on Information and Complexity*, Sec. 2.2).

FIG. 2 illustrates a simulation of a three state Busy Beaver (BB-3) Turing machine. The Busy Beaver model for a Turing machine with N states (BB-N) entails the problem of designing an N-state Turing machine with two symbols, black (B) and white (W), that prints the greatest number of black symbols before halting. (Abu-Mostafa (1992) *Notes on Information and Complexity*, Sec. 2.2). Referring to FIG. 2, the BB-3 Turing machine has a two symbol alphabet $S=\{B, W\}$ and three (non-halting) states $Q=\{q_1, q_2, q_3\}$. The transition table for the machine is depicted in FIG. 2. The symbols B and NV are represented by black and white boxes. Smaller gray boxes represent the three states $q_1, q_2$, and $q_3$. A movement to the left is given by a left arrow and a movement to the right by a right arrow. The next move for the BB-3 machine, if it is in state $q_1$, and the head points to a W, is to the right. The machine writes a B on the tape, changes to state $q_2$, and moves to the right, which is represented as $(B, q_2, R)$. This transition is shown in FIG. 3. The operations required to bring the tape from an ID at the current timestep T, to an ID at time T+1 are given at the right of each tape. The machine halts when it is in state $q_3$ and the head points to a B. On a blank tape of white symbols it takes 13 steps to print 6 black symbols and halt.

While a Turing machine may be constructed to implement any specific algorithm imaginable, it is impractical to build a physical machine to solve each new problem. Fortunately, Turing machines can be constructed that take as an input a description and data tape of another Turing machine, and simulates that Turing machine on its own tape. Such a Turing machine is known as a Universal Turing Machine (UTM). Personal computers are good approximations of Universal Turing Machines, in that the programs that they run are descriptions of specific algorithms and hence, specific Turing machines. Personal computers fall short of UTMs, however, because their memory cannot be expanded every time more storage is needed.

The notion of a molecular computer, whose basic operations are performed chemically instead of electronically, offers the possibility of storing and manipulating information at densities impossible to realize with current computers. This is because on a chemical level $10^{14}$ molecules can be manipulated at once. (Adleman (1994) Science 266:1021–1024). The search for a chemistry rich enough to make a molecular computer, therefore, has been the focus of a great deal of research. Leonard Adleman used the chemistry of DNA to solve the directed Hamiltonian path problem. (Adleman (1994) Science 266:1021–1024). This was an important first step towards realizing molecular computation. Adleman's approach does not, however, render a universally programmable molecular computer that can solve any problem for which an algorithm can be written.

To construct a general molecular computer some Universal model of computation (e.g. a digital computer, neural network, Turing machine, etc.) must be expressed in terms of chemical reactions. A number of researchers have proposed such a molecular computer using hypothetical chemical reactions. In 1982, for example, Bennett gave a schematic description of a DNA Turing machine using imaginary enzymes capable of recognizing and changing single bases of DNA. (Bennett (1982) Int. J. of Theoretical Physics 21:905–940). Other researchers have since proposed the construction of chemical computers using different sets of hypothetical chemical species and different models of computation. Hjelmfelt et al. (1991) Proc. Natl. Acad. Sci. 88:10983–10987, describe the construction of chemical neural networks, which they propose might be used to make other general computers, such as, Turing machines. Models such as these delineate how a computation would proceed, based upon hypothetical chemical species and reactions.

Beaver describes a Turing machine based on "site-directed mutagenesis." (Beaver, "Computing with DNA", (Journal of Computational Biology, 2:1, 1995). The transitions depend on the hybridization of a partially mismatched strand of DNA to the head region of a single-stranded DNA Turing tape. Regions outside of the partially mismatched region are "filled in" with DNA polymerase to complete a "mutant strand." The mutant strand and parent strand are melted, the mutant strand copied into double-stranded DNA, and the original parent strand is digested by a single-stranded nuclease. Thus, the tapes are copied twice each timestep using DNA polymerase. To ensure that the single-stranded transition oligonucleotides added apply to the Turing tape, the Turing machines are separated at each step according to their state and symbol using affinity chromatography. Finally, at several stages the Turing tape is maintained as single-stranded DNA, which is more susceptible to cleavage and degradation than double-stranded molecules.

Smith makes use of circular DNA molecules as the Turing tape and effect, transitions using restriction enzymes. (Smith and Schweitzer, "DNA Computers in vitro and in vivo", ( NEC Technical Report of Feb. 20, 1995, presented at DIMACS Workshop on DNA Based Computing, Princeton N.J. Apr. 4, 1995). Information about the current state/symbol is encoded before or after the restriction site and is exposed by melting the Turing tape into a single-strand, which as stated above is more susceptible to cleavage and degradation than double-stranded DNA. Additionally, Smith makes extensive use of DNA polymerase to restore the tapes to double-stranded form at each timestep.

A single strand of DNA can be likened to a storage tape that can support a four symbol alphabet S={A, G, C, T} representing the nucleobases adenine, guanine, cytosine and thymine. These nucleobases are not bonded directly to one another, but rather hand from a phosphate and sugar backbone (FIG. 4). The DNA strand's backbone has a polarity; that is, a sequence of DNA is distinct from its reverse. To represent the polarity, one end of the DNA strand is referred to as the 5' end—its terminal phosphate is attached to the 5' oxygen of a sugar—and the other end is referred to as the 3' end—its terminal phosphate is attached to the 3' oxygen of the sugar.

Taken as pairs the nucleotides A and T and the nucleotides C and G are said to be complementary. This means that an A-T pair or a C-G pair can form weak<, non-covalent bonds known as hydrogen bonds that serve to hold them together. When a stretch of single-stranded DNA encounters another stretch of single-stranded DNA that has a complementary sequence the hydrogen bond interactions between complementary pairs join the two strands in a process referred to as annealing. A piece of single-stranded DNA will only anneal to its complement if it has the opposite polarity.

The similarity of DNA to the tape of a Turing machine has prompted a number of researchers to envision DNA as a media for computation. (Adleman (1994) Science 266:1021–1024; Beaver, "Computing with DNA", (Journal of Computational Biology, 2:1, 1995; Smith and Schweitzer, "DNA Computers in vitro and in vivo", NEC Technical Report of Feb. 20 1995, presented at DIMACS Workshop on DNA Based Computing, Princeton N.J. Apr. 4, 1995; Bennett (1973) IBM J. of Research and Development 17:525–532). To create a DNA Turing machine some real operations on DNA must be identified that can be made to correspond to the operations of a Turing machine.

A nuclease is an enzyme that cleaves the phosphodiester bonds of double-stranded DNA. An endonuclease cleaves internal phosphodiester bonds, while an exonuclease cleaves the phosphodiester bonds of terminal nucleotides. A restriction endonuclease, also referred to as a restriction enzyme, cleaves double-stranded DNA at or near a specific nucleotide sequence known as the restriction site. Restriction enzymes are isolated from most prokaryotes and are used by prokaryotes, such as bacteria, to break down or destroy foreign DNA. The DNA of the prokaryote is chemically modified at the restriction site in such a way that the restriction enzyme cannot cut it. (Naito et al. (1995) Science 267:897–899). Restriction enzymes are given a three letter designation, based upon the name of the species in which they occur, followed by a strain designation and/or a Roman numeral distinguishing different enzymes from the same species or strain. For example, EcoRI, is a restriction enzyme isolated from *Escherichia coli* (*E. coli*).

Most restriction enzymes recognize 6–8 base pair sequences of double-stranded DNA. These restriction sites have an inverted mirror plane in the middle such that the first half of the site is the reverse of the complement of the second half of the site as follows:

...ACTG CAGT...

...TGAC GTCA...

Sequences with this kind of symmetry are referred to as palindromic. The cuts made by an enzyme recognizing such a sequence are also made in an inverted mirror symmetric way. One of the most commonly used restriction enzymes of this type is EcoRI, which cuts within or near the restriction site shown below:

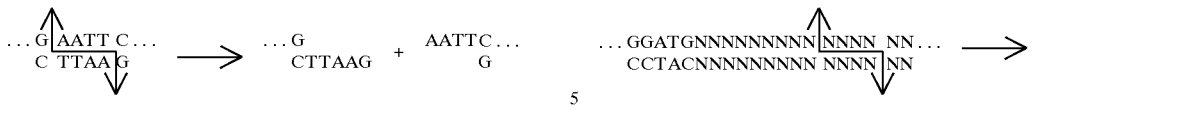

Enzymes with this symmetry are known as class II restriction enzymes of which over 1000 are known (Szybalski et al. (1991) Gene 100:13–26).

Some class II restriction enzymes cut both strands at the same site to generate flush or 'blunt ends', while other class II restriction enzymes make staggered breaks to generate single-stranded overhangs. These single-stranded overhangs are known as 'sticky' or 'coherent' ends, because a single-stranded overhang at the end of DNA cut by a restriction enzyme can form complementary base-pairs with a single-stranded overhang of a different piece of DNA cut by the same enzyme. The 'sticky ends' generated by a restriction enzyme make it possible to join two double-helical DNA fragments from different genomes by complementary base-pairing. When two such ends have annealed another enzyme, DNA ligase, can be added to permanently join the two ends and form a continuous piece of double-stranded DNA. DNA ligase catalyzes the formation of phosphodiester bonds. Restriction enzymes that make staggered cuts, such as EcoRI, together with ligases, provide a simple way to clone DNA by insertion into a plasmid, as illustrated in FIG. 5 and discussed below.

Referring to FIG. 5A, a single restriction site (EcoRI) in a plasmid is cut, using the restriction enzyme, EcoRI. The cut made by EcoRI is represented in a schematic way to emphasize that both of the single-stranded overhangs generated are identical and self-complementary. A fragment XY with two matching ends is then joined to the plasmid by complementary base-pair interactions and covalently linked with a DNA ligase. In this operation because both of the overhangs are identical, the fragment is nonorientable, and the reaction yields two products.

FIG. 5B illustrates that a fragment can be deleted from a plasmid if it is flanked by two restriction sites. In FIG. 5B, the fragment is the product of the insertion operation illustrated in FIG. 5A and is flanked by two restriction sites for the same enzyme. After deletion the solution is diluted until conditions favor cyclization and the plasmid DNA is recyclized without the XY fragment using a DNA ligase.

If a second restriction site, such as, BamHI, replaces one of the EcoRI restriction sites in FIG. 5A, then a double digest using EcoRI and BamHI excises an oligonucleotide XY with two different single-stranded overhangs (FIG. 5C). In this case, a fragment VW that has two different ends, can be inserted into the plasmid in an oriented manner yielding only one product.

A subgroup of class II restriction enzymes, the class IIS restriction enzymes do not recognize palindromic restriction sites. Additionally, this subgroup of enzymes cut away from their restriction sites in a stretch of arbitrary DNA. (See, Szybalski, et al (1991) Gene 100:13–26, for a review of class IIS restriction enzymes). One example of a class IIS enzyme is FokI, which cuts 10 nucleotides away from the sequence 5'-GGATG-3' and creates a single-stranded overhang of 4 nucleotides, referred to as the "width of the overhang" as illustrated below:

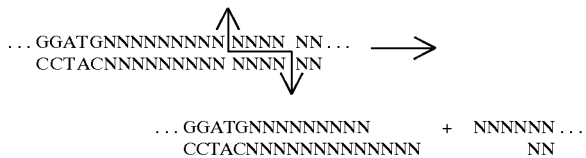

where N∈{A, C, G, T}, independently. These restriction enzymes are also known as nonpalindromic or asymmetric restriction enzymes. Class IIS asymmetric restriction enzymes offer several advantages over palindromic restriction enzymes as discussed below.

Since class IIS enzymes cut away from their restriction sites in a stretch of arbitrary DNA, single-stranded overhangs can be created that are neither identical nor self-complementary to each other. As a result an oligonucleotide C with ends matching the ends of the linearized plasmid can be inserted in only one orientation. (FIG. 6A). In FIG. 6A, the restriction site of FokI is represented by the FokI labeled arrow and its cutting site is represented by the arm extending from the restriction site. The ends created by FokI are drawn in a way which emphasizes that the single-stranded ends produced by the action of the enzyme are neither identical nor self-complementary. Additionally, unlike class II enzymes, which cut within the restriction site and thus generate only one kind of single-stranded overhang, defined by three variables—the length, sequence and polarity (5' or 3') of the overhang, one asymmetric restriction enzyme can be used to create many different single-stranded ends by varying the arbitrary 4 nucleotide sequence cut by FokI.

A pair of class IS restriction sites with opposite directions can be used to prepare two overhangs derived from different sequences, as illustrated in FIG. 6B. In this case, because neither the insertion oligonucleotide, nor the cut plasmid DNA have self complementary ends, the desired insertion reaction will compete with significantly fewer side reactions.

If two restriction sites occur adjacent to each other, as illustrated in FIG. 6C, they can be cut out of the plasmid and the plasmid can be rejoined without regeneration of a restriction site. Because the cleavage sites of Class II restriction enzymes occur within their restriction sites the ligation of the overhangs created necessarily results in the regeneration of the original restriction sites.

Combining the operations illustrated in FIGS. 6B and 6C, a fragment of DNA can be inserted into the plasmid and the restriction site excised, if two back to back restriction sites are used to prepare overhangs derived from different cleavage site sequences as illustrated in FIG. 6D.

BRIEF SUMMARY OF THE INVENTION

The present invention describes a universal molecular DNA Turing machine. The Turing machine of the present invention is encoded with oligonucleotides and transitions are effected using restriction enzyme chemistry. The present invention also includes a method for operating the universal molecular DNA Turing machine of this invention. A total of six distinct chemical steps are repeated to simulate any given Turing machine. All of the reagents used are commercially available and all of the chemical operations are routinely performed by molecular biologists. Using this method a Universal Turing machine capable of simulating any Turing machine and hence any algorithm can be constructed.

Specifically, the Turing machine of this invention consists of a singular circular DNA molecule, which embodies the head of the Turing machine, the state of the finite control, and the contents of the tape. The head of the Turing machine consists of two back to back asymmetric restriction sites, referred to as the invariant restriction site and the state restriction site, and the spacing between the state restriction site and the current symbol encodes the state (q) of the Turing machine. The transition table is encoded by transition oligonucleotide inserts, that encode the new state, symbol and direction of the machine. Transitions from one state to the next are effected using a series of restrictions and ligations, in which the tape is cut with restriction enzymes, the transition oligonucleotide is inserted with a DNA ligase and the previous symbol is then eliminated from the tape using a second restriction enzyme.

Also included in the present invention is a method of operating a DNA based Universal molecular Turing machine. A total of 6 distinct chemical steps are repeated to take an ID at time T to an ID at time T+1. These steps are set forth in FIG. 13 and FIG. 20. In steps 1 through 4 a transition nucleotide encoding the new state, symbol and direction of the Turing machine is inserted into the DNA tape in a process analogous to that shown in FIG. 6D. In steps 5 and 6 the previously read symbol is deleted from the tape using the concept of progress described in FIG. 8. Steps 1 through 6 are repeated until a Halt sequence is incorporated into the tape and the computation is completed. After any step 6, the computation may be checked for the incorporation of a Halt sequence. This is accomplished by PCR amplification of a small aliquot of the computation using the Halt sequence as a primer. Only halted tapes are amplified and if detected they are sequenced to recover the answer to the problem.

The Turing machine of the present invention can be operated to solve only one problem, in which case every DNA molecule/tape is identical and encodes the same computation. The Turing machine of the present invention can also be operated to solve more than one problem simultaneously. In this case there are a number of different DNA molecules/tapes, each of which encodes a separate computation.

As stated above, all of the reagents used are commercially available (New England Biolabs, Beverly, Mass.) and all of the chemical operations are routinely performed by molecular biologists.

In non-limiting examples of the present invention, the present inventors establish that the molecular Turing machine of this invention can implement a 4×7 Universal Turing machine and a BB-3 Turing machine.

BRIEF DESCRIPTION OF THE FIGURES

FIG. 5 illustrates various operations on a plasmid using a class II endonuclease. FIG. 5B illustrates deletion of a DNA fragment from a plasmid. FIG. 5C illustrates insertion of a DNA fragment VW into a plasmid with orientation control.

FIG. 6A illustrates insertion of a DNA fragment C with orientation control. FIG. 6B illustrates excision of a DNA fragment C, followed by insertion of a DNA fragment D. FIG. 6C illustrates excision of the restriction site from the plasmid. FIG. 6D illustrates excision of the restriction site from the plasmid, followed by insertion of a DNA fragment D.

FIG. 9 also illustrates the two possible DNA representations generated for any particular ID. In FIG. 9A, the head of the Turing machine is positioned to the right of the current symbol and in FIG. 9B, the head of the Turing machine is positioned to the left of the current symbol.

FIGS. 14A–14D show a DNA and schematic representation of the White and Black symbols and the left and right invariant sequences of the BB-3 implementation of the DNA Turing machine. In FIG. 14A the Black and White symbols are shown schematically. In FIG. 14B the Black and White symbols are illustrated schematically with the left and right invariant sequences included. FIG. 14C illustrates schematically, a WBW sequence, including the invariant sequences. FIG. 14D shows the actual DNA sequences (SEQ ID NOs: 4 and 5) for the White and Black symbols and the left and right invariant sequences.

FIG. 17 shows the actual DNA sequences (SEQ ID NOs: 6–17 of the overhangs of FIG. 16, when the Black and White symbols are cut by the state cutter enzyme FokI.

FIG. 19 depicts the restriction enzymes and the corresponding DNA sequences ( SEQ ID NOs: 18–23) of the restriction sites, assigned to the various restriction sites depicted in FIG. 18.

FIG. 23 depicts the DNA sequences (SEQ ID NOs: 28–31) used as symbols in the implementation of Minsky's universal Turing machine.

FIG. 24 depicts the transition table for Minsky's 4×7 Universal Turing Machine.

DETAILED DESCRIPTION OF THE INVENTION

This invention includes a DNA based universal molecular Turing machine. The Turing machine of the present invention is encoded with oligonucleotides and transitions are effected using restriction enzyme chemistry. The variable elements of the Turing machine—the head position, the state of the finite control, and the contents of the tape—are embodied in a single circular DNA molecule. The transition table is encoded by transition oligonucleotide inserts. Transitions from one state to the next are effected using a series of restrictions and ligations.

Specifically, the head of the Turing machine consists of two back to back asymmetric restriction sites, referred to as the invariant (Inv) and the State (q) restriction sites. As explained above (FIG. 6D), using back to back restriction sites, a fragment of DNA can be inserted into a plasmid and the restriction site excised. The spacing between the state restriction site and the current symbol encodes the state (q) of the Turing machine. The transition table is encoded with transition oligonucleotides, which are inserted into the DNA tape. The transition oligonucleotides encode the new state, symbol, and direction of the Turing machine into the DNA tape. As explained in detail below, there are four basic types of transition nucleotides.

As stated above, transitions from one state to the next are effected using a series of restrictions and ligations. The restrictions are performed using Class II restriction endonucleases. In a preferred embodiment, a subgroup of the class II restriction endonucleases, the asymmetric or class IIS restriction enzymes, are used to effect transitions. Ligations are performed with DNA ligases.

Figure 13:
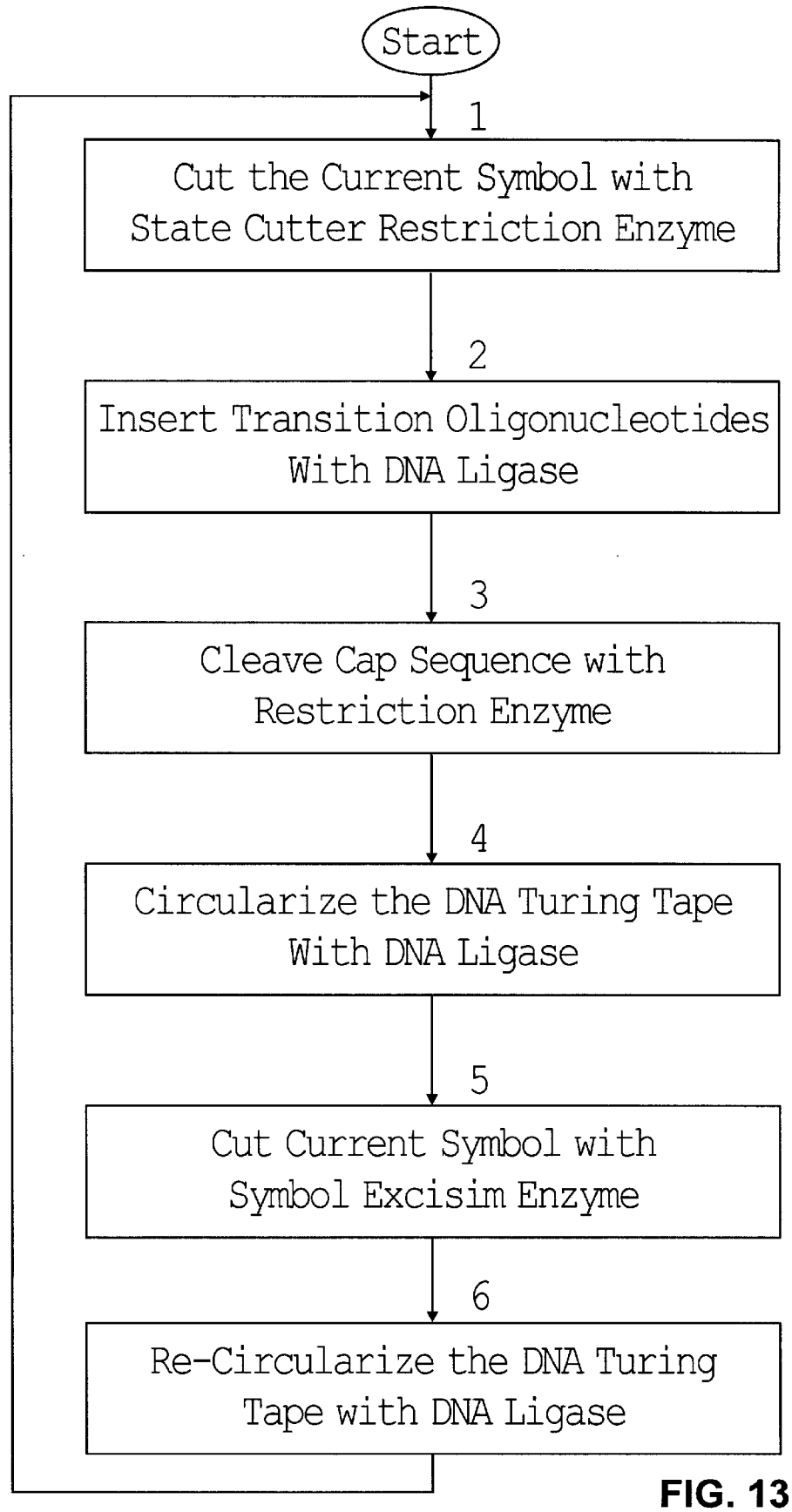
FIG. 13 is a flow diagram of the process of operating a molecular Turing Machine.

Also included in this invention is a method of operating the DNA based universal molecular Turing machine of this invention. A total of 6 distinct chemical steps are repeated to take an ID at time T to an ID at time T+1. These steps are set forth in FIG. 13. In steps 1–4, a transition nucleotide is inserted into the DNA tape in a process analogous to that shown in FIG. 6D and in steps 5 and 6 the previously read symbol is deleted from the tape. Briefly, the current symbol is cut with the state restriction enzyme, a transition oligonucleotide, encoding the new state, symbol and direction of the Turing machine, is inserted with a DNA ligase and the plasmid is recyclized. Following, cyclization the current symbol is cut with a second restriction enzyme and the DNA tape is again recyclized. Steps 1–6 are repeated until a Halt sequence is incorporated into the tape and the computation is completed. It should be noted that the DNA remains double-stranded at each timestep, which as stated above is more stable to degradation than single-stranded DNA. Additionally, this eliminates the extra steps of melting and reforming double-stranded DNA with DNA polymerase. After any step 6, the computation may be checked for the incorporation of a Halt sequence. This can be accomplished by PCR amplification of a small aliquot of the computation using the Halt sequence as a primer. Only halted tapes are amplified and if detected they are sequenced to recover the answer to the problem.

The DNA based Turing machine of this invention may be used to implement, among others, a Busy Beaver Turing machine and a 4×7 Universal Turing machine.

Figure 7:
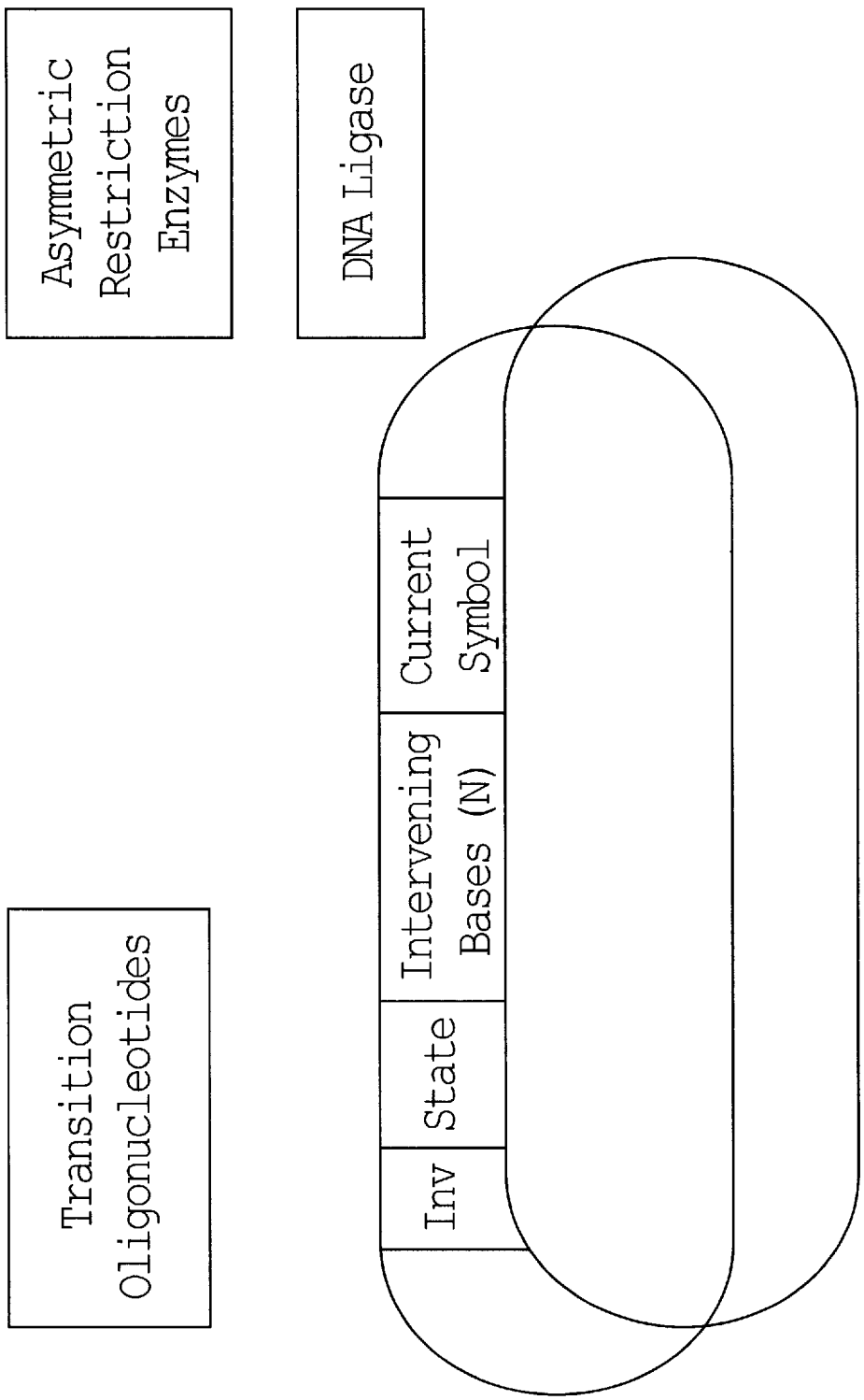
FIG. 7 is a schematic drawing of the molecular Turing machine of this invention.

The molecular Turing machine of this invention is depicted in FIG. 7. The variable elements of the Turing machine (the head position (Inv and State (q)) restriction sites, the state of the finite control (distance between state restriction site and current symbol, and the contents of the tape) are embodied in a single circular DNA molecule. The transition table is encoded by transition oligonucleotides that encode the new state, symbol and direction of the Turing machine into the DNA tape. The transitions of the Turing machine are effected using class II restriction enzymes and DNA ligases. The six chemical steps that apply the oligonucleotide encoded transition table to advance the Turing machine one time step are described in detail below.

Certain terms and abbreviations used to describe the invention herein are defined as follows:

"Asymmetric restriction enzyme" means a Class II or Class IIS restriction enzyme. Class IIS restriction enzymes include, but are not limited to BbvI, FokI, BseRI, BsrDI, HgaI and BpmI. The restriction sites for each of these enzymes are set forth in FIG. 19.

"Cutting frame" refers to the site at which the symbol is cut by the Class II restriction enzyme.

"DNA ligase" refers to any enzyme which catalyzes the formation of phosphodiester bonds between the 3'-OH end of one ssDNA strand and the 5'-phosphate end of the same or another ssDNA strand.

An "invariant sequence" (Inv) refers to a sequence located either to the left or the right of the symbol sequence. When cut by the invariant enzyme an end is created that is distinct from any end reacted by the state cuter enzyme.

Figure 8:
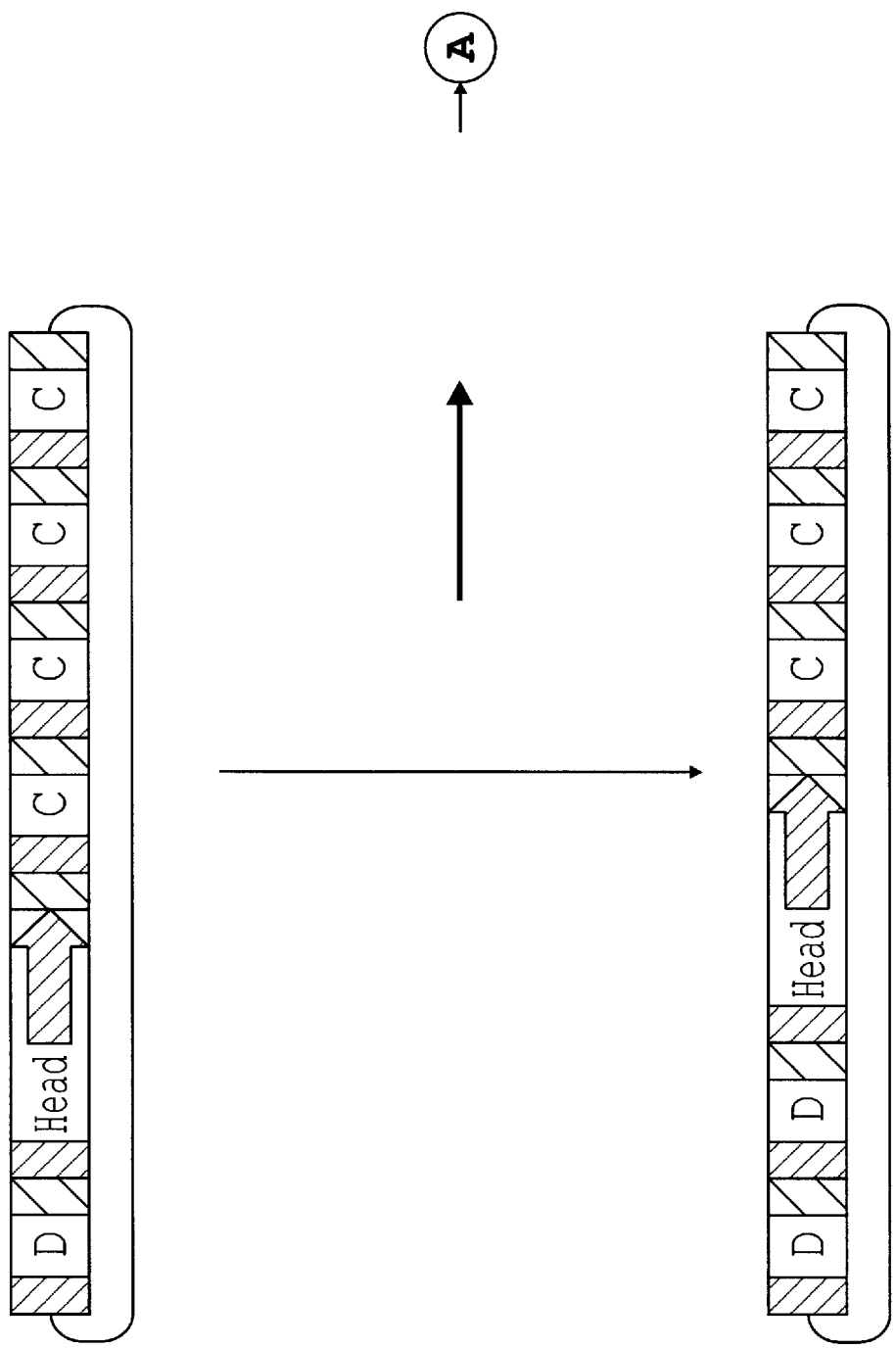
FIG. 8 is a schematic drawing of a plasmid illustrating the "progress" or movement of a sequence through a strand of DNA.
Figure 8:
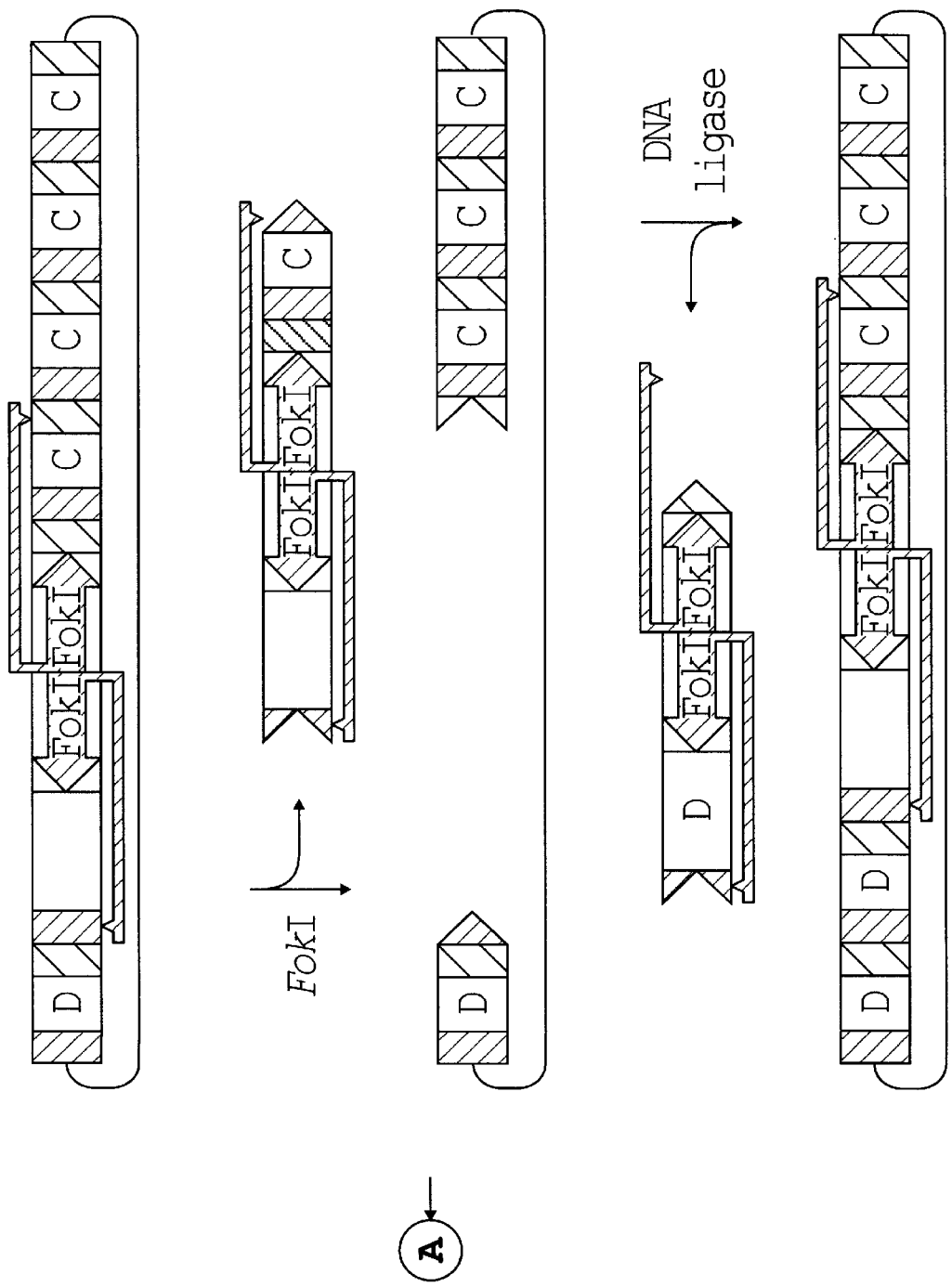

"Progress" refers to movement of a sequence through a strand of DNA. FIG. 8 illustrates what is meant by "progress". A sequence head moves to the right through a string of C sequences and replaces them with D sequences (similar to the head of a Turing machine). The right half of the figure demonstrates how two back to back occurrences of the FokI restriction site can be used to move such a head sequence. This operation is a variation of the operation illustrated in FIG. 6D, in which a pair of back to back restriction site have been added to the right of sequence D in the insert, subject to the constraint that the right most restriction site has a cleavage site that does not lie entirely in the insert.

The term "state cutter enzyme" refers to the Class II restriction enzyme used to cut symbol sequences.

"Transition oligonucleotides" are oligonucleotide inserts which encode the new state, symbol, and direction of the Turing machine into the DNA tape.

With reference to FIG. 7, the Turing machine of this invention is described in detail below.

Symbols.

Figures 9A, 9B:
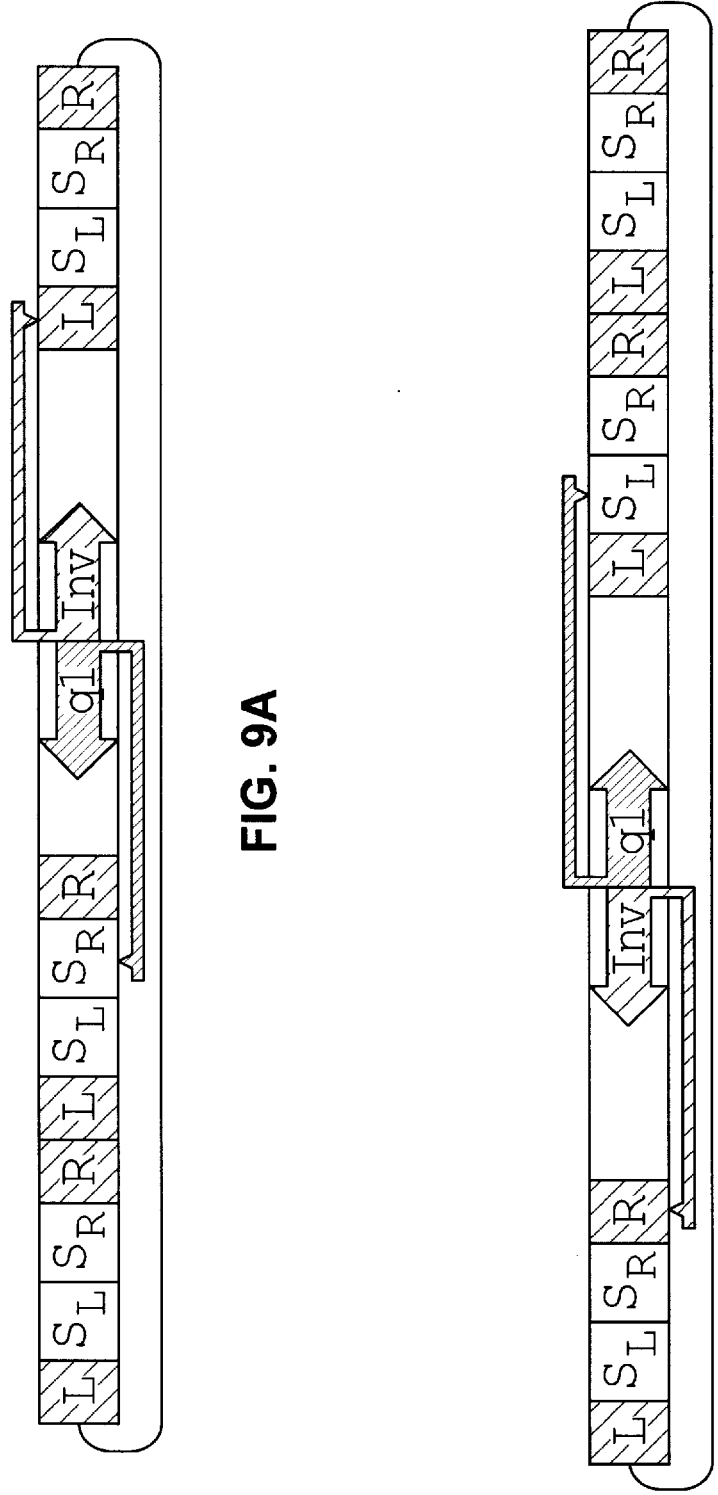
FIGS. 9A and 9B are schematic drawing of the Turing machine of this invention depicting the head, symbols and invariant sequences.

Distinct DNA sequences are used to define each symbol (S). Each sequence is subdivided into a left and right half ($S_L$ and $S_R$). A short sequence is appended on both the left and right side of each symbol. These sequences are the same for all of the symbols and are thus referred to as the left (L) and right (R) "invariant sequences" (See FIG. 9). As discussed below the invariant sequences enable the excision of the last symbol, independent of the symbol.

The Head of the Turing Machine.

The two back to back asymmetric restriction sites labeled Inv and State (q1) represent the head of the Turing machine. (FIG. 9). As explained above (FIG. 8), when using back to back restriction sites, a head sequence can be made to "progress" through a strand of DNA similar to the head of a Turing machine. The restriction site labeled with the state (q1), referred to hereinafter as the state restriction site, always points to the current symbol and the restriction site labeled Inv always points at an adjacent invariant sequence.

Because the head of the tape is placed "inside" of the tape, two possible DNA representations are generated for any particular ID. In one representation (FIG. 9A) the head sequence of the Turing machine is positioned to the right of the current symbol, and in the other representation (FIG. 9B) the position of the head sequence is positioned to the left of the current symbol. If the head sequence is to the right of the current symbol then the last move of the machine was to the left; conversely, if the head sequence is to the left of the current symbol then the last move of the machine was to the right.

The State of the Turing Machine.

The spacing between the state restriction site and the current symbol encodes the state of the Turing machine. For example, consider the 6 base pair oligonucleotide $W_L$, the first half of the symbol W, shown below:

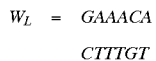

The 5 base pair restriction site of FokI (GGATG) may be used to cut sequence $W_L$ at three different sites, referred to as cutting frames, by varying the number of intervening nucleotides (N) between the FokI restriction site and the symbol sequence. (See FIGS. 10A–10C). As stated above FokI cuts 10 nucleotides away from the sequence 5'-GGATG-3' and creates a single-stranded overhang of 4 nucleotides.

Figure 10:
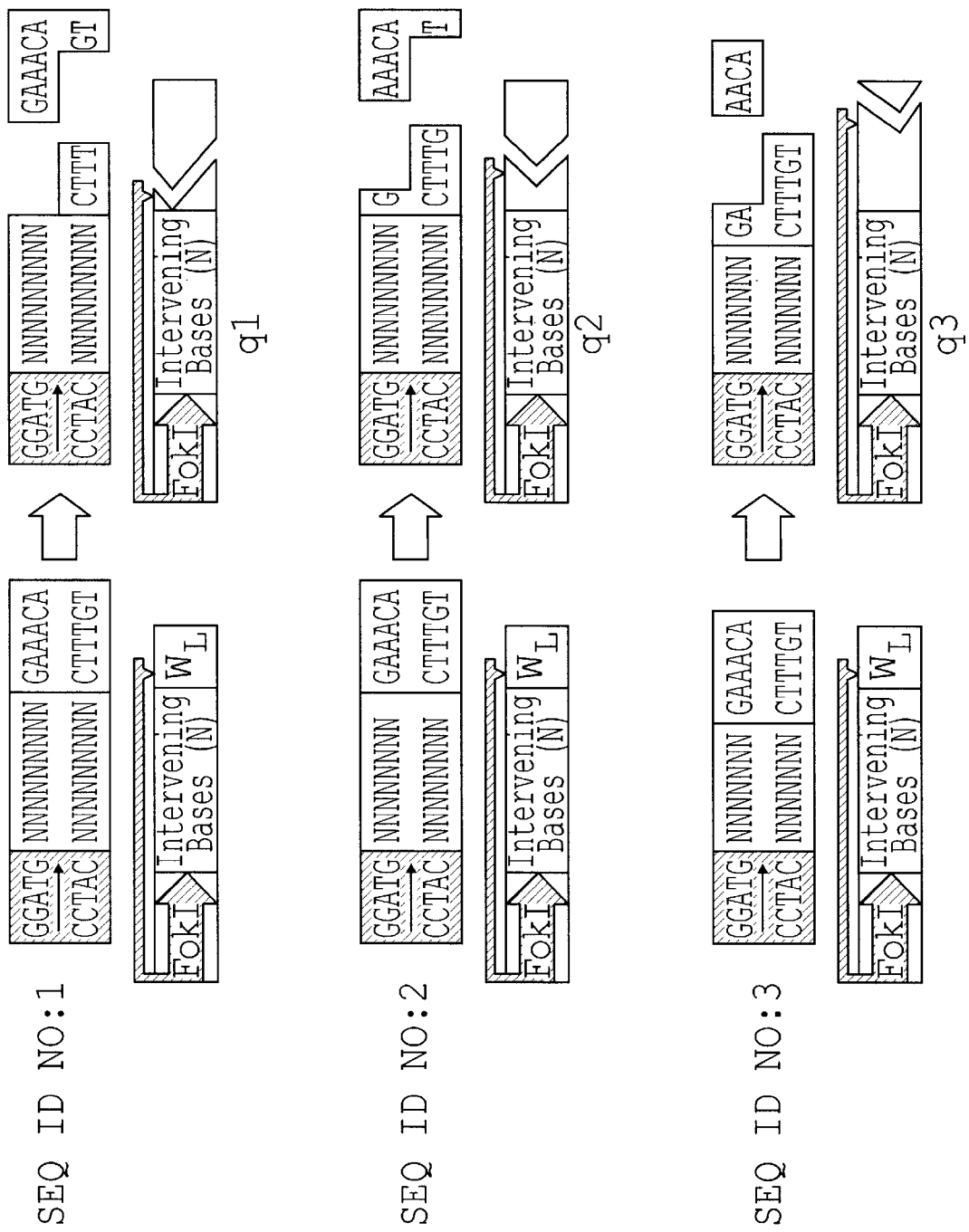
FIG. 10 is a DNA and a schematic representation of FokI cutting a six base pair sequence, $W_L$, in at least three different sites, referred to as cutting frames SEQ ID NOs: 1–3.

The frame in which a symbol sequence is cut corresponds to the concept of the state of the Turing machine. Thus, the state of the machine in FIGS. 10A–10C is q1, q2 and q3, respectively. The enzyme used to cut symbol sequences in different frames is referred to as the state cutter enzyme. Each half of a symbol sequence is designed to be large enough to be cut into three frames by a state cutter enzyme. Thus, each symbol can be used to generate 6 different states. By carefully picking different DNA sequences for each symbol, the single-stranded overhangs generated by cutting a given symbol in a given reference frame can be made unique.

Encoding the Transition Table.

The unique single-stranded overhangs generated by cutting a symbol with a state cutter enzyme enables the ligation of a transition oligonucleotide into the DNA tape. The transition oligonucleotide encodes the new state, symbol, and direction of the Turing machine into the DNA tape. At any given time step a Turing machine's last move may have been to the right or the left, and its next move may be to the right or left. This results in four basic types of transition nucleotides as described below (see FIGS. 11 and 12).

Figure 11:
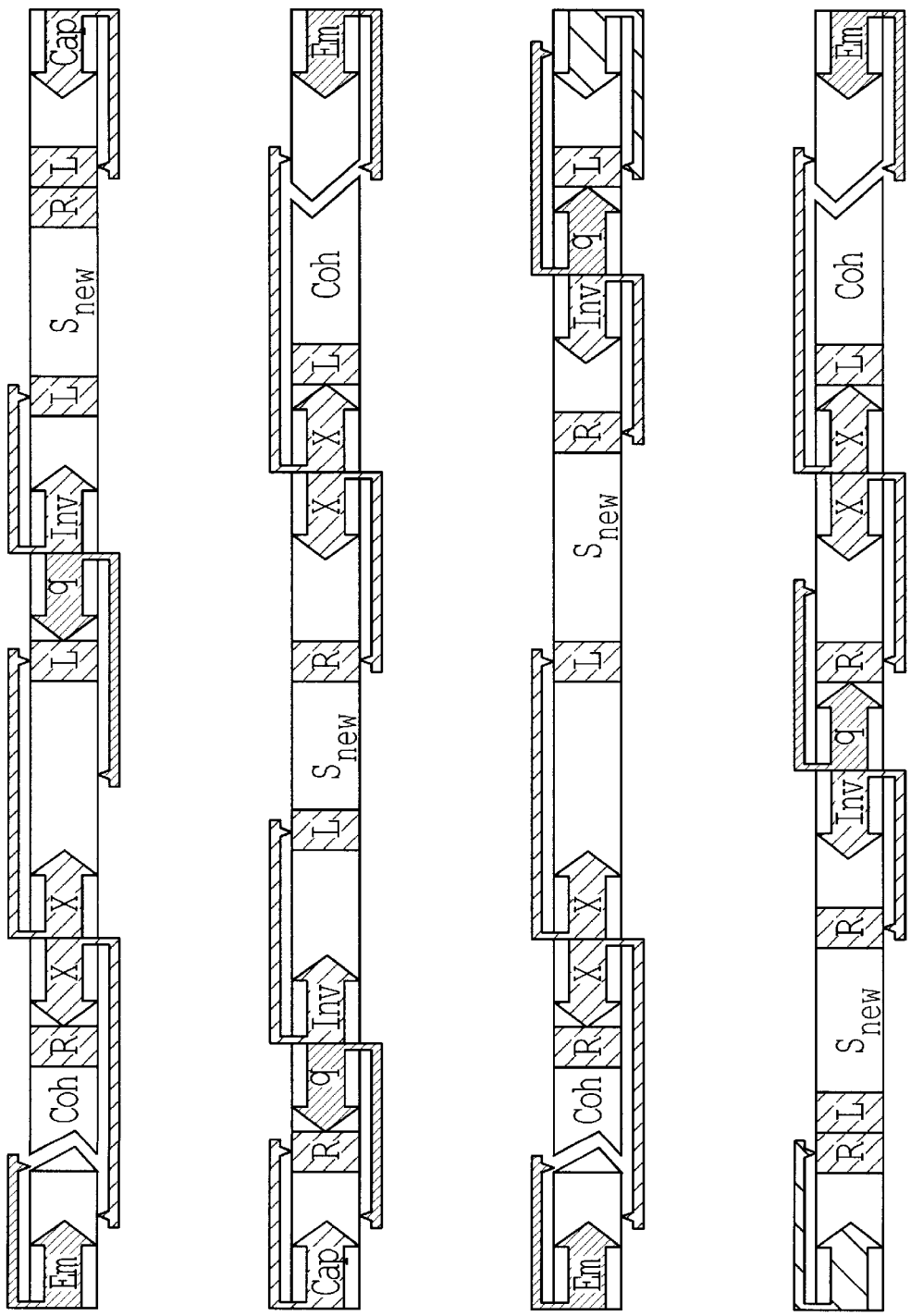
FIG. 11 is a schematic representation of the four kinds of transition oligonucleotides.

Referring to FIG. 11:

Coh designates the single-stranded end which is complementary to the single-stranded end generated by cutting a given symbol with the state cutter enzyme.

Em designates the restriction site for the end-maker restriction enzyme. The end-maker restriction enzyme cuts the transition oligonucleotide to create the same size and orientation overhang as the state restriction enzyme (q), but it has a distinct recognition site. In other words, because the state restriction site (q) is already incorporated within the transition oligonucleotide, another enzyme which creates the same cut as the state restriction enzyme, but has a distinct recognition site, is required to create the cohesive end necessary to join the oligonucleotide to the tape. This site allows the cohesive end of the transition oligonucleotide to be prepared in the presence of in the presence of the state reaction site by cleavage with the end-maker enzyme and is used only in the manufacture of the transition oligonucleotides.

$S_{new}$, is the oligonucleotide sequence encoding the new symbol.

Cap, X and Inv are class IIS restriction sites whose enzymes cleave the left (L) and right (R) invariant sequences to give the same size and orientation overhang. These sites are used to cleave the invariant sequences at various stages of the computation. Cap is a restriction site recognized by the cap enzyme, Inv by the invariant enzyme, and X by the symbol-excision enzyme.

Figure 1:
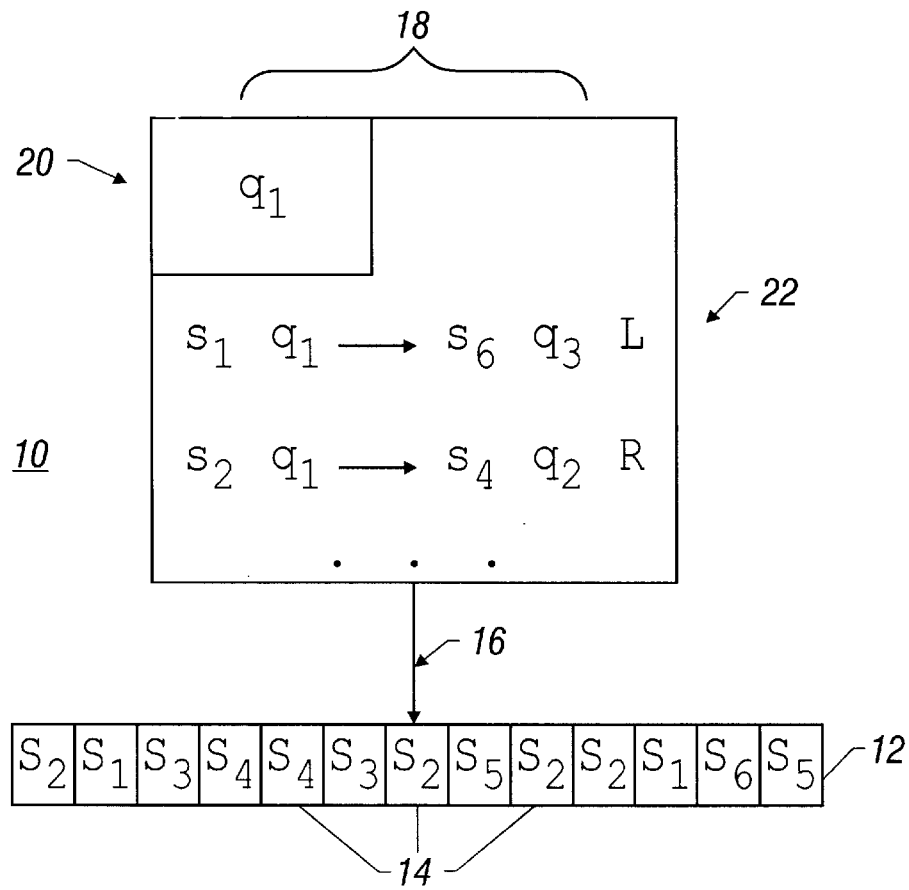
FIG. 1 is a schematic drawing of a prior art Turing machine operating on its tape.

After being cleaved with an end-maker enzyme to remove the Em sequences, each transition nucleotide can be divided into five sections: Coh which is the single-stranded overhang specific to a particular state-symbol combination, the head sequence (State+Inv), the new symbol ($S_{new}$) which is being inserted into the DNA tape, the symbol excision sites X, and the Cap sequences. Coh matches the single-stranded overhang of the symbol cut during the last timestep by the state cutter enzyme. If the machines last move was to the left, Coh is on the left end of the transition oligonucleotide and if the machines last move was to the right Coh is on the right hand end of the transition oligonucleotide. (See FIGS. 11 and 12). The symbol-excision sites X are always placed next to Coh and Cap is placed on the opposite end of the oligonucleotide. The head of the machine (State and Inv) and the new symbol are positioned between the X and Cap sequences. The State site in the head sequence points in the direction that the head sequence will move. The new symbol ($S_{new}$) is placed "behind" the head sequence, that is, next to Inv. Therefore, the transition oligonucleotide of FIGS. 11-1 and 12-1, indicate that the last move of the machine was to the left and the next move of the machine will also be to the left. The transition oligonucleotide of FIGS. 11-2 and 12-2 indicate that the last move was to the right and the next move will be to the left.

Figure 20:
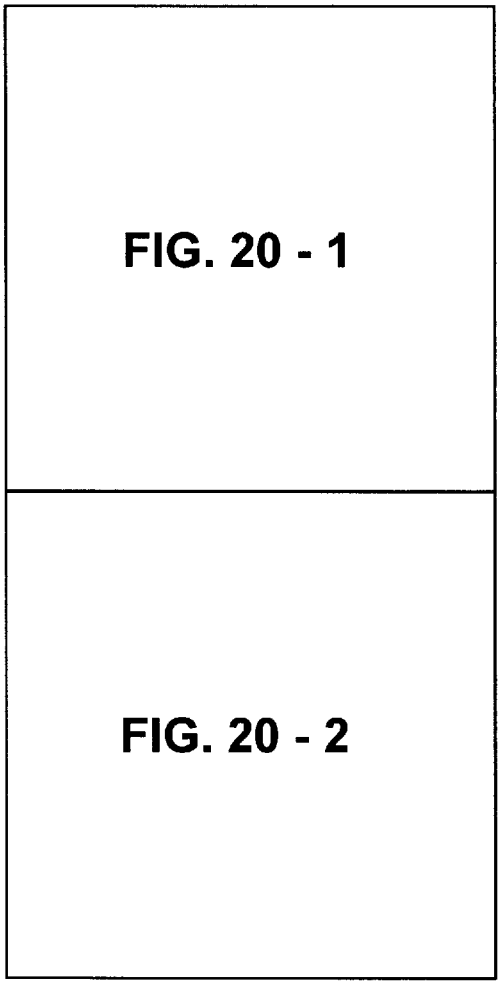
FIG. 20 depicts schematically the transition of a BB-3 Turing machine at T=0 to T=1.
Figures 1, 20:
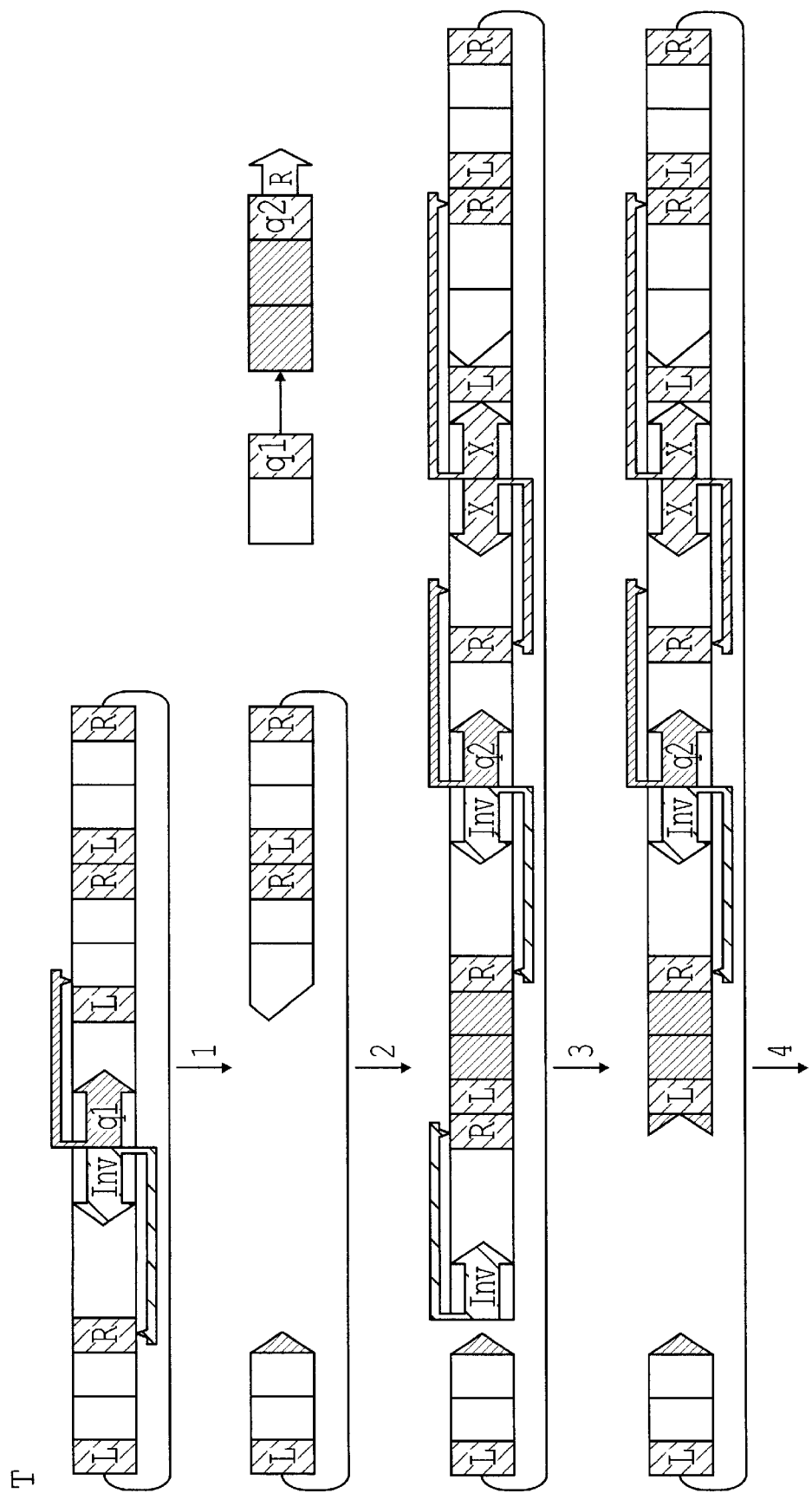
Figures 2, 20:
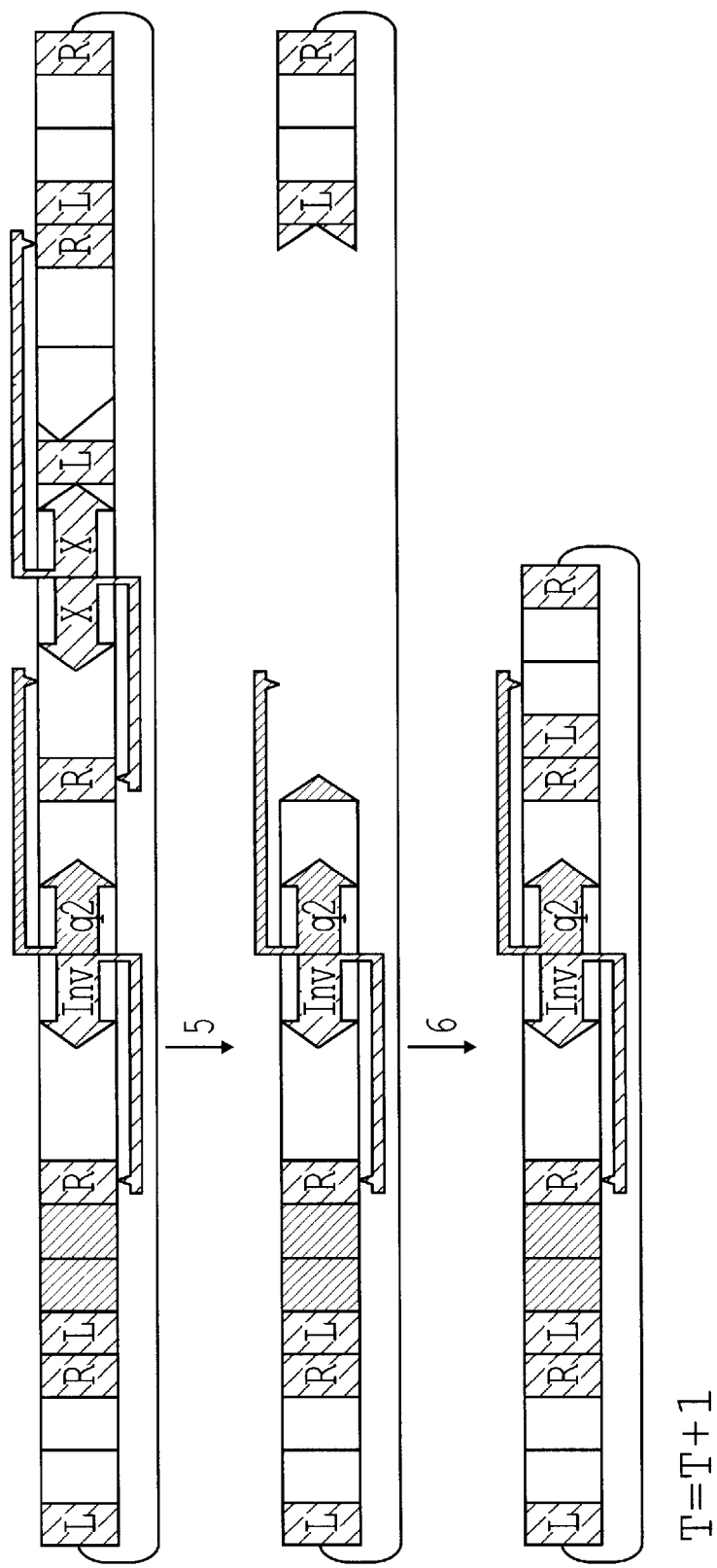

The number of nucleotides (N) between a given state cutter recognition site and the adjacent invariant sequence R or L (referred to as the "whitespace") differs between an oligonucleotide encoding a change of direction and an oligonucleotide encoding a preservation of direction. As can be seen in FIG. 20 when the Turing machine moves in the same direction (FIG. 20 (T=T+1)) there are two invariant sequences between the state sequen and the current symbol sequence. If the Turing machine changes direction, however, (FIG. 20, (T)) there is only one invariant sequence between them. To make the spacing work out, a spacer of a few nucleotides (N) is added to the transition oligonucleotides which encode a move in the same direction.

Making a Transition.

Six chemical steps are required to take an ID at time T to an ID at time T+1. These steps are set forth in FIG. 13 and FIG. 20. Steps 1–4 replace the head with the correct transition oligonucleotide in a process analogous to that shown in FIG. 6D. Steps 5 and 6 delete the previously read symbol from the tape using the concept of progress described with respect to FIG. 8.

In step 1, the current symbol is cut with the state and invariant restriction enzymes. This may be performed in one reaction or in two sequential reactions depending on the state and invariant enzymes used. The single-stranded overhang created by the state cutter enzyme is specific for the current symbol and state combination and is complementary to an oligonucleotide encoding the transition to the next symbol state and direction. The invariant cutting enzyme cleaves an invariant sequence to create an end that is the same regardless of what symbols lie to the left of the computation.

In step 2, the transition oligonucleotide encoding the next symbol and state is inserted into the DNA Turing tape with DNA ligase. In step 3, the Cap sequence is cleaved with the Cap restriction enzyme. Some restriction enzymes have difficulty cutting restriction sites near the ends of oligonucleotides. For this reason a few nucleotides may have to be added to the end of the Cap sequence. In step 4, the DNA is cyclized with DNA ligase. In steps 5 and 6, the previously read symbol is deleted from the tape using the concept of "progress" defined above (FIG. 8). In step 5, the DNA tape is cut with a symbol-excision restriction enzyme. This cuts away the previous symbol and leaves two matching invariant ends. In step 6, the DNA is recyclized with DNA ligase to join the invariant ends created in step 5. As can be seen in FIG. 20, the invariant sequences enable excision of the prior symbol and recyclization of the DNA, independent of the symbol that is being excised. This simplifies the process considerably in that only one end of the transition oligonucleotide is specific to the state and symbol and thus has to be unique.

Steps 1–6 are repeated until a Halt sequence is incorporated into the tape and the computation is completed. A Halt sequence is a random oligonucleotide comprised of at least 20 nucleotides. In a preferred embodiment the Halt sequence is comprised of 40 nucleotides. At least one of the transition nucleotides contains a Halt sequence. The Halt sequence is incorporated into the tape when the computation is complete. After any step 6, the computation may be checked for the incorporation of a Halt sequence. This can be accomplished by PCR amplification of a small aliquot of the computation using the Halt sequence as a primer. Only halted tapes are amplified and if detected they can be sequenced to recover the answer to the problem. This scheme works well, only if all of the DNA tapes perform the same computation, however if different tapes include different problems some unfinished tapes will be lost every time the computation is checked for Halt sequences. This problem may be alleviated by incorporating biotin, a functional group that binds strongly to streptavidin, into the Halt sequence. Streptavidin coated beads can then be used to recover halted machines prior to PCR amplification. Since only halted tapes would bind to the streptavidin beads, no portion of the unfinished tapes would be removed. These steps are described in more detail below with reference to a BB-3 Turing Machine.

DNA prototype of a BB-3 Turing Machine. The DNA based Turing machine described above has been used to implement a BB-3 Turing machine as described below.
Symbols.

Referring to FIG. 14, two distinct DNA sequences are used to represent the symbols W and B (FIG. 14A). As discussed above each sequence is subdivided into a left and right half ($W_L$ and $W_R$, $B_L$ and $B_R$) and a short sequence (invariant sequence) is appended on both the left and right side of each symbol (labeled L and R, respectively) (FIG. 14B). The Turing tape (without the head) holding the string WBW is shown schematically in FIG. 14C. FIG. 14D shows illustrative DNA sequences for the B, W and invariant (Inv) sequences.
The Head of the Turing Machine.

Figure 15A:
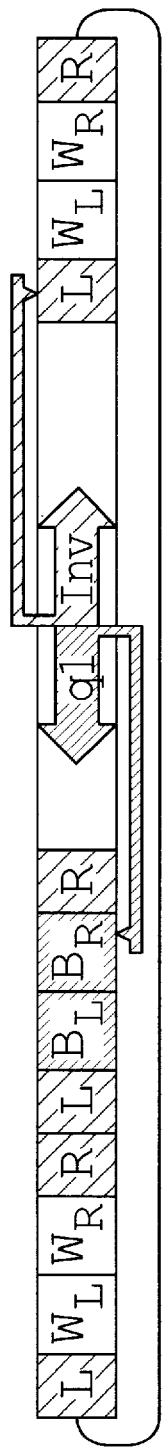
FIGS. 15A–15B illustrate the two ways to encode an ID of a DNA encoded BB-3 Turing machine.
Figure 15B:
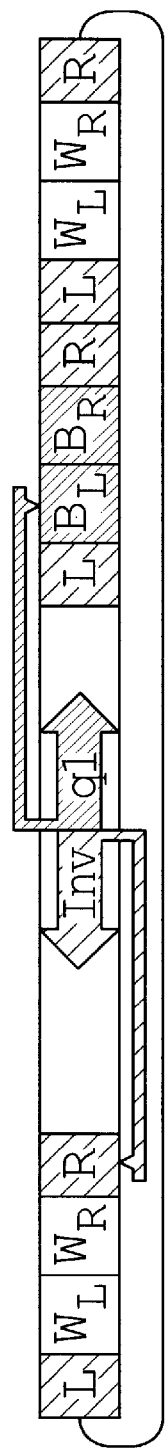

The two back to back asymmetric restriction sites labeled Inv and q1 (State) in FIGS. 15A and 15B represent the head of the Turing machine. As stated above, the state restriction site always points to the current symbol and the invariant restriction site always points to the adjacent invariant sequence.

Encoding an Instantaneous Description (ID).

FIGS. 15A and 15B, illustrate the two ways to encode an instantaneous description of a DNA encoded BB-3 TM in which the tape holds the string WBW, the head points at the symbol B, and the machine is in state q1. In FIG. 15A the head is to the right of the current symbol, indicating that the last move of the machine was to the left. In FIG. 15B the head is to the left of the current symbol, indicating that the last move of the machine was to the right.
The State of the Turing Machine.

Figure 16:
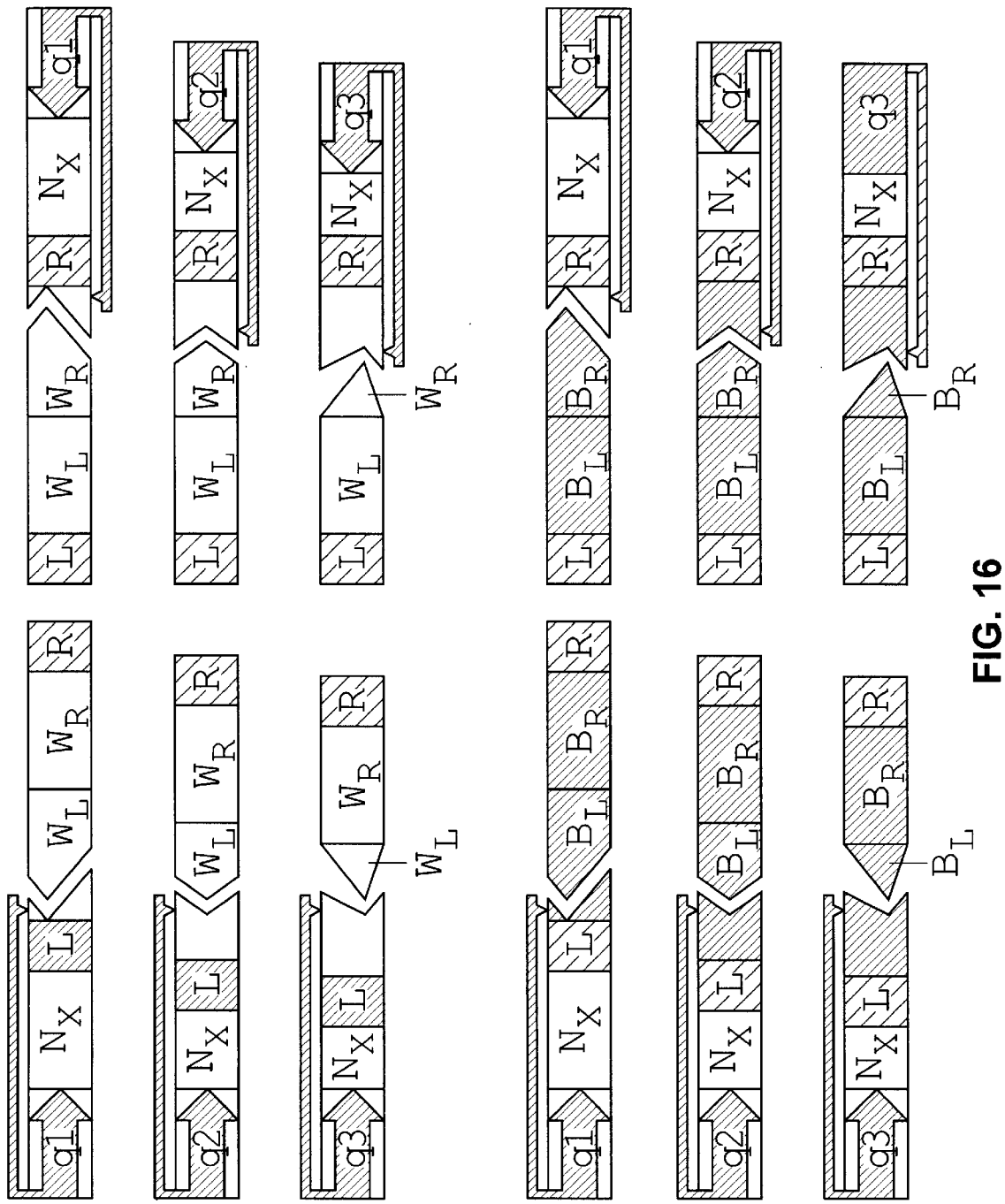
FIG. 16 is a schematic drawing of the black and white symbols showing the overhangs generated when the symbols are cut by a state cutter enzyme at three different sites from both the left and the right. $N_x$, refers to the intervening nucleotides (N).
Figure 17:
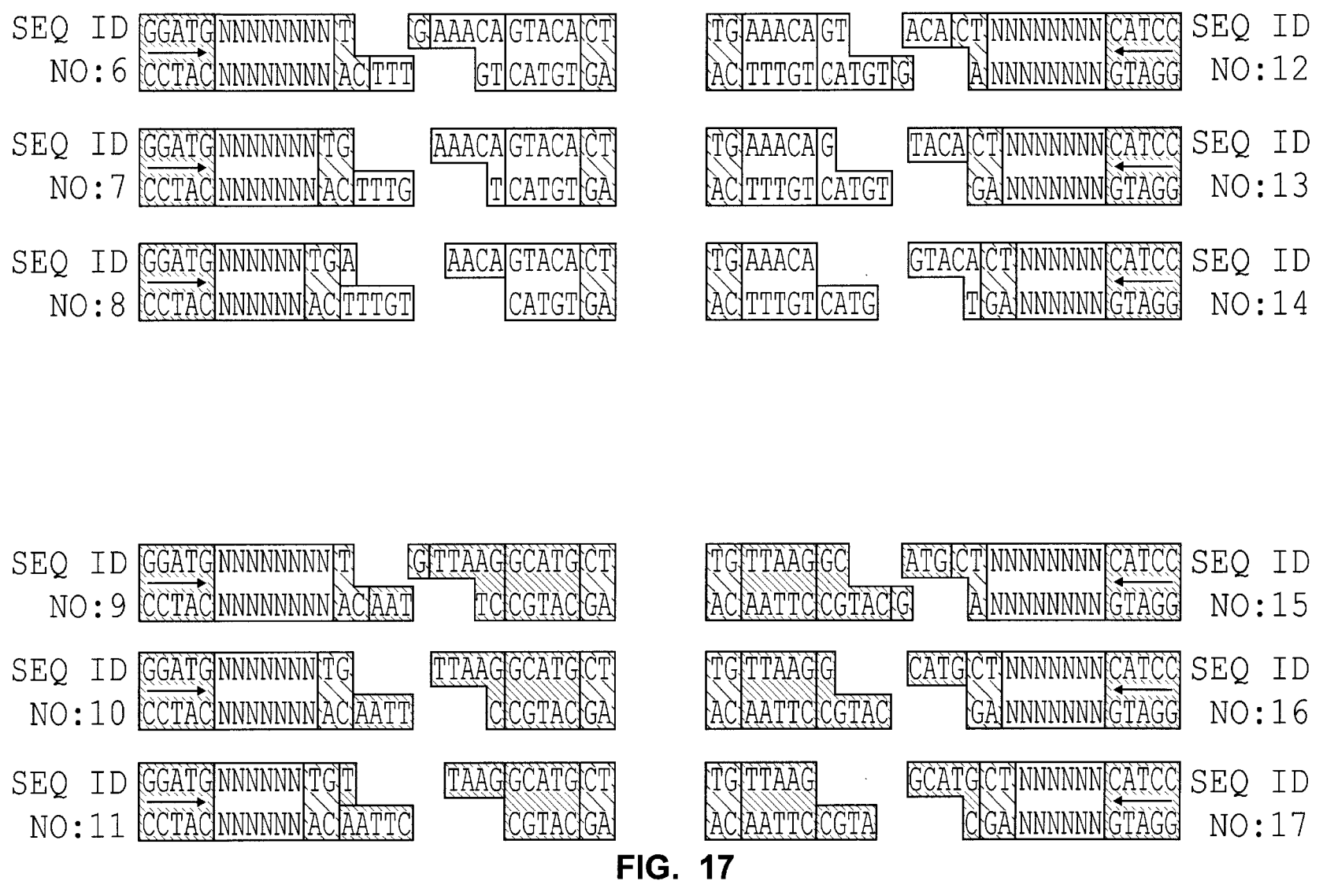
Figures 1, 18A:
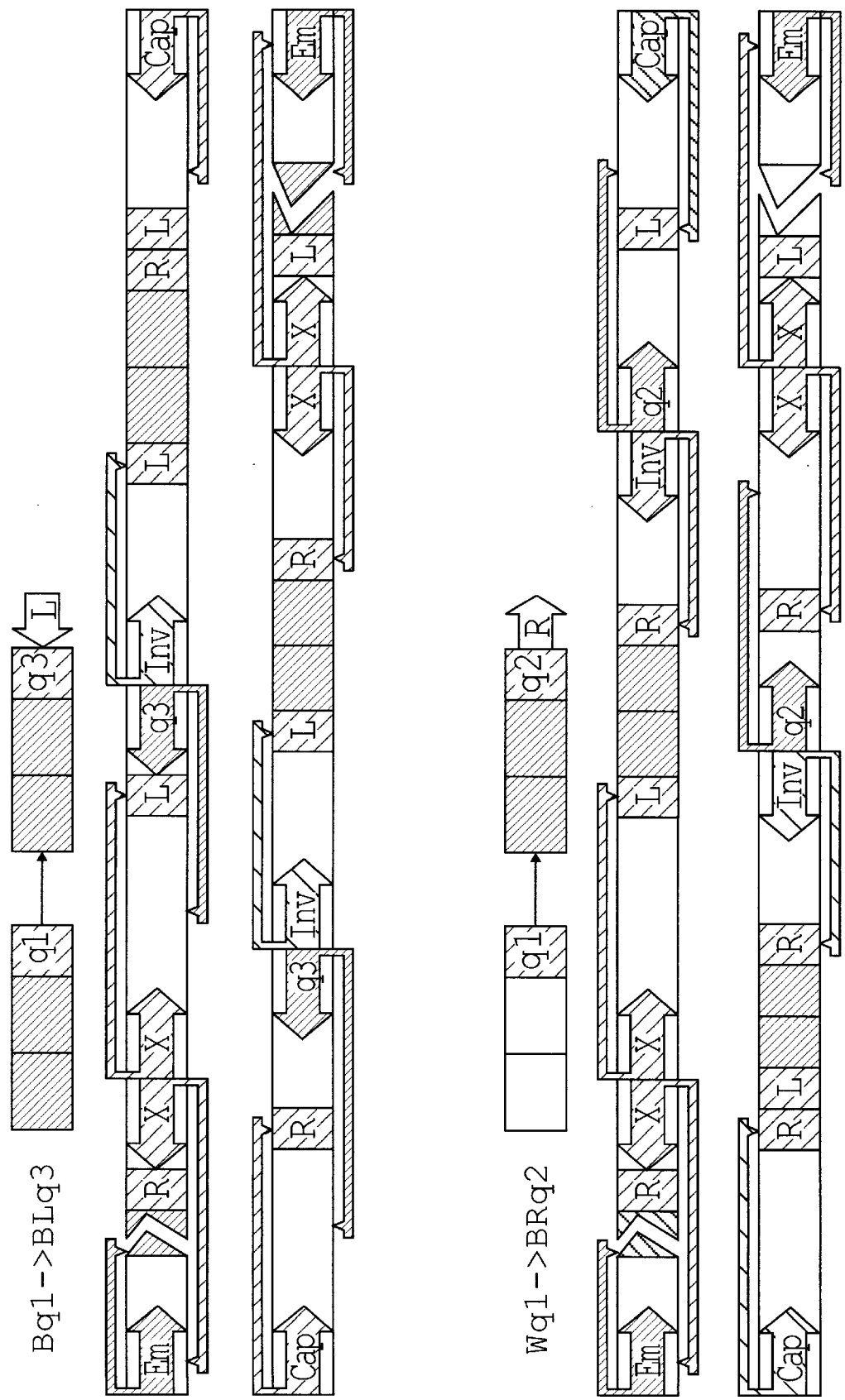
FIGS. 18A–18B are schematic representation of the twelve transition oligonucleotides for a busy beaver implementation of a molecular Turing Machine.
Figures 2, 18A:
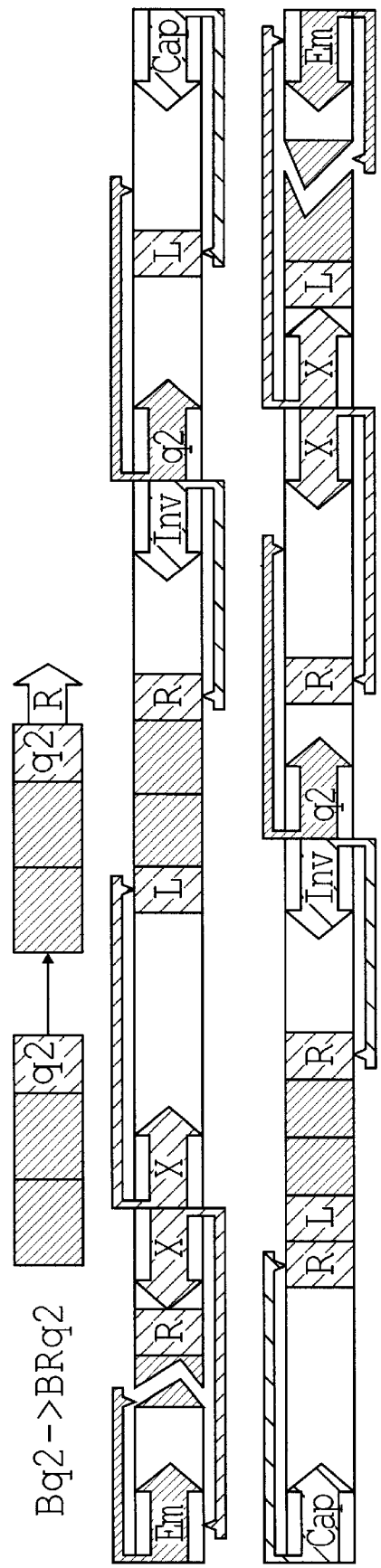
Figures 1, 18B:
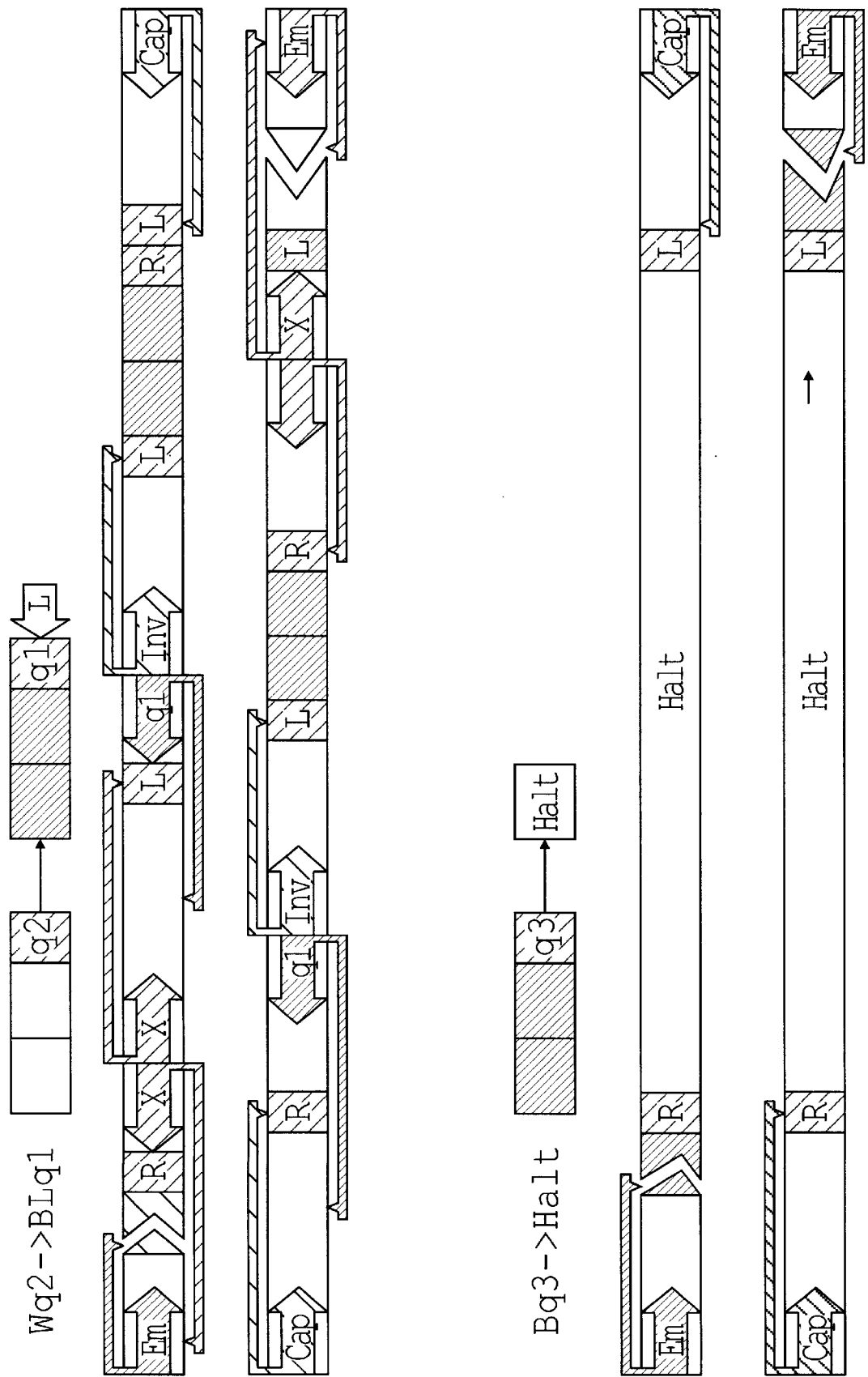
Figures 2, 18B:
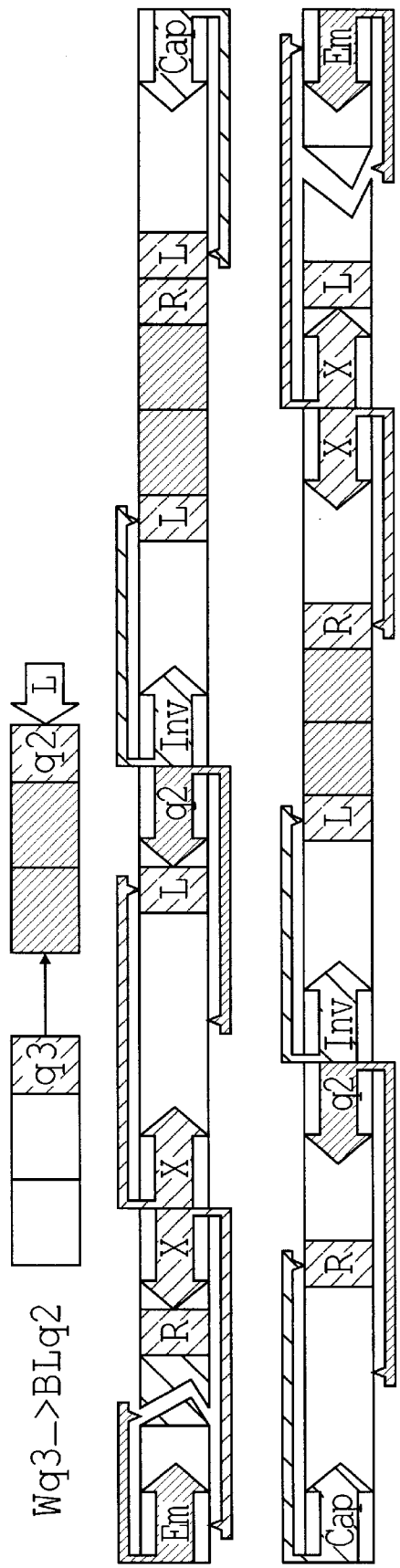

FIG. 16 shows schematically the overhangs generated when the symbols W and B are cut into each of the three frames from both the right and the left. The restriction site for each frame is labeled with the state it represents (q1–q3) and is shaded to match FIG. 2. FIG. 17 shows the actual DNA overhangs generated when the B and W symbols are cut by the state cutter enzyme FokI in three different state frames from both the left and the right. Each overhang is unique and mismatches every other overhang (or complement of an overhang) in at least two positions. It should be noted that in this example the sequences have been designed such that the overhangs for state q1 include one of the bases of the invariant sequence. The invariant sequence is then regenerated when the transition nucleotide is inserted. The advantage of designing the sequences in this way is that the symbol sequences can be made shorter.
Encoding the Transition Table.

Figure 2:
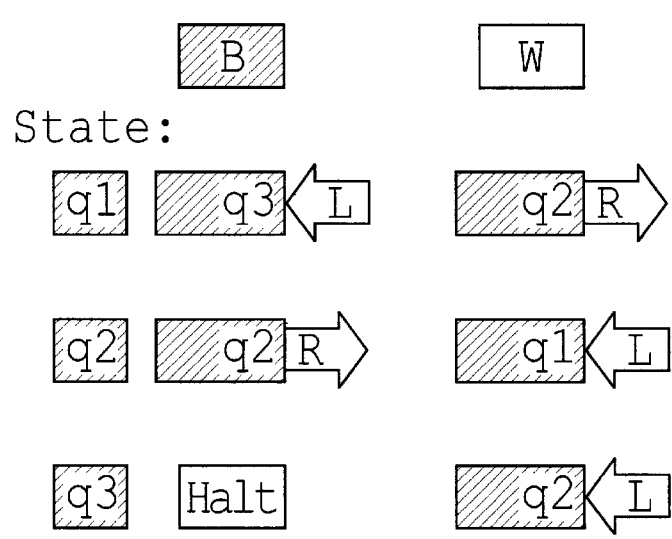
FIG. 2 is a schematic drawing of a transition table for a prior art three state Busy Beaver (BB-3) Turing machine.
Figure 3:
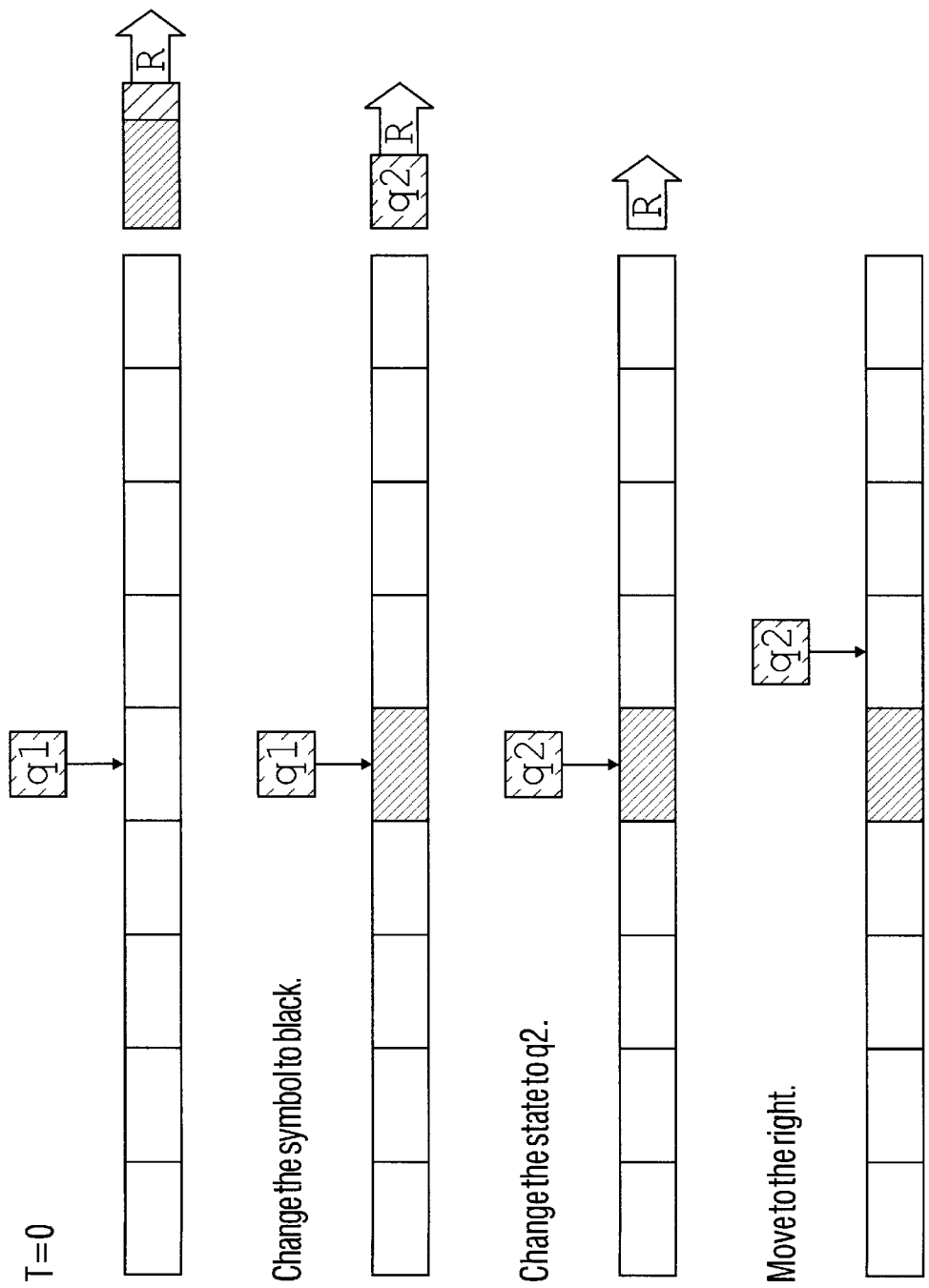
FIG. 3 depicts a schematic representation of a time step transition of the BB-3 Turing machine of FIG. 2.
Figure 4:
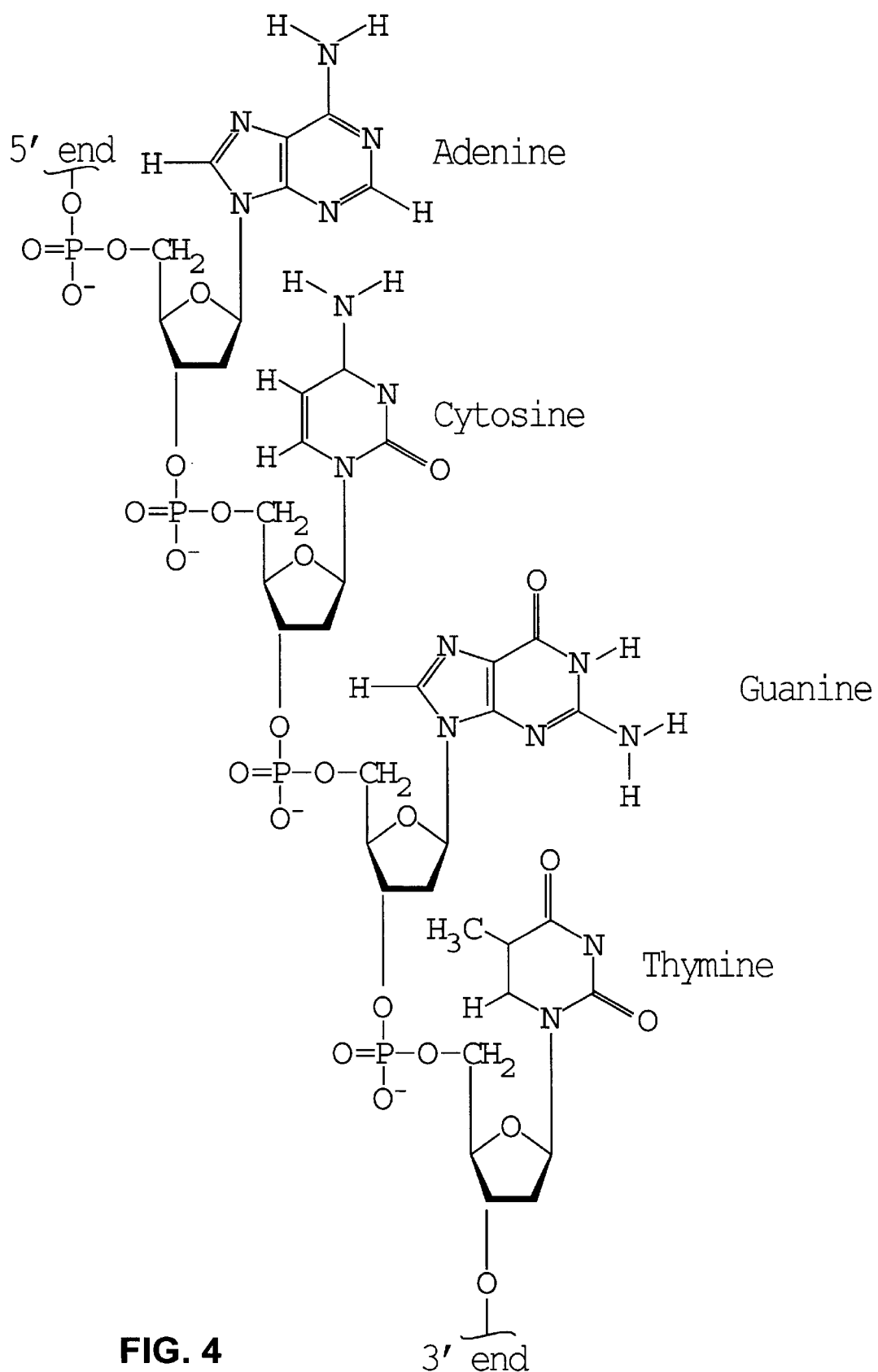
FIG. 4 shows a portion of a DNA polynucleotide chain.
Figure 5A:
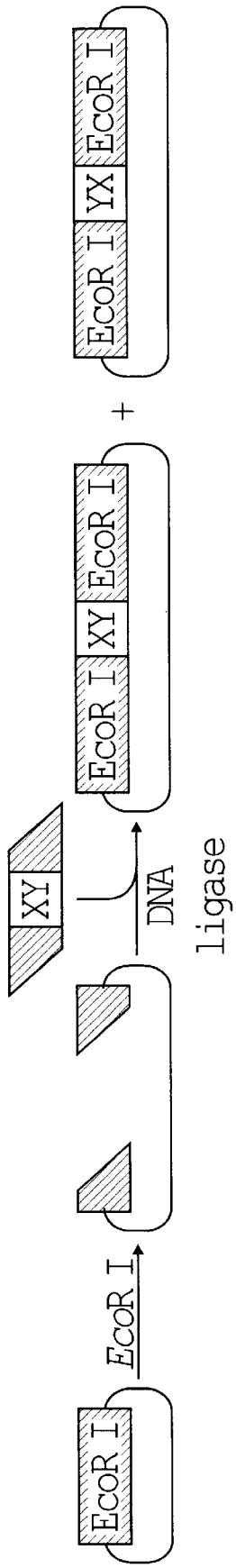
FIGS. 5A–5C illustrate insertion of a DNA fragment XY into a plasmid without orientation control.
Figure 5B:
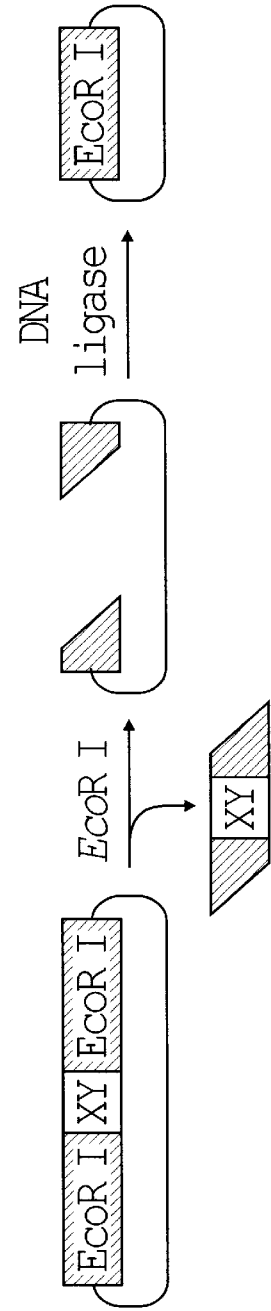
Figure 5C:
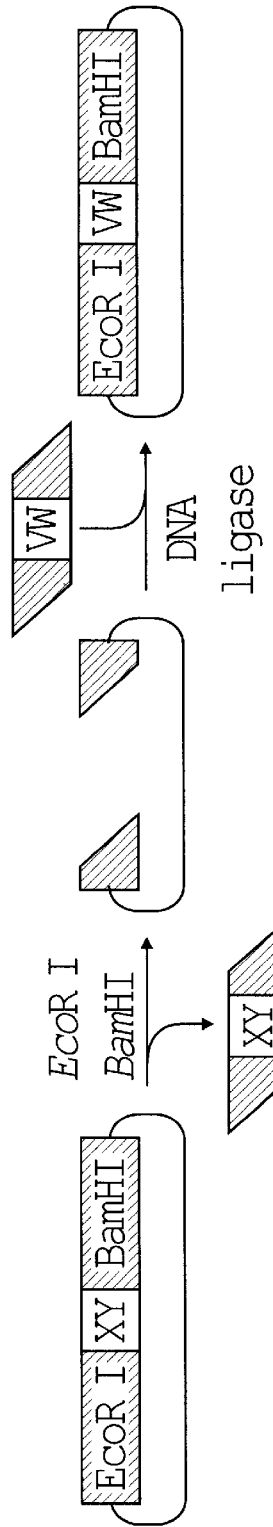
Figure 12:
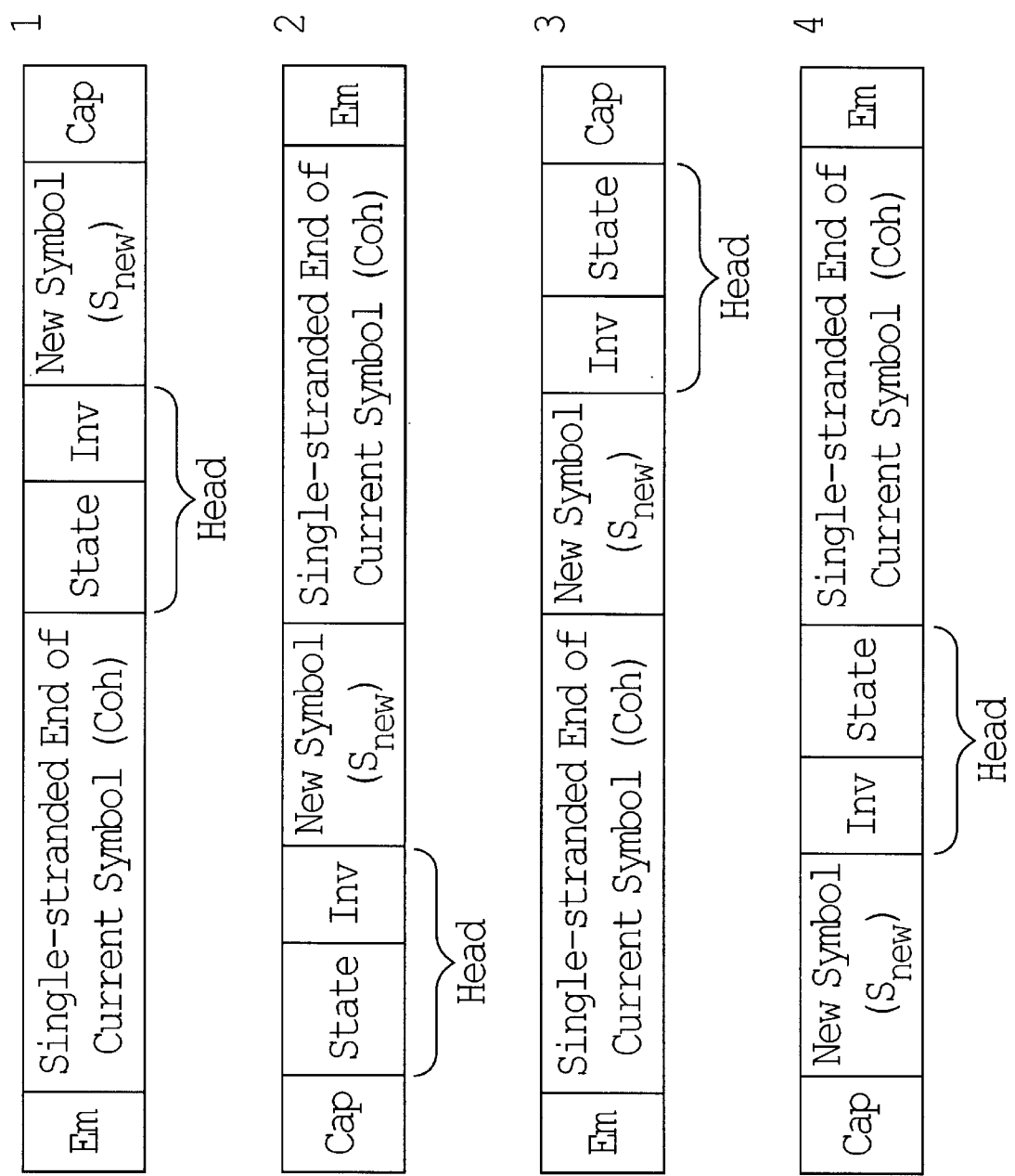
FIG. 12 is an alternate representation of the transition oligonucleotides of FIG. 11.

The transition table for the 3-BBN Turing machine shown in FIG. 2 is translated using the four types of transition oligonucleotides shown in FIGS. 11 and 12, making one oligonucleotide with a single-stranded end Coh complementary to each end depicted in FIG. 17. This generates the oligonucleotide encoded transition table set forth in FIG. 18. A j×k TM encoded this way has 2jk or 12 transition oligonucleotides.

The restriction sites for the enzymes BbvI and FokI are assigned to the end-maker and state sequences and the restriction sites BseRI, BsrDI, and BpmI are assigned to the invariant, cap and symbol-excision sequences (FIG. 19). The transition table oligonucleotides are constructed by a direct substitution of the chosen symbol sequences, restriction enzyme sequences and cohesive end sequences into the schematic drawing of FIG. 18. An extra two nucleotide spacer has to be added between the symbol excision sites X and the single-stranded overhang Coh because BpmI excises a longer intervening sequence than is necessary to cut out the last symbol.
Making a Transition.

An instantaneous description for a BB-3 DNA Turing machine operating on a blank tape is illustrated in FIG. 20. The six chemical steps required to take this ID at time T to the ID at time T+1 are set forth in FIG. 20 and explained below:

In step 1, the current symbol is cut with the state and invariant restriction enzymes, FokI and BseRI, respectively. The white single-stranded overhang created by the state cutting enzyme is specific for the symbol-state combination (W, q1) and matches an oligonucleotide encoding the transition Wq1→Bq2R, shown schematically to the right of the tape in FIG. 20. The invariant cutting enzyme cleaves an R sequence to create an end that is the same regardless of what symbols lie to the left of the computation. If the last move had been from the right the invariant cutting enzyme would cleave an L sequence instead of an R sequence.

Figure 6A:
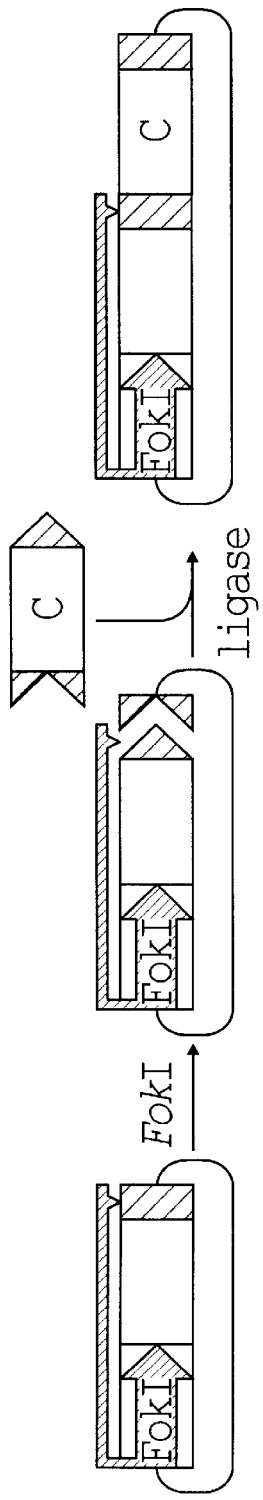
FIGS. 6A–6D illustrate various operations on a plasmid using a class IIS restriction enzyme.
Figure 6B:
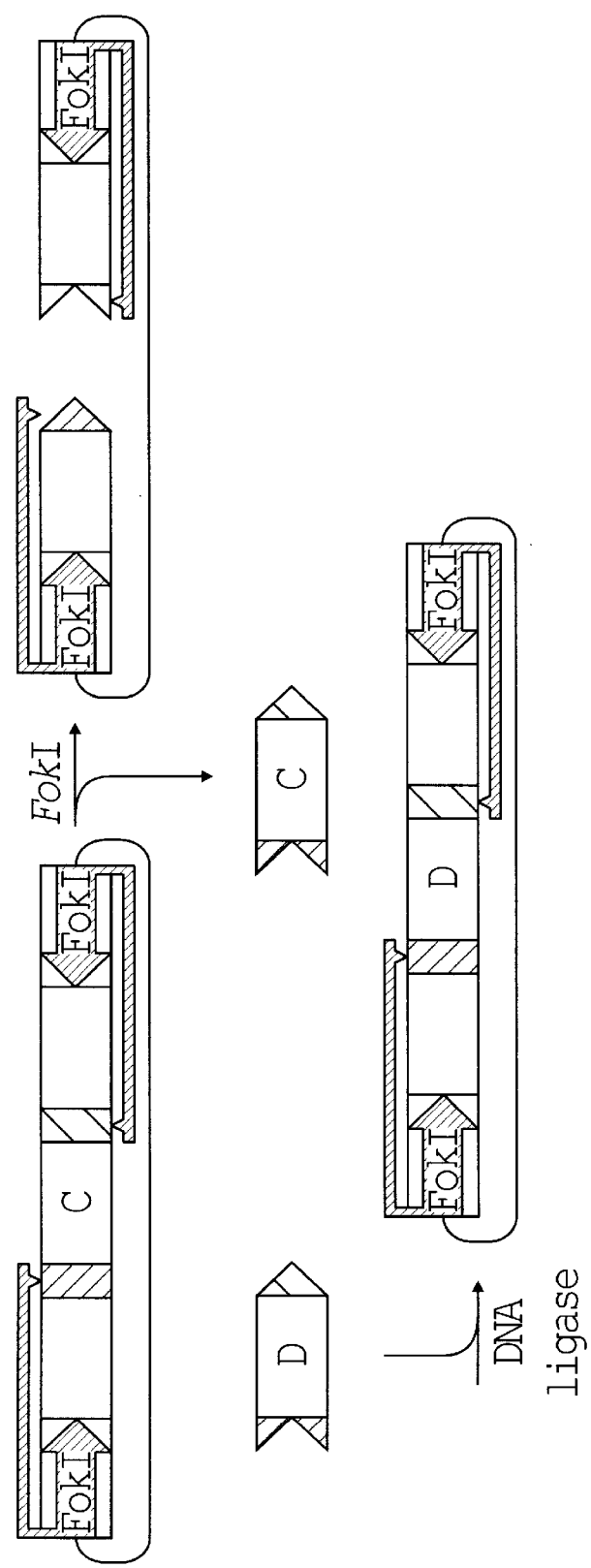
Figure 6C:
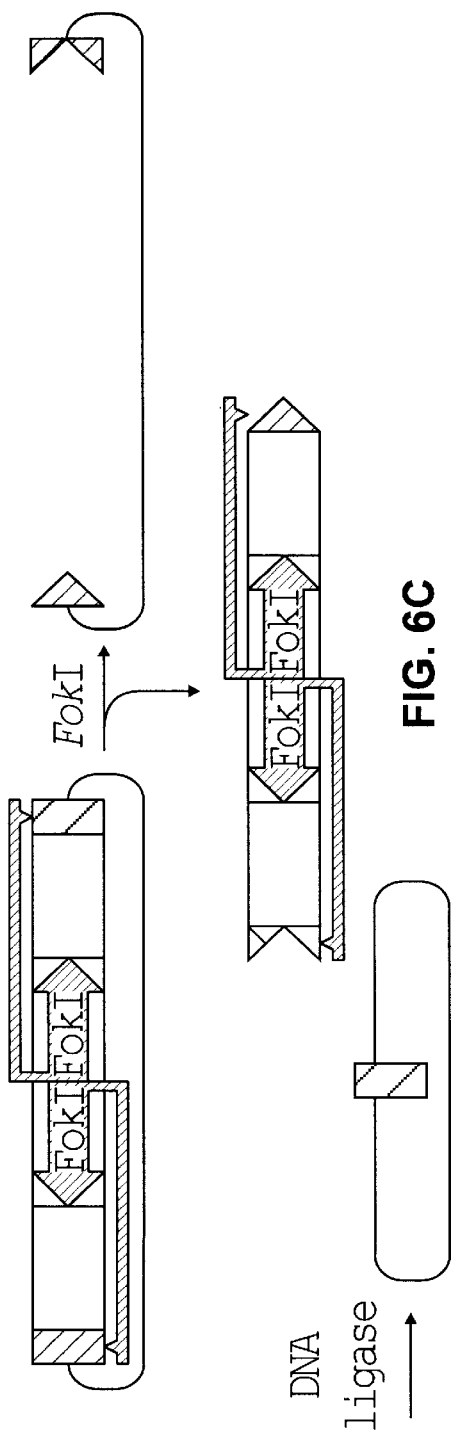
Figure 6D:
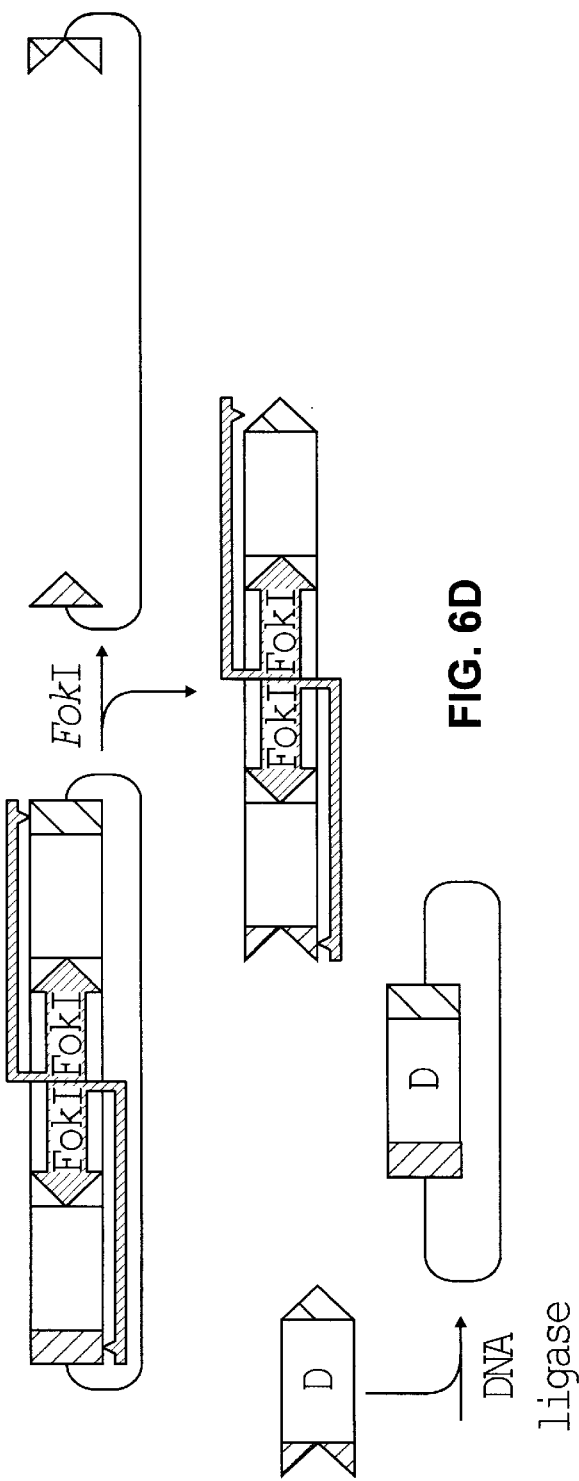

In step 2, the twelve transition oligonucleotides shown in FIG. 12 are mixed with the DNA Turing tape. The transition oligonucleotides are treated with end-maker restriction enzyme (BbvI) prior to addition to the Turing tape. As discussed above, this enzyme cuts at restriction site Em to create unique single-stranded overhangs. In FIG. 6D the oligonucleotide insert D has unique cohesive ends on both ends. In this example, however, only the single-stranded overhang generated by the state cutter is unique. The single-stranded overhang on the transition oligonucleotide that matches the end generated by the invariant cutting is therefore protected with the Cap sequence. DNA ligase is added to join the transition oligonucleotide to the tape.

Step 2 is thus, the ligation of the transition oligonucleotide encoding the transition Wq1 to Bq2R to the unique single-stranded overhang generated in Step 1. The direction of q2's "cutting arm" determines the direction of the head, the spacing between q2 and the invariant sequence R encodes the new state, the black sequence "behind" the head encodes the new symbol and the white sequence to the right of the X recognition site encodes the last symbol.

In step 3, the Cap sequence is cleaved with the Cap restriction enzyme BsrDI. Some restriction enzymes have difficulty cutting restriction sites near the ends of oligonucleotides. For this reason a few arbitrary nucleotides (not shown) may have to be added to the end of the Cap sequence.

In step 4, the DNA is cyclized with DNA ligase. Incorrect ligations can occur if the left cohesive end of an invariant sequence on one DNA tape sticks to the right cohesive end of an invariant sequence on another DNA tape. To favor the intramolecular cyclization reaction over the intermolecular reaction the reaction is run under very dilute concentrations of DNA, to increase the likelihood that any molecule of DNA will "see" its own cohesive end more often than those of others (Sambrook et al. (1989) *Strategies for Cloning in Plasmid Vectors in Molecular Cloning Lab Manual*, Cold Spring Harbor Press). Shorter DNA tapes (as long as they are not too short and stiff) will cyclize better than longer floppier DNA tapes (Crothers et al. (1992) Methods in Enzymology 212:3–31). One design consideration that must be made for shorter DNA tapes, however, is to ensure that the number of helical turns in the DNA tape after steps 4 and 6 is integral (Shore and Baldwin (1983) Journal of Molecular Biology 170:957–981). This guarantees that the circularized DNA is unrestrained and unsupercoiled. To further promote intramolecular cyclization of the DNA tapes DNA binding proteins, such as, catabolite activator protein (CAP) that are known to bend DNA and promote cyclization (Kahn and Crothers (1992) Proc. Natl Acad. Sci. USA 89:6343–6347) can be used.

In steps 5 and 6, the previously read symbol is deleted from the tape using the concept of "progress" defined above (FIG. 8). In step 5, the DNA tape is cut with symbol-excision restriction enzyme. This cuts away the previous symbol and leaves two matching invariant ends. In step 6, the DNA is recyclized with DNA ligase to join the invariant ends created in step 5. As in step 4, high dilution reaction conditions should be used in order to favor intramolecular cyclization. The state cutting restriction site (q2) now "points" to the current symbol and the DNA tape represents the next instantaneous description.

Steps 1–6 are repeated until a Halt sequence is incorporated into the tape and the computation is completed. As stated above, after any step 6, the computation may be checked for the incorporation of a Halt sequence. This can be done by PCR amplification of a small aliquot of the computation using the Halt sequence, to which a functional group that binds strongly to streptavidin has been incorporated, as a primer.

Figures 1, 21:
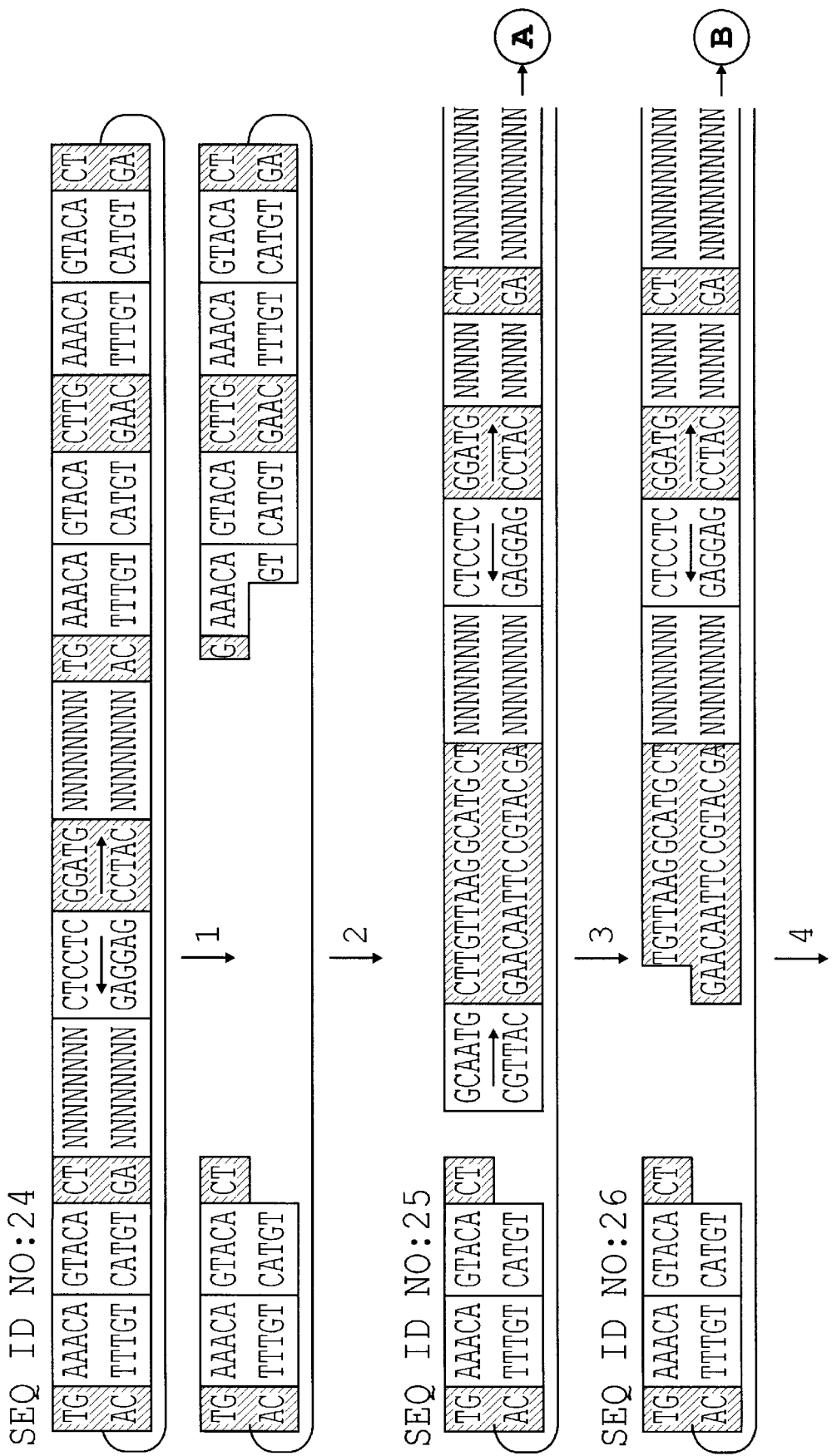
FIG. 21 depicts the transition of a BB-3 Turing machine at T=0 to T=1 showing the actual DNA sequences.
Figures 2, 21:
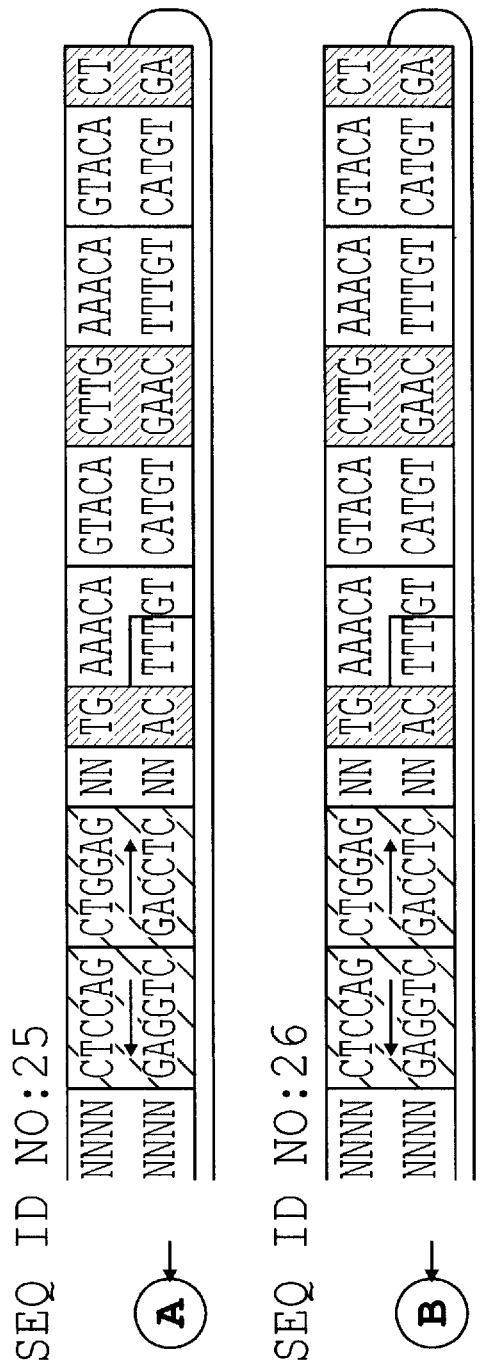
Figures 3, 21:
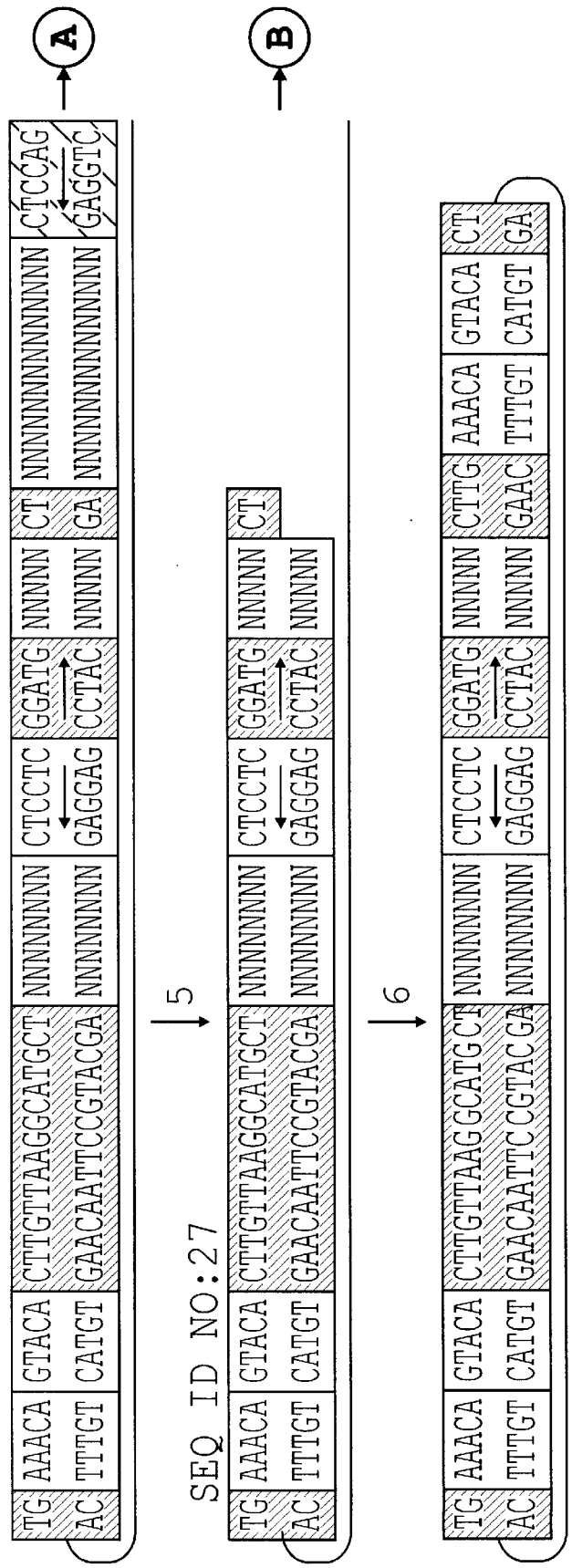
Figures 4, 21:
Figures 2, 22A:
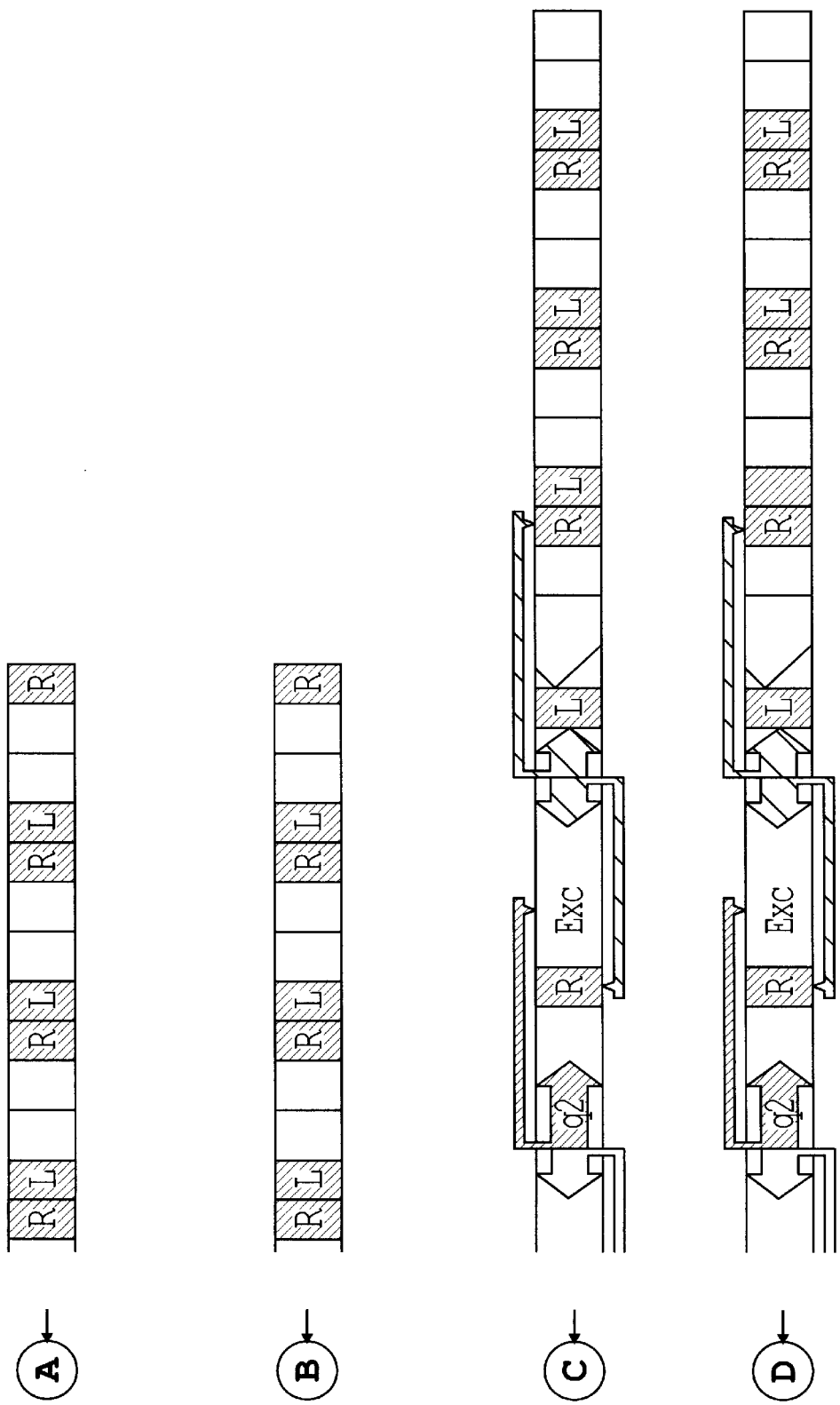
FIGS. 22A–22G depicts a complete schematic simulation of the Busy Beaver Turing machine from a blank tape containing 6 white symbols to 6 black symbols and a halt.
Figures 3, 22A:
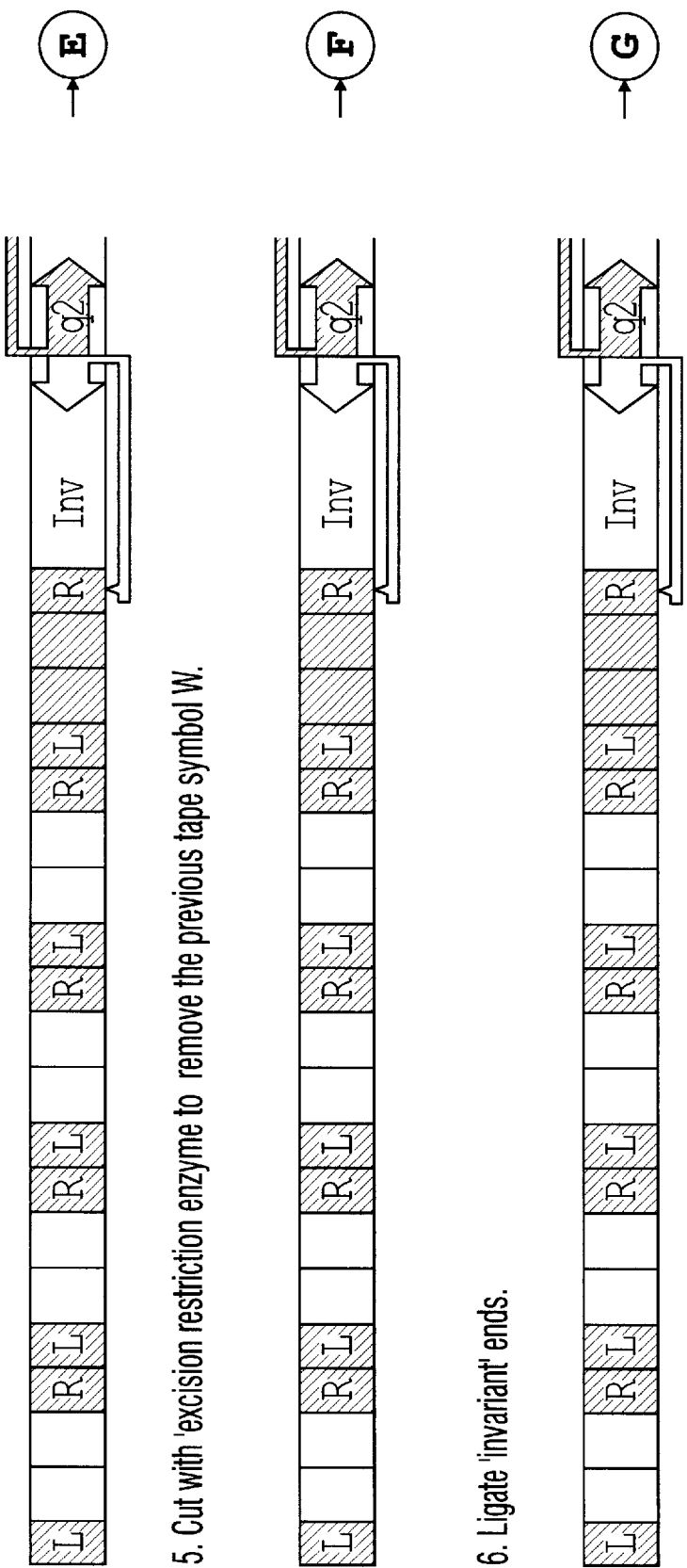
Figures 4, 22A:
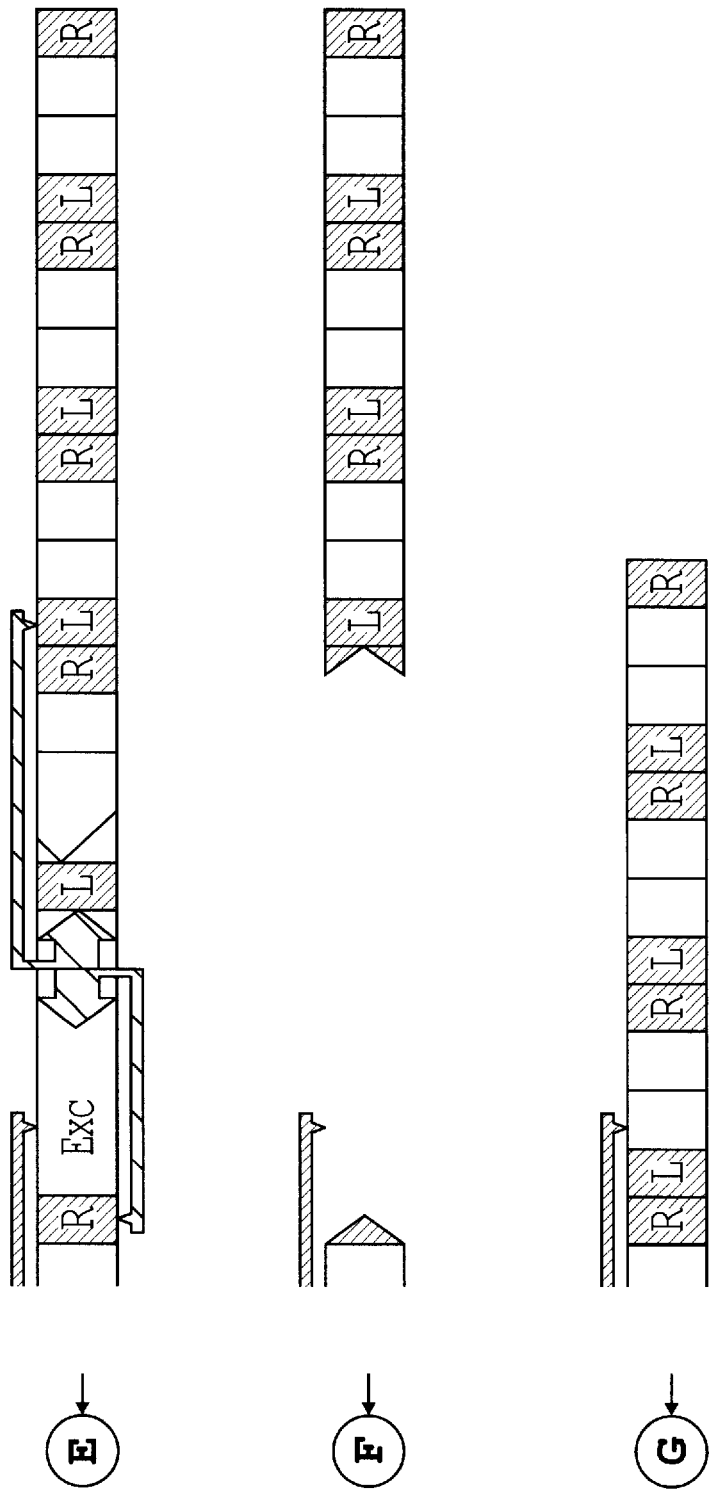
Figures 1, 22B:
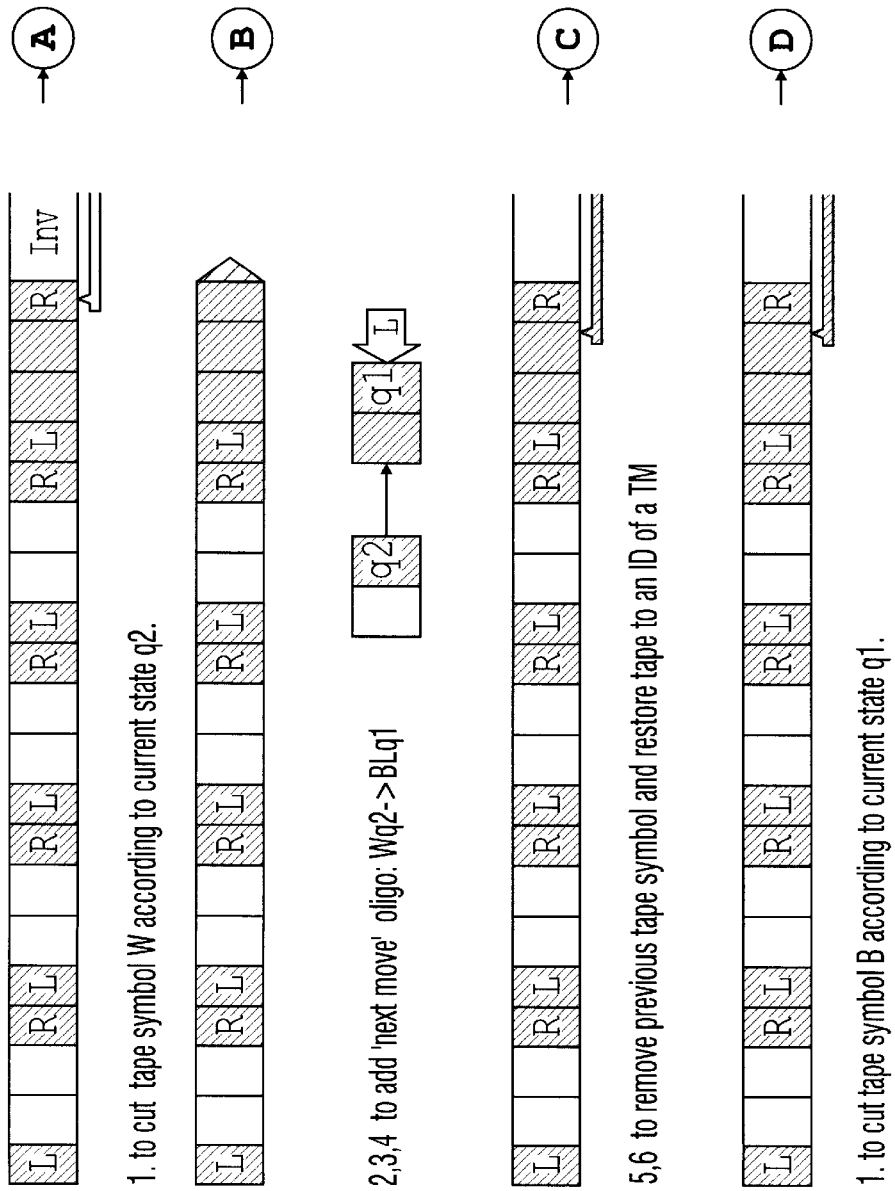
Figures 2, 22B:
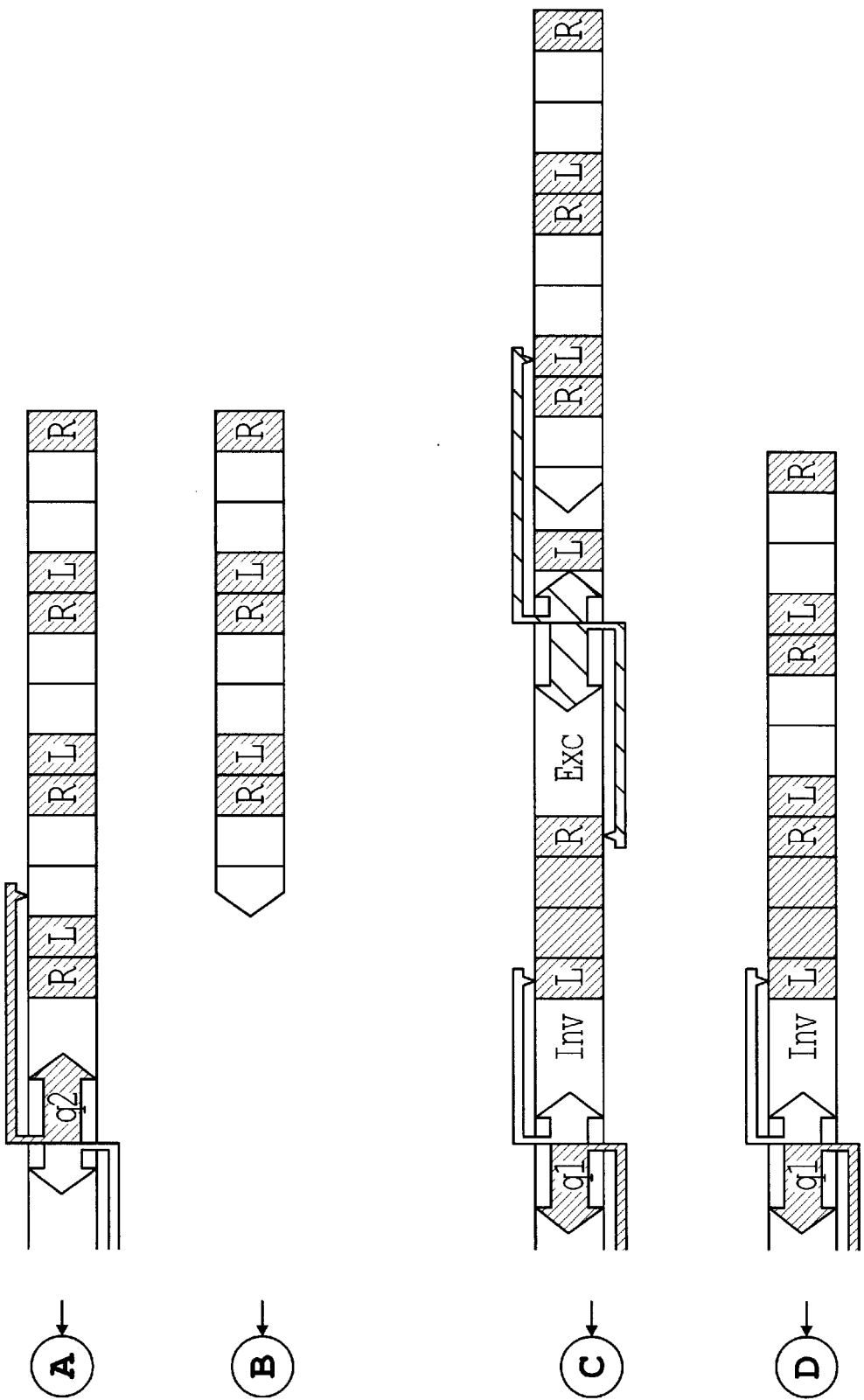
Figures 3, 22B:
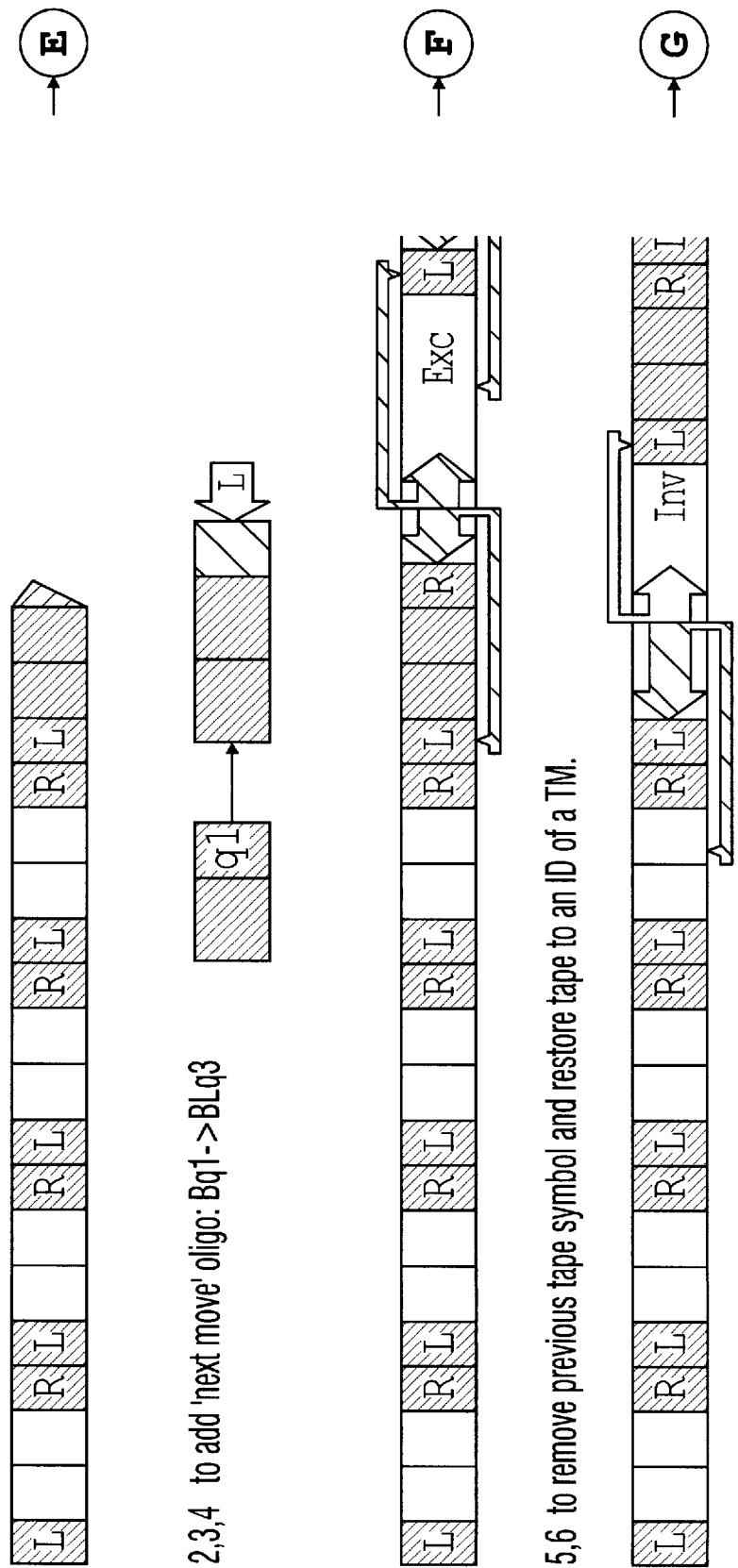
Figures 4, 22B:
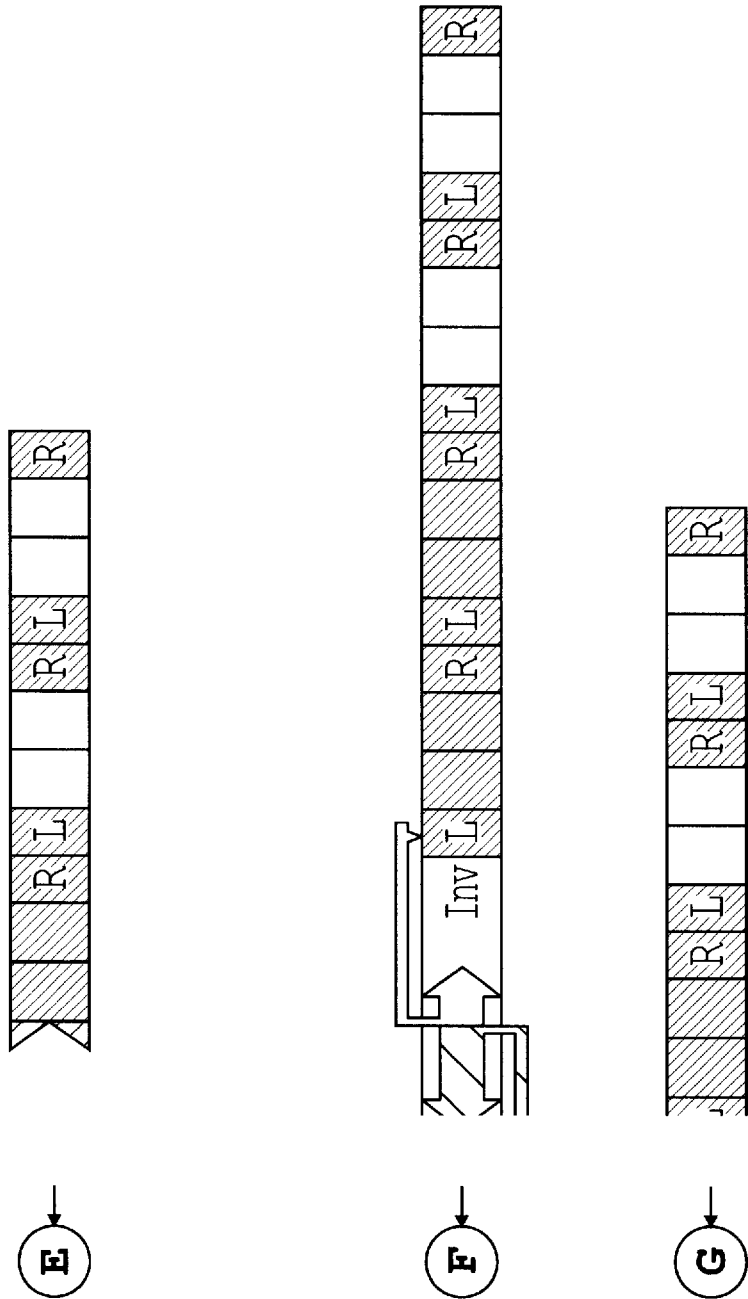
Figures 1, 22C:
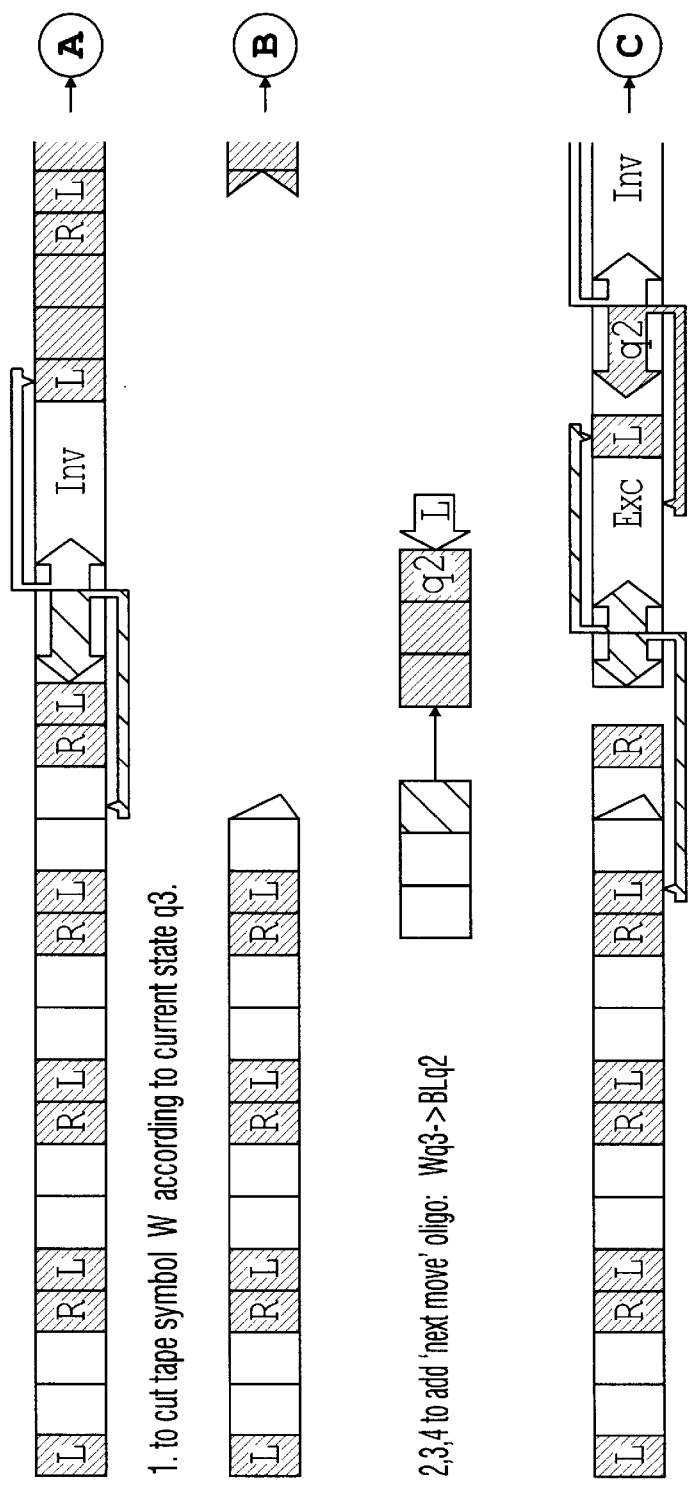
Figures 2, 22C:
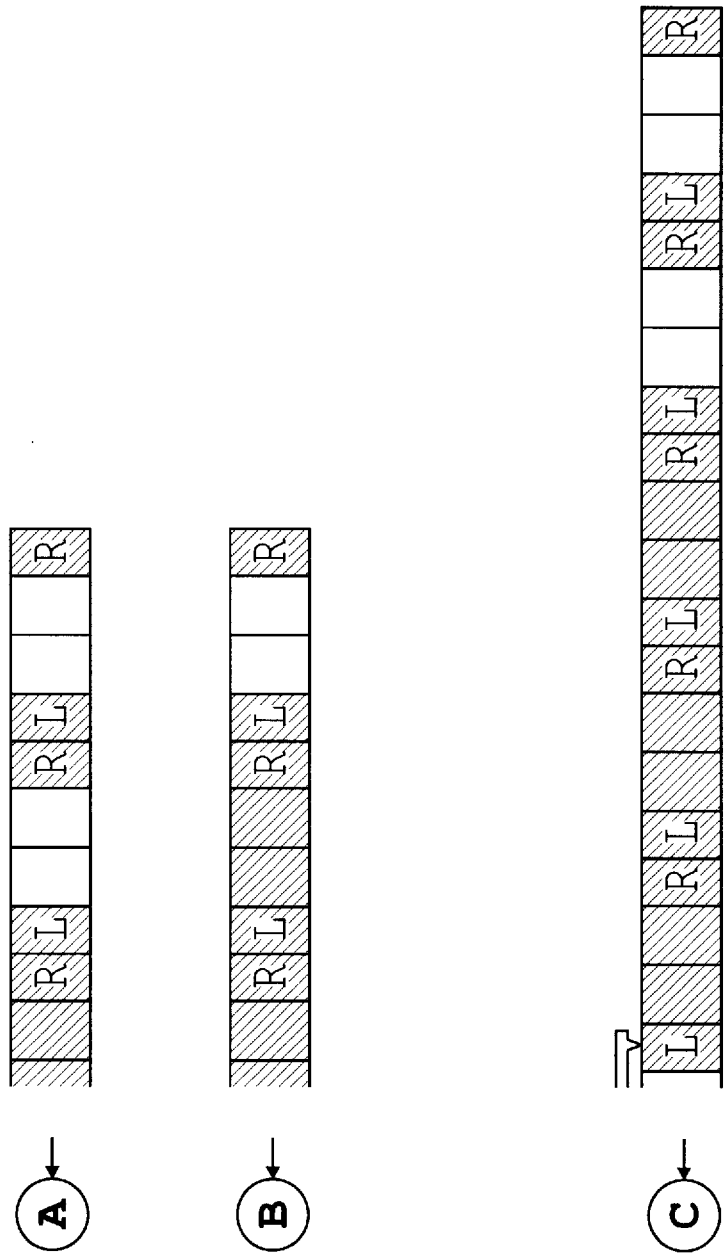
Figures 4, 22C:
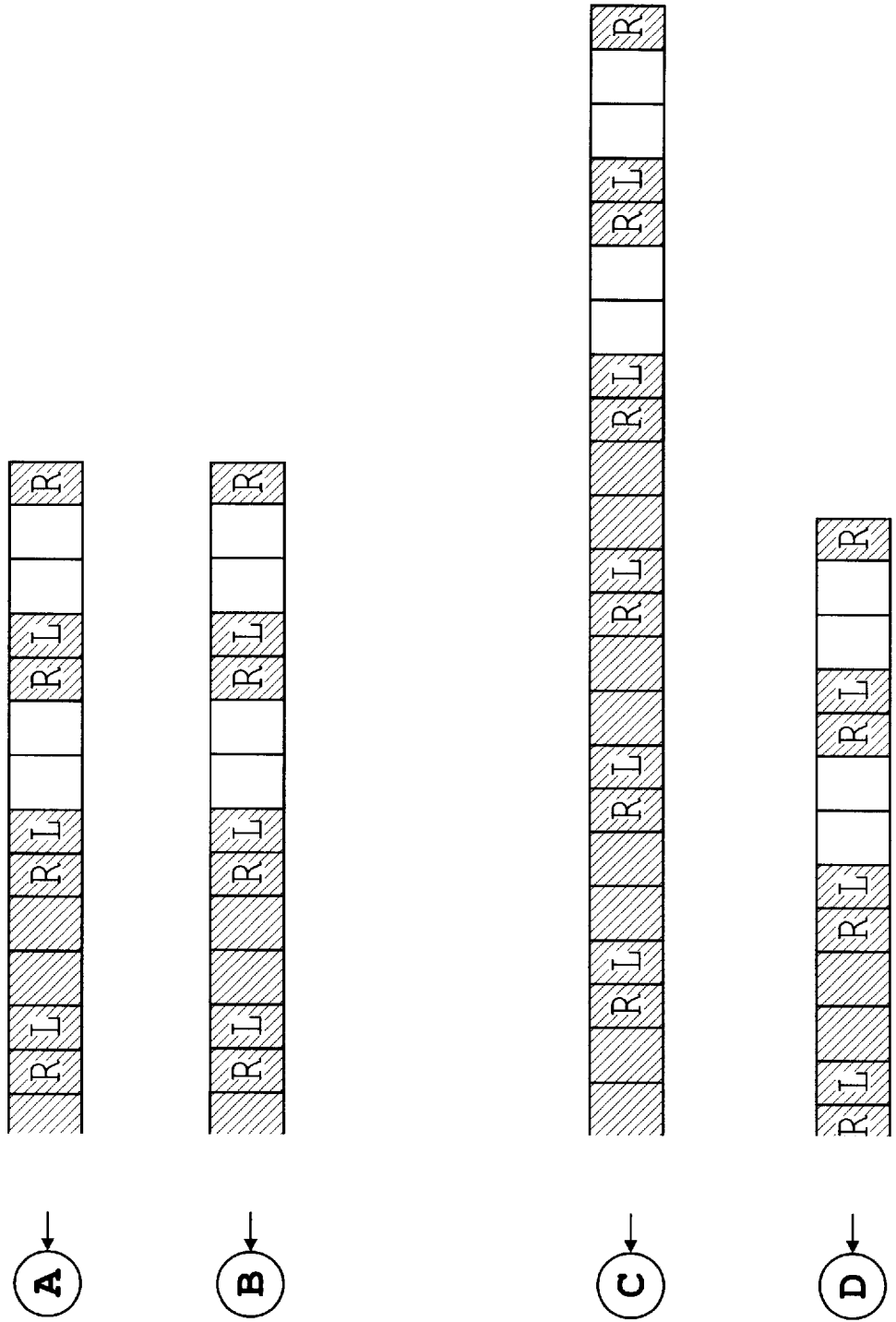
Figures 2, 22D:
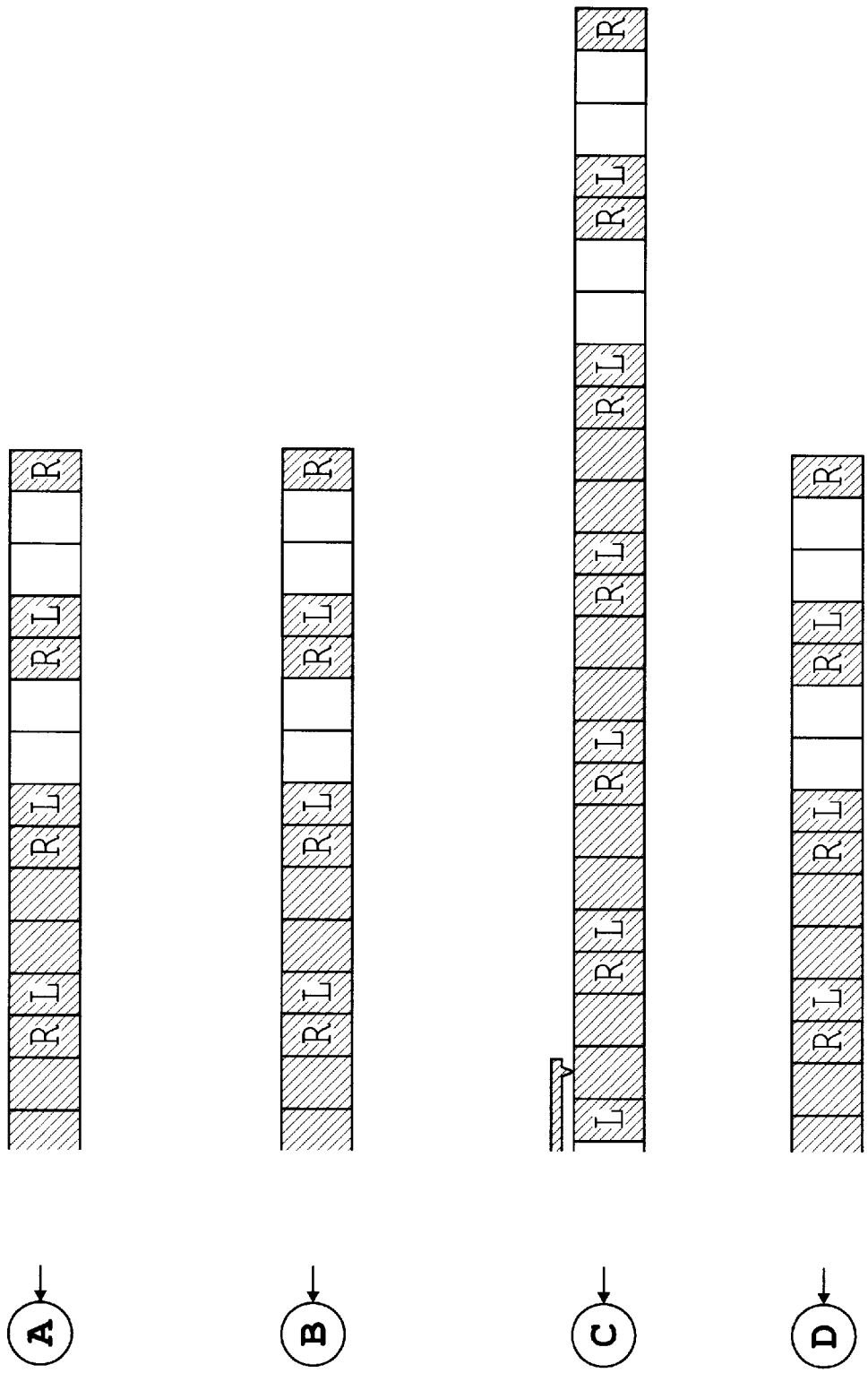
Figures 3, 22D:
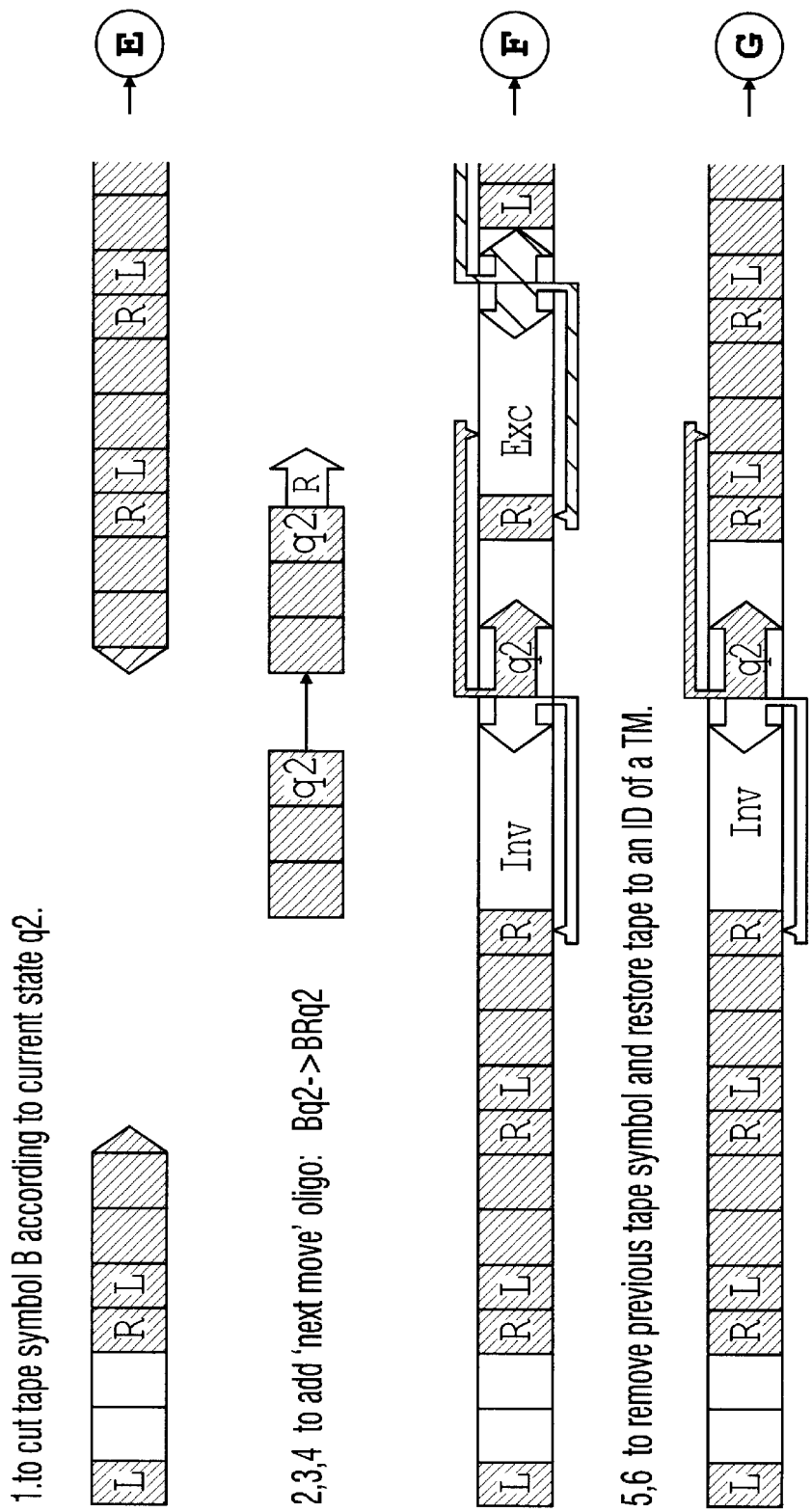
Figures 4, 22D:
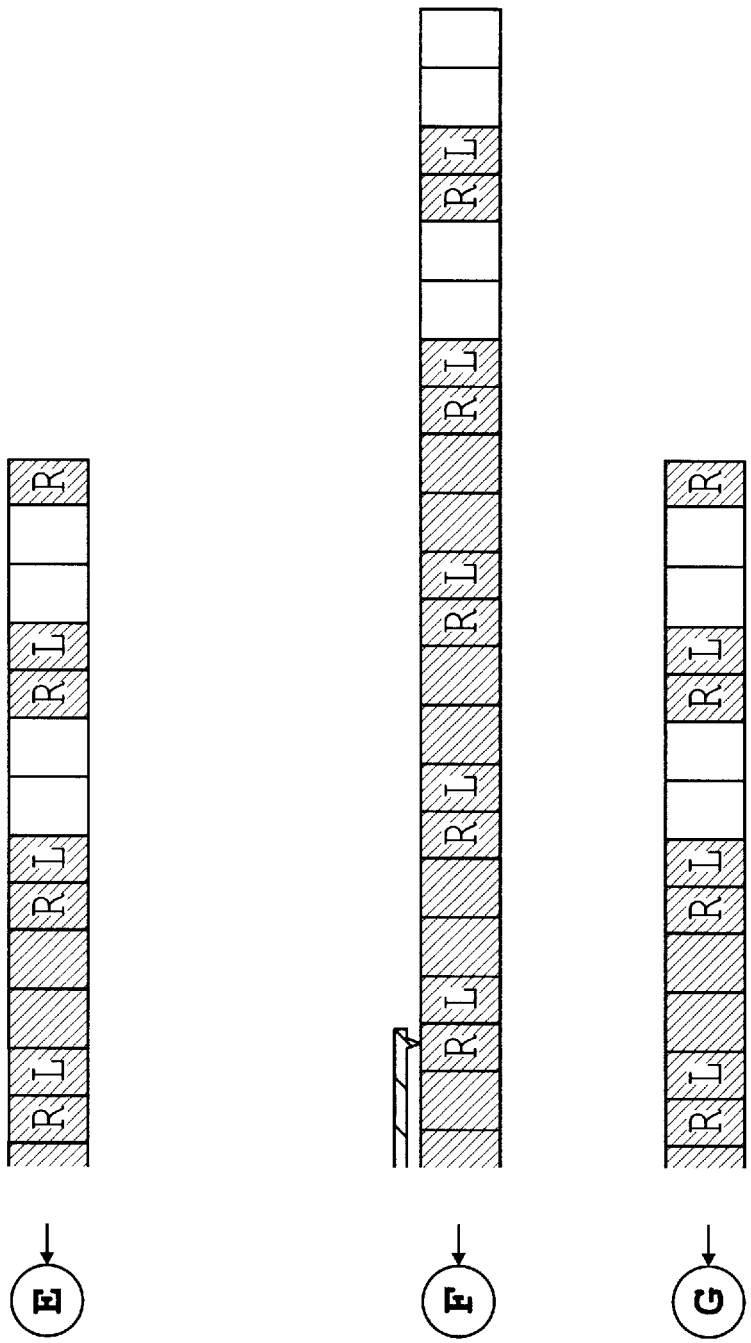
Figures 1, 22E:
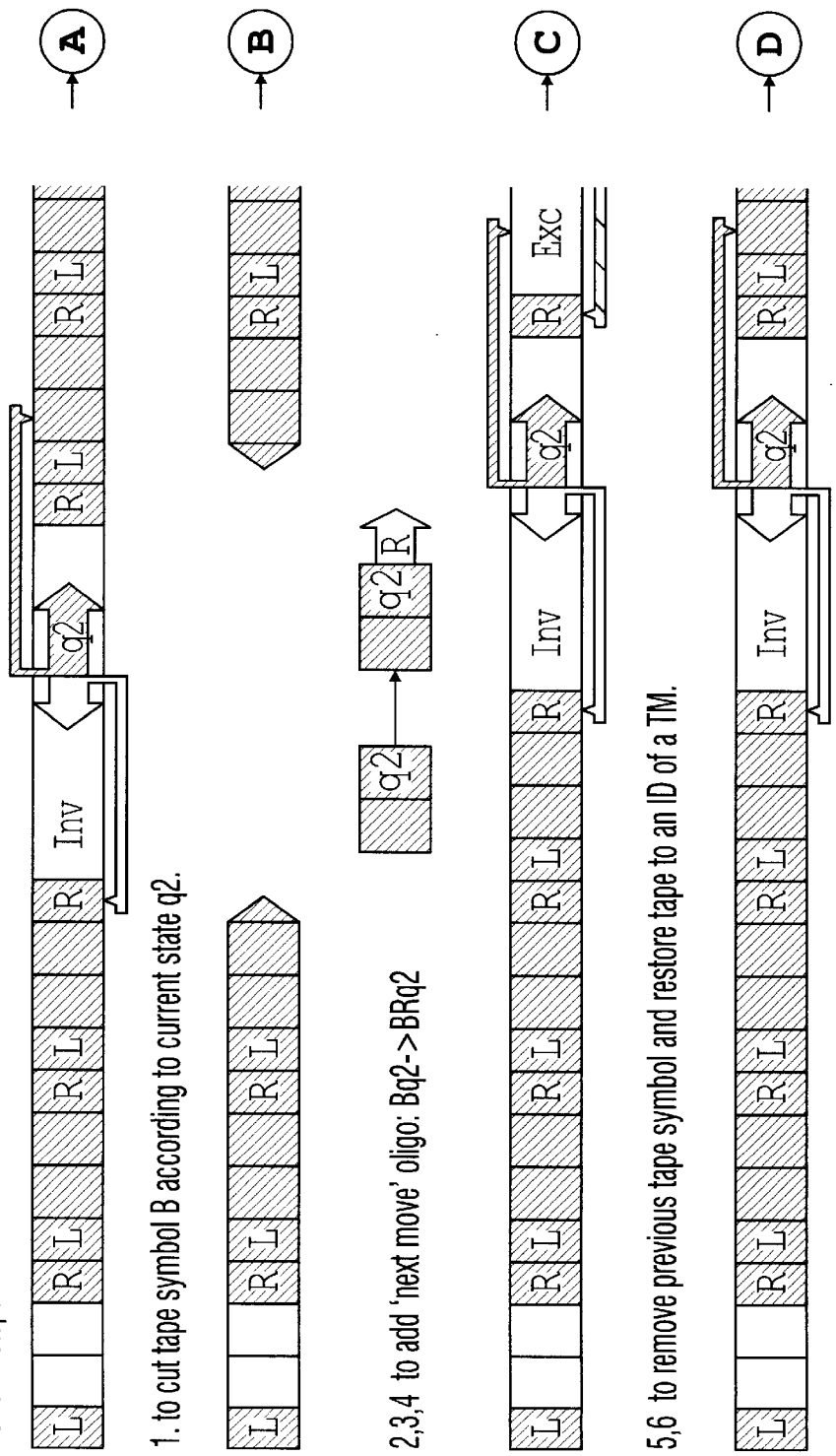
Figures 2, 22E:
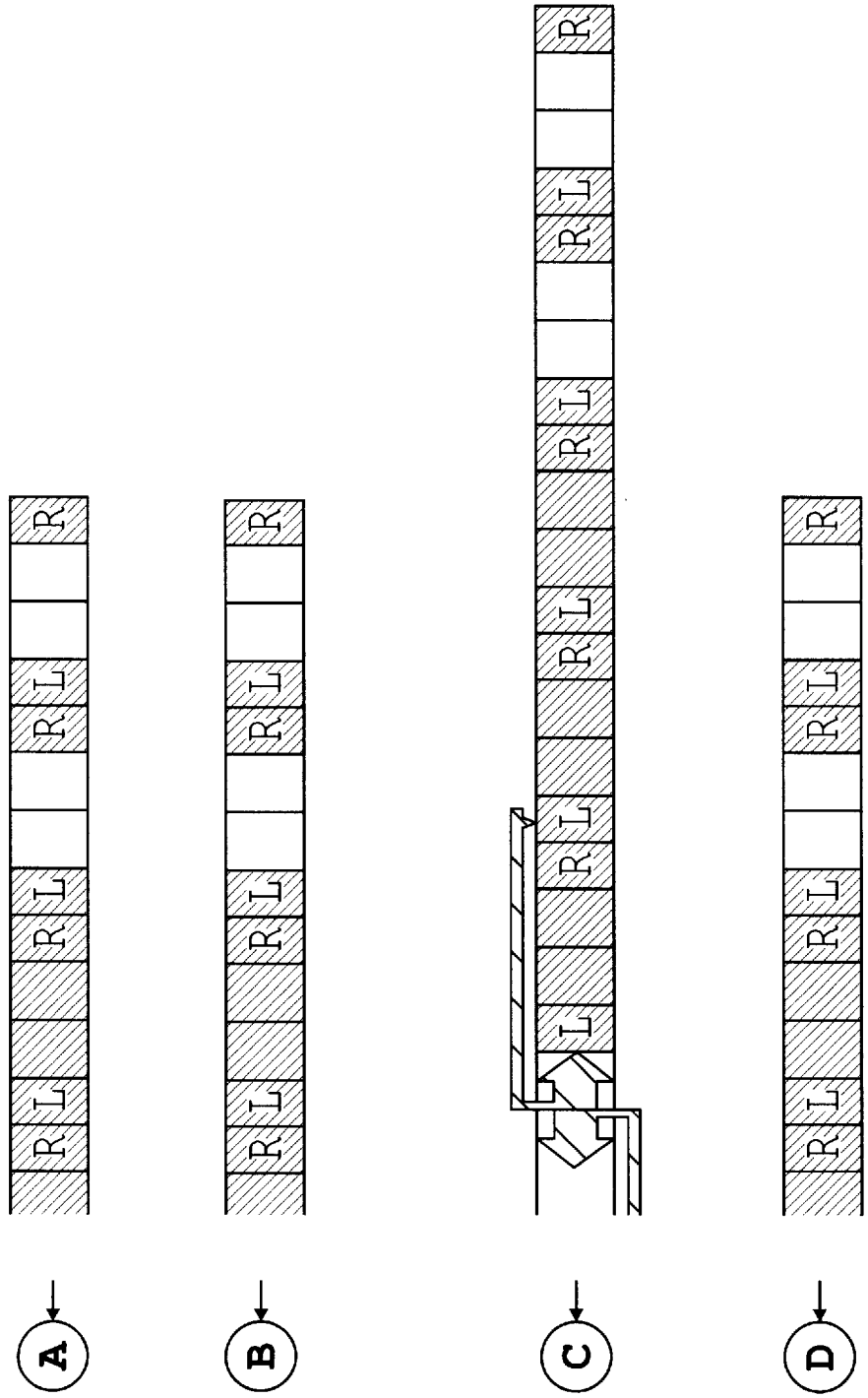
Figures 4, 22E:
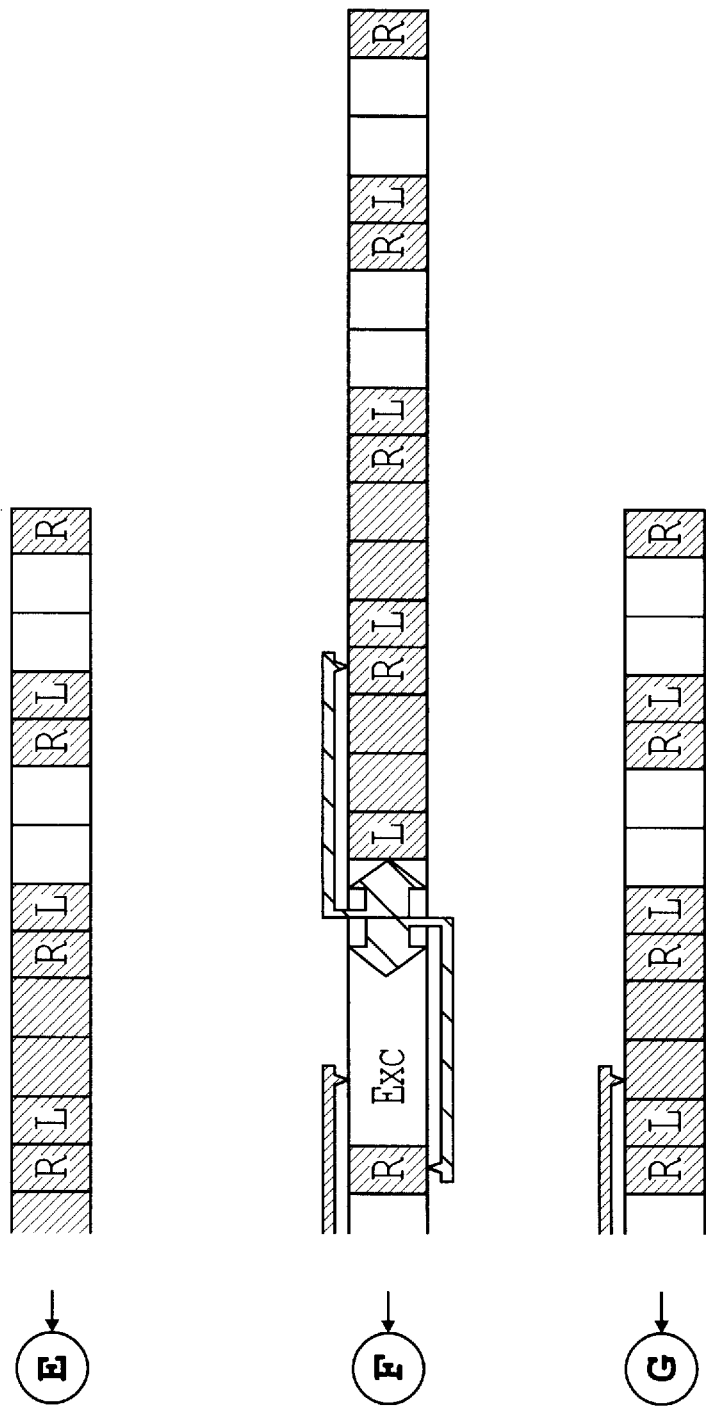
Figures 1, 22F:
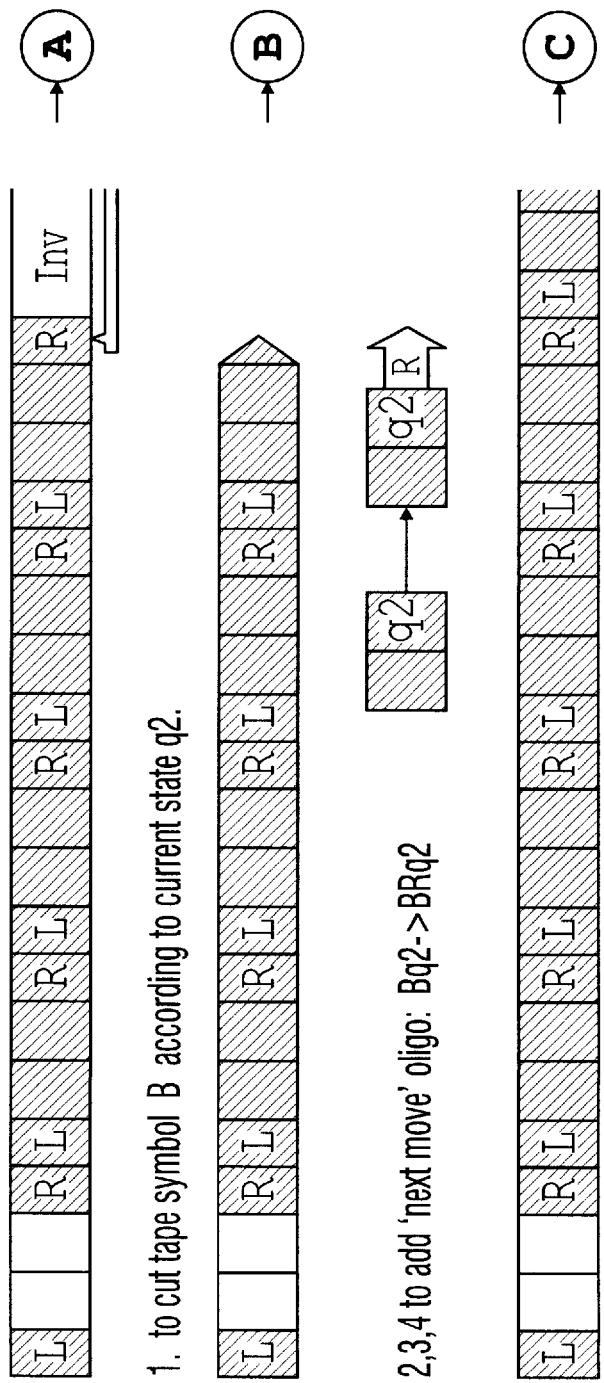
Figures 2, 22F:
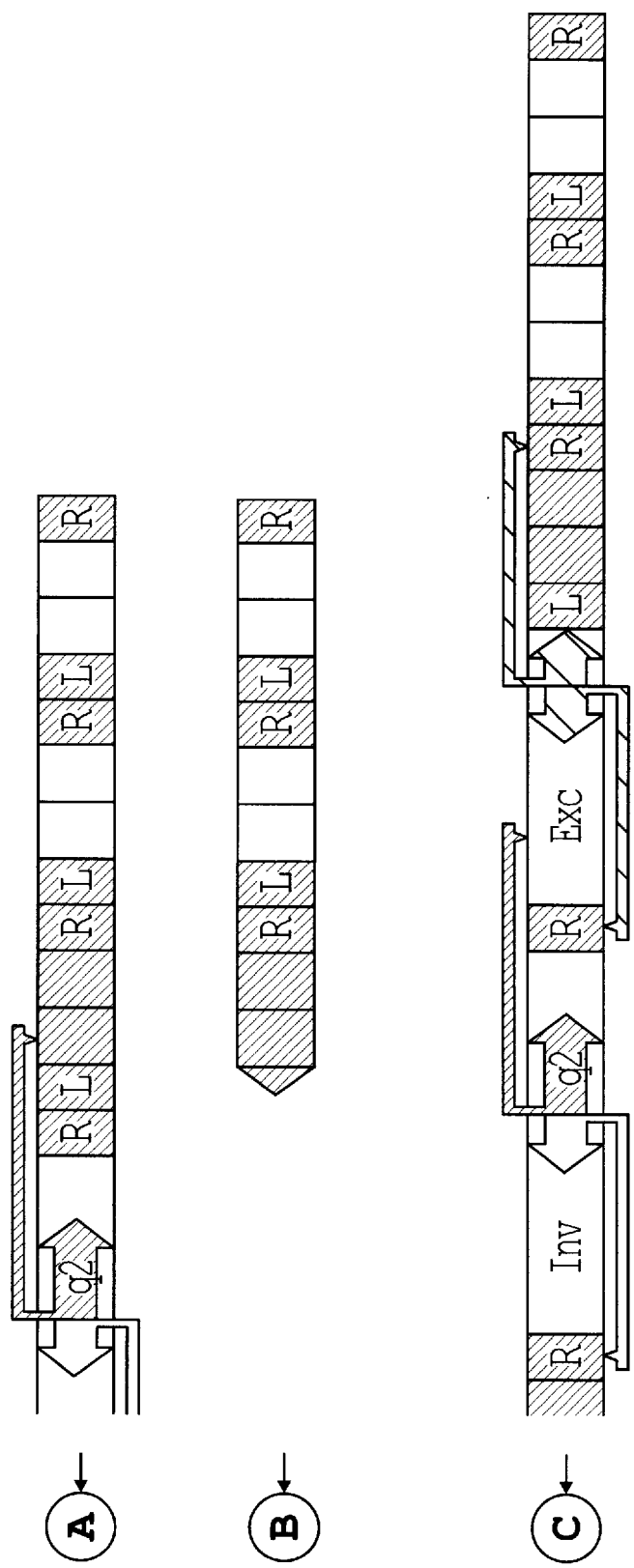
Figures 3, 22F:
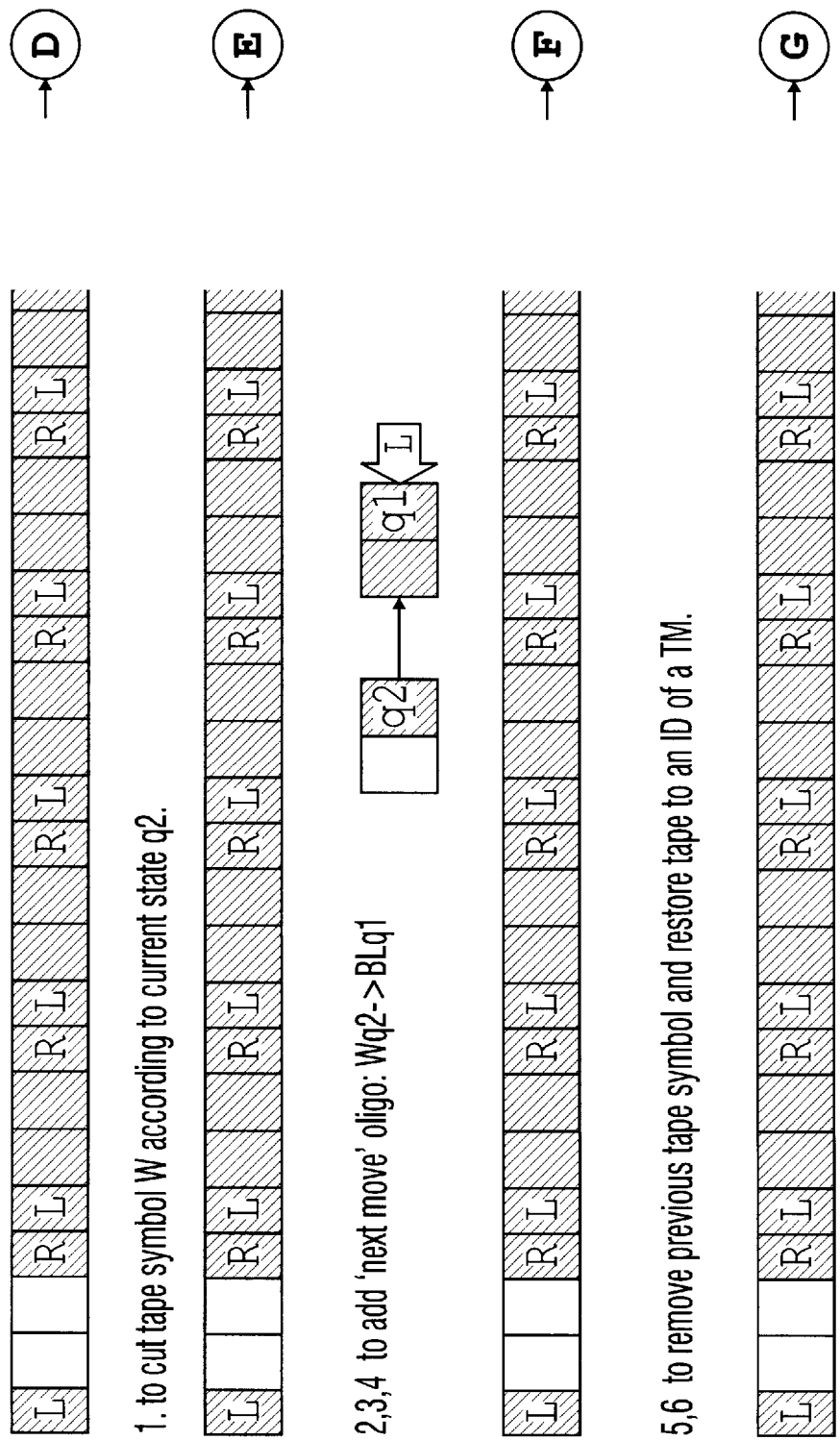
Figures 4, 22F:
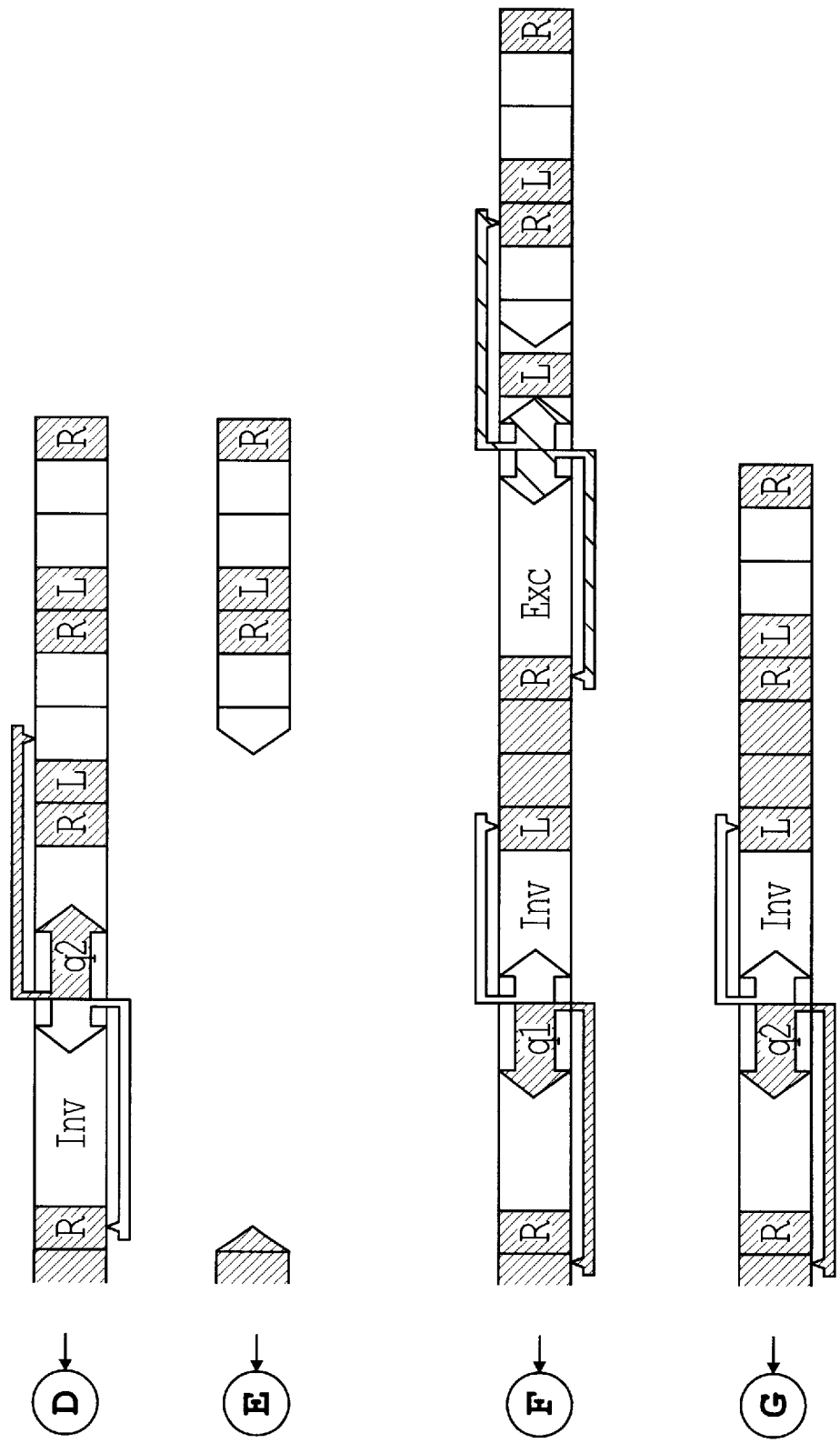
Figures 2, 22G:
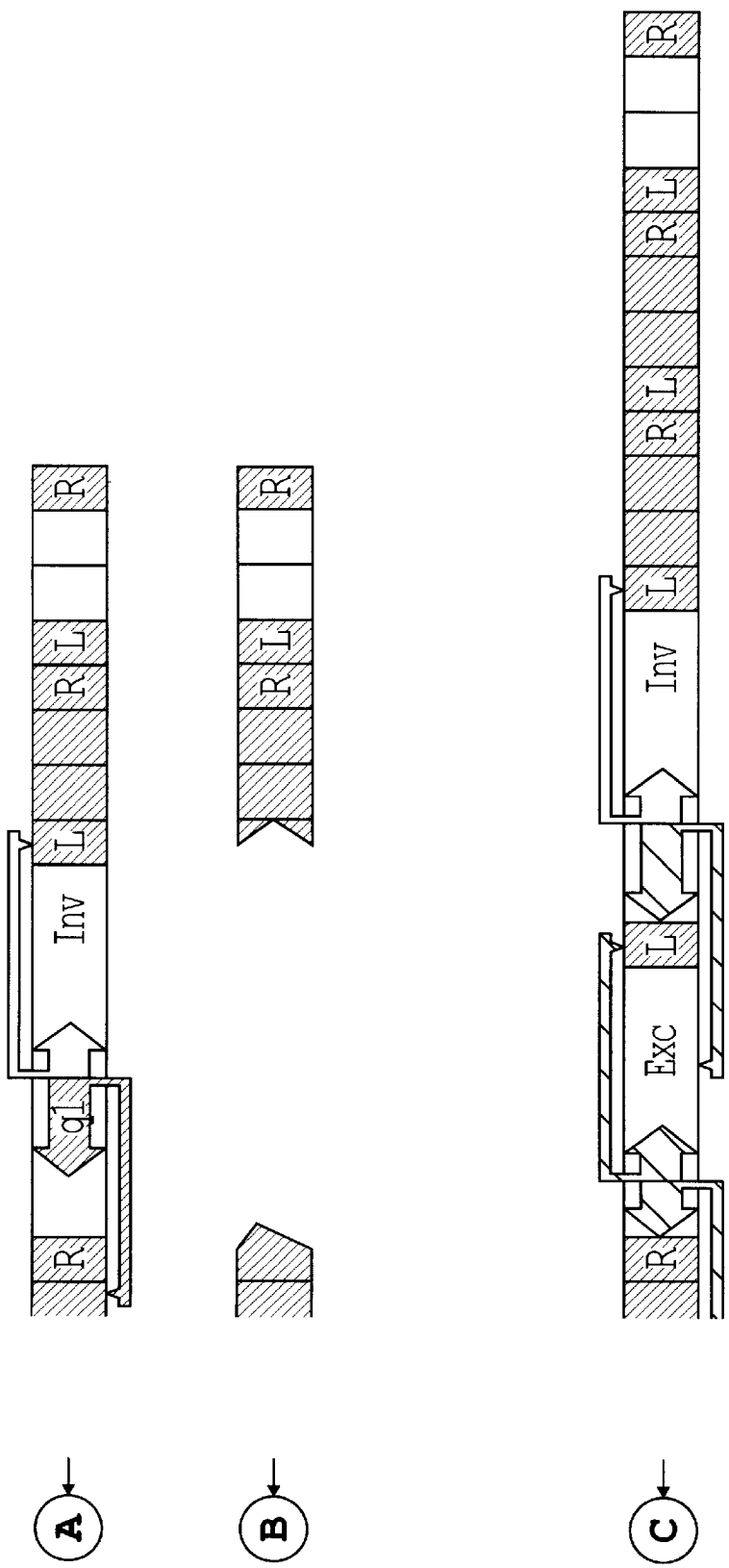
Figures 3, 22G:
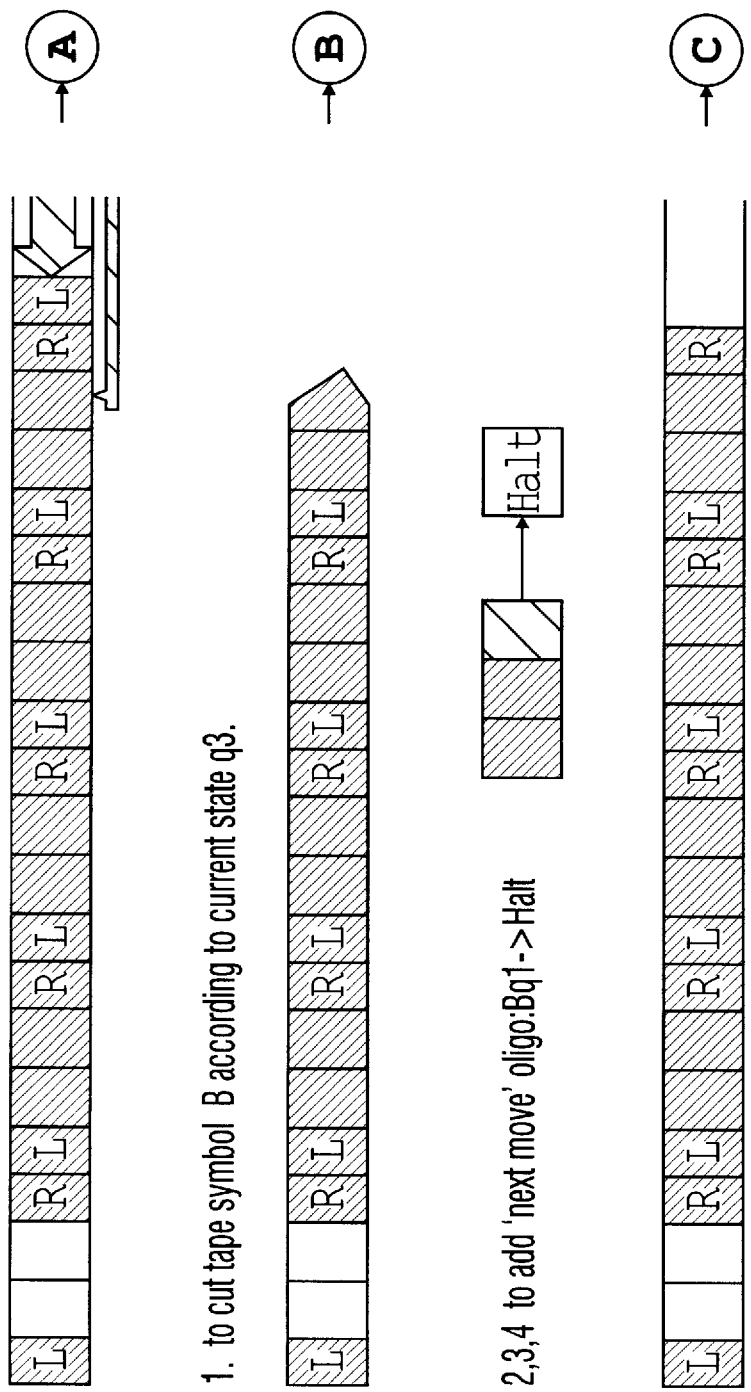
Figures 4, 22G:
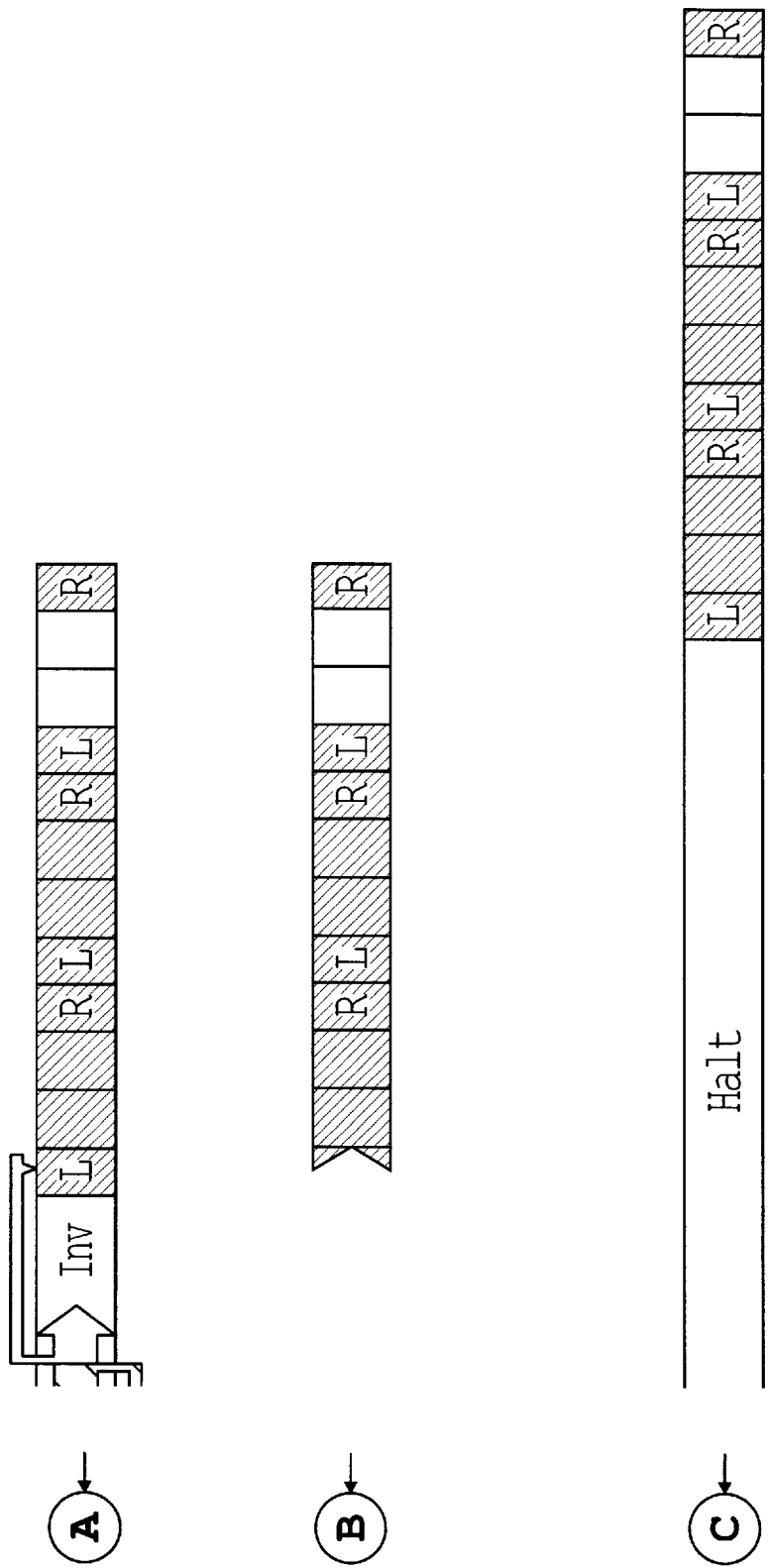

FIG. 21 depicts the transition of the BB-3 Turing machine at T=0 to T=1 showing the actual DNA sequences. FIG. 22 depicts a complete schematic simulation of the Busy Beaver Turing machine from a blank tape of 6 white symbols to 6 black symbols and a halt.

Several errors can occur during a computation. These errors lead to damaged tapes that must be removed, prior to continued computation. The errors and methods for removal are discussed below.

Occasionally, DNA ligase will fail to join two cohesive ends and will instead leave a piece of linear DNA. This can happen during the execution of the DNA Turing machine at step 2, if a transition oligonucleotide is not incorporated into the tape, or at steps 4 or 6, if one of the cyclization reactions fails. The "defective" linear tapes which result may be "degraded" with a DNA exonuclease, such as, Exonuclease III. As discussed above, exonucleases catalyze the cleavage of the phosphodiester bonds of the terminal or open 3'-nucleotides. Thus, tapes that have closed correctly will be resistant to cleavage. If the DNA ligase makes one of the two covalent bonds needed to seal the annealed ends, then Exonuclease III can only digest the strand with the nick and further treatment with a single-stranded nuclease such as S1 is necessary to degrade the other covalently-closed strand of the damaged tape. Single-stranded nucleases, such as S1, cleave double-stranded DNA at the single-stranded regions induced by mismatch (Burdon and Less (1985) Bioscience Reports 5:627–632).

DNA ligase can, under certain conditions, ligate mismatched pairs of sticky ends. (Wiaderkiewicz and Ruiz-Carillo (1987) Nucleic Acids Res. 15:7831–7848). These incorrect ligations can occur in one of two ways only during step 2. Identical copies of an invariant sticky end may be ligated (creating a mismatch at one position) or an incorrect oligonucleotide transition may be joined to the end left by the state cutter enzyme (creating mismatches at at least two positions). Tapes with such mismatches can be detected using a single-stranded nuclease such as nuclease S1 or with chemical reagents such as, hydroxylamine or osmium tetroxide, that modify mismatches and make them susceptible to cleavage by piperidine. (Cotton (1989) Biochemical Journal 263:1–10). Once the defective tapes have been identified and cleaved, subsequent treatment with Exonuclease III can remove them from the computation, as discussed above.

Restriction digests are not always complete, therefore, after steps 1, 3 and 5 some of the DNA tapes may still carry the head (Inv and State), Cap or excision (X) restriction sites, respectively. Before the computation can proceed these defective tapes must be removed from the reaction mixture to keep them from interfering with later steps. As discussed above, a biotin label incorporated into a Halt sequence can be used to remove DNA tapes that have finished computing. Biotin or other distinct reporter molecules can also be used to mark and retrieve tapes from which the head, Cap or X sites have failed to be cut. To incorporate the reporter groups into these sequences, extra nucleotides can be added at the end of the Cap sequence, between the back to back invariant and state recognition sites, or between the back to back occurrences of the symbol-excision recognition sites. After each restriction all DNA tapes that still have the reporter can then be removed, for example, by using affinity chromatography.

Examples of reporter molecules which can be used for this purpose include, but are not limited to, cholesterol, fluorescein and dinitrophenol. (*Clontech Catalog*, Clontech, Palo Alto, Calif. 1993/1994). The latter two may be retrieved with antibodies. Single-stranded oligonucleotide "side chains" may also be incorporated into the transition oligonucleotides with the use of branched phosphoramidites. Oligonucleotides complementary to these side chains could be used to remove tapes with failed ligations allowing a virtually infinite variety of reporter molecules.

Errors in which restriction enzymes cut at a site other than their recognition sites are extremely infrequent. When restriction enzymes do cut incorrectly, it is typically under non-standard reaction conditions and generally occurs at sequences closely related to their recognition sequence. (New England Biolabs Catalog (1995) (New England Biolabs, Beverly, Mass.)). Restriction reactions should, therefore, be carried out in their suggested buffers and similarities between a particular restriction site and the DNA which surrounds it should be minimized.

DNA Prototype of a Universal DNA Turing Machine.

The DNA based Turing machine of this invention has also been used to implement the 4 symbol, 7 state universal Turing machine as described by Minsky (Minsky (1962) *Proc. 5th Symp. in Appl. Math.*, American Mathematical Society, Providence, R.I., 229–238). This machine is constructed using the 4 symbols shown in FIG. 23. These symbols have the same propeity as those chosen for the Busy Beaver machine. That is, every four base overhang created by the state restriction enzyme mismatches every other such four base overhang in at least two places. FokI's cutting site can be shifted through these symbols 4 times to yield 4 different states. To obtain the remaining 3 states, an additional enzyme, HgaI, is used as a state cutter enzyme. HgaI creates 5 nucleotide overhangs (see restriction site Sta in FIG. 19). HgaI's cutting site can be shifted through 3 cutting frames in the given symbols, thereby creating an additional three states. Because the overhangs HgaI creates contain the 4 symbol sequences used in the FokI overhangs for states q1–q3 as subsequences, they also have the property that any pair of mismatched ends will have at least 2 mismatches. A UTM so constructed has 4*7*2=56 transition oligonucleotides. The transition table for this Turing machine is set forth in FIG. 24.

Unfortunately, no counterpart to the end-maker BbvI exists for HgaI, that is, there is no 5 base overhang cutter that recognizes a different site from HgaI for use in preparing the end of those oligonucleotides that anneal symbols cut by states q5, q6 and q7. In order to prepare them, therefore, both strands must either be synthesized explicitly or as two parts—one with a pre-cut HgaI restriction site, and the other with an uncut HgaI restriction site—that may be ligated together.

Implementation on a Solid Support.

A number of methods have been developed for the covalent attachment of DNA to a solid support (Fahy et al. (1993) Nucleic Acids Research 21:1819–1826; Weiner et al. (1993) Gene 126:35–41; Zhang and Seeman (1992) Journal of the American Chemical Society 114:2656–2663). The advantages of performing DNA chemistry on a solid support are twofold. First, the purification of reaction products is greatly simplified, in that reagents are applied and then simply washed away. This eliminates the necessity of cumbersome chromatographic purifications between successive steps. Second, the solid support can effect the separation of different DNA tapes by maintaining them at a low and constant concentration. Tapes that contain errors are less likely to interact with other correct tapes, because they are physically isolated on a solid support, thus their removal is not as urgent.

Figure 25:
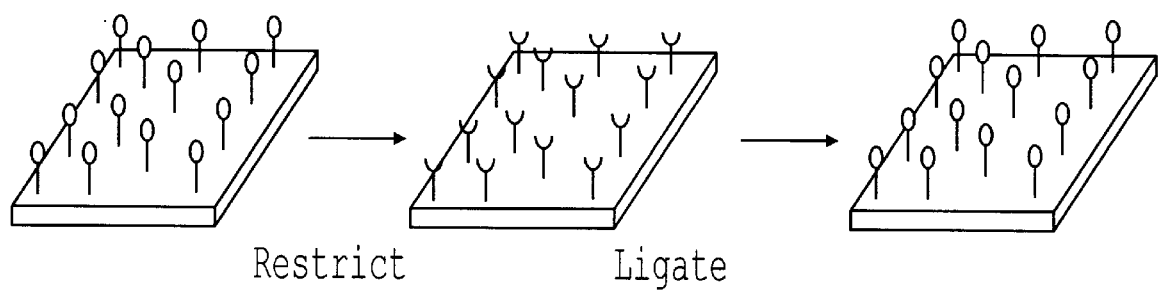
FIG. 25 illustrates DNA restriction and ligation on a solid support.

Zhang and Seeman have performed multiple restrictions and ligations on a solid support to synthesize multiple branched DNA molecules. (Zhang and Seeman (1992) Journal of the American Chemical Society 114:2656–2663). The reactions of this invention are much less complex and thus, could easily be performed on a solid support using standard methods known to those in the field. A simple loop encoding the computation attached to the substrate via a single branched junction would suffice. FIG. 25 shows the successive restriction and ligation of "eyelets" of DNA on a solid support. Detection of the Halt sequence can be accomplished by washing fluorescent or radio-labelled probes for the Halt sequence across the solid support. Retention of the label indicates that the computation is complete. The DNA tape can then be cleaved from the solid support using standard methods.

I claim:

1. A universal molecular Turing machine comprising:
a circular DNA molecule, having sites representing information storage of the Turing machine, said DNA molecule including:
   an invariant (Inv) restriction site inside the circular DNA molecule;
   a state restriction site also inside the circular DNA molecule, and adjacent to the Inv restriction site;
   a current symbol, encoded on the circular DNA molecule at a distance from said state restriction site that represents a state of the Turing machine;
   a plurality of intervening nucleotides between the state restriction site and the current symbol;
   a plurality of asymmetric restriction enzymes; and
   a plurality of transition oligonucleotides, which sre inserted into said circular DNA molecule as additional symbols to encode changes to said information storage caused by operation of said Turing machine.

2. The molecular Turing machine of claim 1 further including a DNA ligase.

3. A machine as in claim 1, further comprising asymmetric restriction enzymes, operating to cut said circular DNA molecule to insert or delete a symbol.

4. The molecular Turing machine of claim 3, wherein said plurality of asymmetric restriction enzymes are selected from the group consisting of Class IIS asymmetric restriction enzymes.

5. The molecular Turing machine of claim 4, wherein said Class IIS asymmetric restriction enzymes are selected from the group consisting of BbvI, FokI, BseRI, BsrDI, BpmI, and HgaI.

6. The molecular Turing machine of claim 1, wherein the Inv and State restriction sites are independently selected from the group consisting of BbvI, FokI, BseRI, BsrDI, BpmI, and HgaI.

7. The molecular Turing machine of claim 1, wherein the current symbol is a predetermined sequence of nucleotides.

8. The molecular Turing machine of claim 1, wherein said circular DNA molecule includes a first invariant sequence of nucleotides on a left side of a symbol and a second invariant sequence of nucleotides on a right side of the symbol.

9. The molecular Turing machine of claim 1, wherein the plurality of transition oligonucleotides include:
   (a) an Inv restriction site;
   (b) a state restriction site adjacent to the Inv restriction site; and
   (c) a new symbol adjacent to the Inv restriction site.

10. The molecular Turing machine of claim 9, wherein the transition oligonucleotides are further comprised of:
   (d) a single-stranded overhang (Coh) which is complementary to the single-stranded overhang generated in the current symbol.

11. The molecular Turing machine of claim 10, wherein the transition oligonucleotides are further comprised of:
   (e) a symbol excision site next to the cohesive end of the current symbol.

12. The molecular Turing machine of claim 11, wherein the symbol excision site is a Class IIS restriction enzyme site selected from the group consisting of BbvI, FokI, BseRI, BsrDI, BpmI, and HgaI.

13. The molecular Turing machine of claim 11, further including:
   (f) a cap restriction site next to the state restriction site.

14. The molecular Turing machine of claim 13, wherein the cap restriction site is a Class IIS restriction enzyme site selected from the group consisting of BbvI, FokI, BseRI, BsrDI, BpmI, and HgaI.

15. The molecular Turing machine of claim 11, further including (g) an end marker restriction site adjacent to the cohesive end of the current symbol.

16. The molecular Turing machine of claim 15, wherein the end marker restriction site is a Class IIS restriction enzyme site selected from the group consisting of BbvI, FokI, BseRI, BsrDI, BpmI, and HgaI.

17. The molecular Turing machine of claim 11, wherein at least one transition oligonucleotide is further comprised of a halt sequence.

18. The molecular Turing machine of claim 17, wherein the halt sequence is comprised of at least 20 nucleotides.

19. The molecular Turing machine of claim 18, wherein the halt sequence is comprised of 40 nucleotides.

20. A method for operating a molecular Turing machine, comprising the steps of:

forming a Turing tape from a molecule of DNA;

conducting an operation on said Turing tape by cutting a current symbol with an asymmetric restriction enzyme in the Turing tape;

mixing a plurality of transition oligonucleotides with the DNA Turing tape at a location of said cutting, to add a new symbol into the DNA Turing tape; and after adding said new symbol, removing a previous symbol from the Turing tape.

21. The method of claim 20, wherein said cutting uses a state restriction enzyme to cut the current symbol to create a unique single-stranded end.

22. The method of claim 20, wherein said cutting uses an invariant enzyme to cut an invariant sequence adjacent to the head.

23. The method of claim 20, wherein said mixing includes adding a DNA ligase to join one of the plurality of transition oligonucleotides to the unique single-stranded end.

24. The method of claim 20, wherein said mixing further includes the step of removing a cap restriction site from one of the plurality of transition oligonucleotides.

25. The method of claim 20, further comprising adding a DNA ligase to cyclize the DNA Turing tape.

26. The method of claim 20, wherein said removing comprises using a symbol-excision restriction enzyme to remove the current symbol.

27. The method of claim 20 further comprising:

checking for a halt sequence.

28. The method of claim 27, wherein said checking includes the steps of adding a biotin label to the halt sequence and using a plurality of streptavidin coated beads to remove DNA Turing tapes which include the halt sequence.

29. The method of claim 28, further including the step of amplification by PCR to read the DNA Turing tape.

* * * * *